United States Patent
Goldman et al.

(10) Patent No.: US 9,949,688 B2
(45) Date of Patent: *Apr. 24, 2018

(54) MICRO VEIN ENHANCER WITH A DUAL BUFFER MODE OF OPERATION

(71) Applicant: AccuVein, Inc., Cold Spring Harbor, NY (US)

(72) Inventors: Ron Goldman, Cold Spring Harbor, NY (US); David Hunt, Cincinnati, OH (US); Mark Mock, Covington, KY (US); Graham Marshall, Shoreham, NY (US); Stephen P Conlon, Cold Spring Harbor, NY (US); Robert Roth, Cincinnati, OH (US)

(73) Assignee: AccuVein, Inc., Cold Spring Harbor, NY (US)

(*) Notice: Subject to any disclaimer, the term of this patent is extended or adjusted under 35 U.S.C. 154(b) by 266 days.

This patent is subject to a terminal disclaimer.

(21) Appl. No.: 14/799,863

(22) Filed: Jul. 15, 2015

(65) Prior Publication Data

US 2016/0038078 A1 Feb. 11, 2016

Related U.S. Application Data

(60) Continuation of application No. 14/197,573, filed on Mar. 5, 2014, now Pat. No. 9,125,629, which is a
(Continued)

(51) Int. Cl.
*A61B 5/05* (2006.01)
*A61B 5/00* (2006.01)
(Continued)

(52) U.S. Cl.
CPC ............ *A61B 5/489* (2013.01); *A61B 5/0037* (2013.01); *A61B 5/0059* (2013.01);
(Continued)

(58) Field of Classification Search
None
See application file for complete search history.

(56) References Cited

U.S. PATENT DOCUMENTS 3,136,310 A   6/1964 Meltzer
3,349,762 A  10/1967 Kapany
(Continued)

FOREIGN PATENT DOCUMENTS

FR   2289149   5/1976
GB   1298707  12/1972
(Continued)

OTHER PUBLICATIONS

Wiklof, Chris, "Display Technology Spawns Laser Camera," LaserFocusWorld, Dec. 1, 2004, vol. 40, Issue 12, PennWell Corp., USA.
(Continued)

*Primary Examiner* — James Kish
(74) *Attorney, Agent, or Firm* — Thomas A. O'Rourke; Bodner & O'Rourke, LLP

(57) ABSTRACT

The present invention is a Miniature Vein Enhancer that includes a Miniature Projection Head. The Miniature Projection Head may be operated in one of three modes, AFM, DBM, and RTM. The Miniature Projection Head of the present invention projects an image of the veins of a patient, which aids the practitioner in pinpointing a vein for an intravenous drip, blood test and the like. The Miniature projection head may have a cavity for a power source or it may have a power source located in a body portion of the Miniature Vein Enhancer. The Miniature Vein Enhancer may be attached to one of several improved needle protectors, or the Miniature Vein Enhancer may be attached to a body similar to a flashlight for hand held use. The Miniature Vein
(Continued)

Enhancer of the present invention may also be attached to a magnifying glass, a flat panel display, and the like.

19 Claims, 45 Drawing Sheets

Related U.S. Application Data continuation of application No. 12/931,151, filed on Jan. 25, 2011, now Pat. No. 8,712,498, which is a division of application No. 11/478,322, filed on Jun. 29, 2006, now Pat. No. 8,478,386.

(60) Provisional application No. 60/757,704, filed on Jan. 10, 2006.

(51) Int. Cl.
*A61M 5/42* (2006.01)
*A61M 5/46* (2006.01)
*A61B 17/34* (2006.01)
*A61B 19/00* (2006.01)
*A61B 90/00* (2016.01)

(52) U.S. Cl.
CPC .......... *A61B 5/0062* (2013.01); *A61B 5/0068* (2013.01); *A61B 5/0071* (2013.01); *A61B 5/0075* (2013.01); *A61B 5/0079* (2013.01); *A61B 5/0082* (2013.01); *A61B 5/6824* (2013.01); *A61B 5/6831* (2013.01); *A61B 5/6887* (2013.01); *A61B 5/743* (2013.01); *A61B 5/7475* (2013.01); *A61B 17/3403* (2013.01); *A61M 5/427* (2013.01); *A61M 5/46* (2013.01); *A61B 2019/202* (2013.01); *A61B 2090/366* (2016.02); *A61B 2560/0214* (2013.01); *A61B 2560/0425* (2013.01); *A61B 2560/0431* (2013.01); *A61B 2562/028* (2013.01)

(56) References Cited

U.S. PATENT DOCUMENTS

| | | |
|---|---|---|
| 3,511,227 A | 5/1970 | Johnson |
| 3,527,932 A | 9/1970 | Thomas |
| 3,818,129 A | 6/1974 | Yamamoto |
| 3,984,629 A | 10/1976 | Gorog |
| 4,030,209 A | 6/1977 | Dreidling |
| 4,057,784 A | 11/1977 | Tafoya |
| 4,109,647 A | 8/1978 | Stern |
| 4,162,405 A | 7/1979 | Chance |
| 4,182,322 A | 1/1980 | Miller |
| 4,185,808 A | 1/1980 | Donohoe et al. |
| 4,213,678 A | 7/1980 | Pomerantzeff |
| 4,265,227 A | 5/1981 | Ruge |
| 4,312,357 A | 1/1982 | Andersson et al. |
| 4,315,318 A | 2/1982 | Kato |
| 4,321,930 A | 3/1982 | Jobsis et al. |
| 4,393,366 A | 7/1983 | Hill |
| 4,495,949 A | 1/1985 | Stoller |
| 4,502,075 A | 2/1985 | DeForest et al. |
| 4,510,938 A | 4/1985 | Jobsis |
| 4,536,790 A | 8/1985 | Kruger |
| 4,565,968 A | 1/1986 | Macovski |
| 4,567,896 A | 2/1986 | Bamea |
| 4,576,175 A | 3/1986 | Epstein |
| 4,586,190 A | 4/1986 | Tsuji |
| 4,590,948 A | 5/1986 | Nilsson |
| 4,596,254 A | 6/1986 | Adrian |
| 4,619,249 A | 10/1986 | Landry |
| 4,669,467 A | 6/1987 | Willet |
| 4,697,147 A | 9/1987 | Moran |
| 4,699,149 A | 10/1987 | Rice |
| 4,703,758 A | 11/1987 | Omura |
| 4,766,299 A | 8/1988 | Tierney et al. |
| 4,771,308 A | 9/1988 | Tejima et al. |
| 4,780,919 A | 11/1988 | Harrison |
| 4,799,103 A | 1/1989 | Mucherheide |
| 4,817,622 A | 4/1989 | Pennypacker et al. |
| 4,846,183 A | 7/1989 | Martin |
| 4,862,894 A | 9/1989 | Fujii |
| 4,899,756 A | 2/1990 | Sonek |
| 4,901,019 A | 2/1990 | Wedeen |
| 4,926,867 A | 5/1990 | Kanda |
| RE33,234 E | 6/1990 | Landry |
| 5,074,642 A | 12/1991 | Hicks |
| 5,088,493 A | 2/1992 | Giannini |
| 5,103,497 A | 4/1992 | Hicks |
| 5,146,923 A | 9/1992 | Dhawan |
| 5,174,298 A | 12/1992 | Dolfi |
| 5,184,188 A | 2/1993 | Bull |
| 5,214,458 A | 5/1993 | Kanai |
| 5,222,495 A | 6/1993 | Clarke |
| 5,261,581 A | 11/1993 | Harden |
| 5,293,873 A | 3/1994 | Fang |
| 5,339,817 A | 8/1994 | Nilsson |
| 5,371,347 A | 12/1994 | Plesko |
| 5,406,070 A | 4/1995 | Edgar et al. |
| 5,418,546 A | 5/1995 | Nakagakiuchi et al. |
| 5,423,091 A | 6/1995 | Lange |
| 5,436,655 A | 7/1995 | Hiyama |
| D362,910 S | 10/1995 | Creaghan |
| 5,455,157 A | 10/1995 | Adachi |
| 5,494,032 A | 2/1996 | Robinson |
| 5,497,769 A | 3/1996 | Gratton |
| 5,504,316 A | 4/1996 | Bridgelall et al. |
| 5,519,208 A | 5/1996 | Esparza et al. |
| 5,541,820 A | 7/1996 | McLaughlin |
| 5,542,421 A | 8/1996 | Erdman |
| 5,598,842 A | 2/1997 | Ishihara et al. |
| 5,603,328 A | 2/1997 | Zucker et al. |
| 5,608,210 A | 3/1997 | Esparza et al. |
| 5,610,387 A | 3/1997 | Bard et al. |
| 5,625,458 A | 4/1997 | Alfano |
| 5,631,976 A | 5/1997 | Bone et al. |
| 5,655,530 A | 8/1997 | Messerschmidt |
| 5,678,555 A | 10/1997 | O'Connell |
| 5,716,796 A | 2/1998 | Bull |
| 5,719,399 A | 2/1998 | Alfano et al. |
| 5,747,789 A | 5/1998 | Godik |
| 5,756,981 A | 5/1998 | Roustaei et al. |
| 5,758,650 A | 6/1998 | Miller |
| 5,772,593 A | 6/1998 | Hakamata |
| 5,787,185 A | 7/1998 | Clayden |
| 5,814,040 A | 9/1998 | Nelson |
| 5,836,877 A | 11/1998 | Zavislan |
| 5,847,394 A | 12/1998 | Alfano et al. |
| 5,860,967 A | 1/1999 | Zavislan et al. |
| 5,929,443 A | 7/1999 | Alfano et al. |
| 5,946,220 A | 8/1999 | Lemelson |
| 5,947,906 A | 9/1999 | Dawson, Jr. et al. |
| 5,966,204 A | 10/1999 | Abe |
| 5,969,754 A | 10/1999 | Zeman |
| 5,982,553 A | 11/1999 | Bloom et al. |
| 5,988,817 A | 11/1999 | Mizushima et al. |
| 5,995,856 A | 11/1999 | Manheimer et al. |
| 5,995,866 A | 11/1999 | Lemelson |
| 6,006,126 A | 12/1999 | Cosman |
| 6,032,070 A | 2/2000 | Flock et al. |
| 6,056,692 A | 5/2000 | Schwartz |
| 6,061,583 A | 5/2000 | Shihara et al. |
| 6,101,036 A | 8/2000 | Bloom |
| 6,122,042 A | 9/2000 | Wunderman |
| 6,132,379 A | 10/2000 | Patacsil |
| 6,135,599 A | 10/2000 | Fang |
| 6,141,985 A | 11/2000 | Cluzeau et al. |
| 6,142,650 A | 11/2000 | Brown et al. |
| 6,149,644 A | 11/2000 | Xie |
| 6,171,301 B1 | 1/2001 | Nelson |
| 6,178,340 B1 | 1/2001 | Svetliza |
| 6,230,046 B1 | 5/2001 | Crane et al. |
| 6,240,309 B1 | 5/2001 | Yamashita |

(56) References Cited

U.S. PATENT DOCUMENTS

| | | |
|---|---|---|
| 6,251,073 B1 | 6/2001 | Imran et al. |
| 6,263,227 B1 | 7/2001 | Boggett et al. |
| 6,301,375 B1 | 10/2001 | Choi |
| 6,305,804 B1 | 10/2001 | Rice |
| 6,314,311 B1 | 11/2001 | Williams et al. |
| 6,334,850 B1 | 1/2002 | Amano et al. |
| 6,353,753 B1 | 3/2002 | Flock |
| 6,424,858 B1 | 7/2002 | Williams |
| 6,436,655 B1 | 8/2002 | Bull |
| 6,438,396 B1 | 8/2002 | Cook et al. |
| 6,463,309 B1 | 10/2002 | Ilia |
| 6,464,646 B1 | 10/2002 | Shalom et al. |
| 6,523,955 B1 | 2/2003 | Eberl |
| 6,542,246 B1 | 4/2003 | Toida |
| 6,556,854 B1 | 4/2003 | Sato |
| 6,556,858 B1 | 4/2003 | Zeman |
| 6,599,247 B1 | 7/2003 | Stetten |
| 6,631,286 B2 | 10/2003 | Pfeiffer |
| 6,648,227 B2 | 11/2003 | Swartz et al. |
| 6,650,916 B2 | 11/2003 | Cook et al. |
| 6,689,075 B2 | 2/2004 | West |
| 6,690,964 B2 | 2/2004 | Bieger et al. |
| 6,702,749 B2 | 3/2004 | Paladini et al. |
| 6,719,257 B1 | 4/2004 | Greene et al. |
| 6,755,789 B2 | 6/2004 | Stringer |
| 6,777,199 B2 | 8/2004 | Bull |
| 6,782,161 B2 | 9/2004 | Barolet et al. |
| 6,845,190 B1 | 1/2005 | Smithwick |
| 6,882,875 B1 | 4/2005 | Crowley |
| 6,889,075 B2 | 5/2005 | Marchitto et al. |
| 6,913,202 B2 | 7/2005 | Tsikos et al. |
| 6,923,762 B1 | 8/2005 | Creaghan |
| 6,980,852 B2 | 12/2005 | Jersey-Wiluhn et al. |
| 7,092,087 B2 | 8/2006 | Kumar |
| 7,113,817 B1 | 9/2006 | Winchester |
| 7,158,660 B2 | 1/2007 | Gee et al. |
| 7,158,859 B2 | 1/2007 | Wang |
| 7,225,005 B2 | 5/2007 | Kaufman et al. |
| 7,227,611 B2 | 6/2007 | Hull et al. |
| 7,239,909 B2 | 7/2007 | Zeman |
| 7,247,832 B2 | 7/2007 | Webb |
| 7,283,181 B2 | 10/2007 | Allen |
| 7,302,174 B2 | 11/2007 | Tan et al. |
| 7,333,213 B2 | 2/2008 | Kempe |
| D566,283 S | 4/2008 | Brafford et al. |
| 7,359,531 B2 | 4/2008 | Endoh et al. |
| 7,376,456 B2 | 5/2008 | Marshik-Geurts |
| 7,431,695 B1 | 10/2008 | Creaghan |
| 7,532,746 B2 | 5/2009 | Marcotte et al. |
| 7,545,837 B2 | 6/2009 | Oka |
| 7,559,895 B2 | 7/2009 | Stetten |
| 7,579,592 B2 | 8/2009 | Kaushal |
| 7,608,057 B2 | 10/2009 | Woehr et al. |
| 7,708,695 B2 | 5/2010 | Akkermans |
| 7,792,334 B2 | 9/2010 | Cohen |
| 7,848,103 B2 | 12/2010 | Cannon |
| 7,904,138 B2 | 3/2011 | Ustuner |
| 7,904,139 B2 | 3/2011 | Chance |
| 7,925,332 B2 | 4/2011 | Crane et al. |
| 7,966,051 B2 | 6/2011 | Xie |
| 8,032,205 B2 | 10/2011 | Mullani |
| 8,078,263 B2 | 12/2011 | Zeman et al. |
| 8,187,189 B2 | 5/2012 | Jung et al. |
| 8,199,189 B2 | 6/2012 | Kagenow et al. |
| 8,320,998 B2 | 11/2012 | Sato |
| 8,336,839 B2 | 12/2012 | Timoszyk et al. |
| 8,364,246 B2 | 1/2013 | Thierman |
| 8,494,616 B2 | 7/2013 | Zeman |
| 8,498,694 B2 | 7/2013 | McGuire, Jr. et al. |
| 8,509,495 B2 | 8/2013 | Xu et al. |
| 8,548,572 B2 | 10/2013 | Crane et al. |
| 8,630,465 B2 | 1/2014 | Wieringa |
| 8,649,848 B2 | 2/2014 | Crane et al. |
| 2001/0006426 A1 | 7/2001 | Son |
| 2001/0056237 A1 | 12/2001 | Cane |
| 2002/0016533 A1 | 2/2002 | Marchitto |
| 2002/0118338 A1 | 8/2002 | Kohayakawa |
| 2002/0188203 A1 | 12/2002 | Smith |
| 2003/0018271 A1 | 1/2003 | Kimble |
| 2003/0052105 A1 | 3/2003 | Nagano |
| 2003/0120154 A1 | 6/2003 | Sauer |
| 2003/0125629 A1 | 7/2003 | Ustuner |
| 2003/0156260 A1 | 8/2003 | Putilin |
| 2004/0015158 A1 | 1/2004 | Chen et al. |
| 2004/0022421 A1 | 2/2004 | Endoh et al. |
| 2004/0046031 A1 | 3/2004 | Knowles et al. |
| 2004/0171923 A1 | 9/2004 | Kalafut et al. |
| 2004/0222301 A1 | 11/2004 | Willins et al. |
| 2005/0017924 A1 | 1/2005 | Utt et al. |
| 2005/0033145 A1 | 2/2005 | Graham et al. |
| 2005/0043596 A1 | 2/2005 | Chance |
| 2005/0047134 A1 | 3/2005 | Mueller et al. |
| 2005/0085802 A1 | 4/2005 | Gruzdev |
| 2005/0113650 A1 | 5/2005 | Pacione et al. |
| 2005/0131291 A1 | 6/2005 | Floyd et al. |
| 2005/0135102 A1 | 6/2005 | Gardiner et al. |
| 2005/0141069 A1 | 6/2005 | Wood et al. |
| 2005/0143662 A1 | 6/2005 | Marchitto et al. |
| 2005/0146765 A1 | 7/2005 | Turner |
| 2005/0154303 A1 | 7/2005 | Walker |
| 2005/0157939 A1 | 7/2005 | Arsenault et al. |
| 2005/0161051 A1 | 7/2005 | Pankratov et al. |
| 2005/0168980 A1 | 8/2005 | Dryden et al. |
| 2005/0174777 A1 | 8/2005 | Cooper et al. |
| 2005/0175048 A1 | 8/2005 | Stern et al. |
| 2005/0187477 A1 | 8/2005 | Serov |
| 2005/0215875 A1 | 9/2005 | Khou |
| 2005/0265586 A1 | 12/2005 | Rowe et al. |
| 2005/0281445 A1 | 12/2005 | Marcotte et al. |
| 2006/0007134 A1 | 1/2006 | Ting |
| 2006/0020212 A1 | 1/2006 | Xu |
| 2006/0025679 A1 | 2/2006 | Viswanathan et al. |
| 2006/0052690 A1 | 3/2006 | Sirohey et al. |
| 2006/0081252 A1 | 4/2006 | Wood |
| 2006/0100523 A1 | 5/2006 | Ogle |
| 2006/0103811 A1 | 5/2006 | May et al. |
| 2006/0122515 A1 | 6/2006 | Zeman |
| 2006/0129037 A1 | 6/2006 | Kaufman et al. |
| 2006/0129038 A1 | 6/2006 | Zelenchuk et al. |
| 2006/0151449 A1 | 7/2006 | Warner |
| 2006/0173351 A1 | 8/2006 | Marcotte et al. |
| 2006/0184040 A1 | 8/2006 | Keller et al. |
| 2006/0206027 A1 | 9/2006 | Malone |
| 2006/0232660 A1 | 10/2006 | Nakajima et al. |
| 2006/0253010 A1 | 11/2006 | Brady et al. |
| 2006/0271028 A1 | 11/2006 | Altshuler et al. |
| 2007/0016079 A1 | 1/2007 | Freeman et al. |
| 2007/0070302 A1 | 3/2007 | Govorkov |
| 2007/0115435 A1 | 5/2007 | Rosendaal |
| 2007/0176851 A1 | 8/2007 | Wiley |
| 2008/0045841 A1 | 2/2008 | Wood et al. |
| 2008/0147147 A1 | 6/2008 | Griffiths et al. |
| 2008/0194930 A1 | 8/2008 | Harris et al. |
| 2009/0018414 A1 | 1/2009 | Toofan |
| 2009/0171205 A1 | 7/2009 | Kharin |
| 2010/0051808 A1 | 3/2010 | Zeman et al. |
| 2010/0061598 A1 | 3/2010 | Seo |
| 2010/0087787 A1 | 4/2010 | Woehr et al. |
| 2010/0177184 A1 | 7/2010 | Berryhill et al. |
| 2010/0312120 A1 | 12/2010 | Meier |
| 2014/0039309 A1 | 2/2014 | Harris et al. |
| 2014/0046291 A1 | 2/2014 | Harris et al. |

FOREIGN PATENT DOCUMENTS

| | | |
|---|---|---|
| GB | 1507329 | 4/1978 |
| JP | S60-108043 A | 6/1985 |
| JP | 04-042944 | 2/1992 |
| JP | 07-255847 | 10/1995 |
| JP | 08023501 A | 1/1996 |
| JP | 08-164123 | 6/1996 |
| JP | 2000/316866 A | 11/2000 |
| JP | 2002 328428 A | 11/2002 |
| JP | 2002/345963 A | 12/2002 |

(56) References Cited

FOREIGN PATENT DOCUMENTS

| | | |
|---|---|---|
| JP | 2004 237051 | 8/2004 |
| JP | 2004/329786 A | 11/2004 |
| KR | 2003/0020152 A | 3/2003 |
| WO | WO 1994 22370 | 10/1994 |
| WO | WO 96/39925 | 12/1996 |
| WO | WO 1996 39926 | 12/1996 |
| WO | WO 9826583 | 6/1998 |
| WO | WO 99/48420 | 9/1999 |
| WO | WO 2001 82786 | 11/2001 |
| WO | WO 2003 009750 | 2/2003 |
| WO | WO 2005053773 | 6/2005 |
| WO | WO 2007 078447 | 12/2007 |

OTHER PUBLICATIONS

Nikbin, Darius, "IPMS Targets Colour Laser Projectors," Optics & Laser Europe, Mar. 2006, Issue 137, p. 11.
http://sciencegeekgirl.wordpress, com/category/science-myths/page/2/Myth 7: Blood is Blue.
http://www.exploratorium.edu/sports/hnds_up/hands6.html "Hands Up! To Do & Notice: Getting the Feel of Your Hand".
http://www.wikihow.com/See-Blood-Veins-in-Your-Hand-With-a-Flashlight "How to See Blood Veins in Your Hand With a Flashlight".

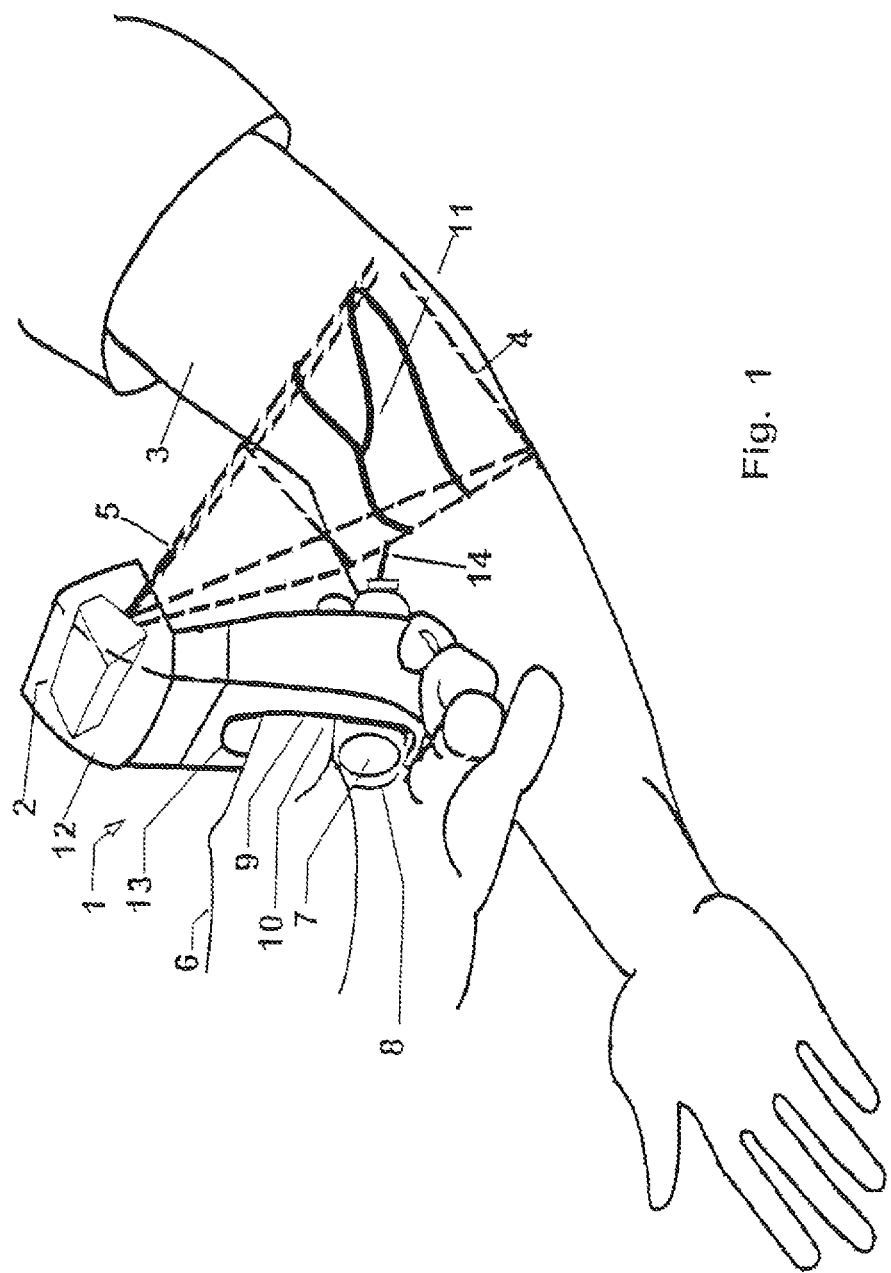

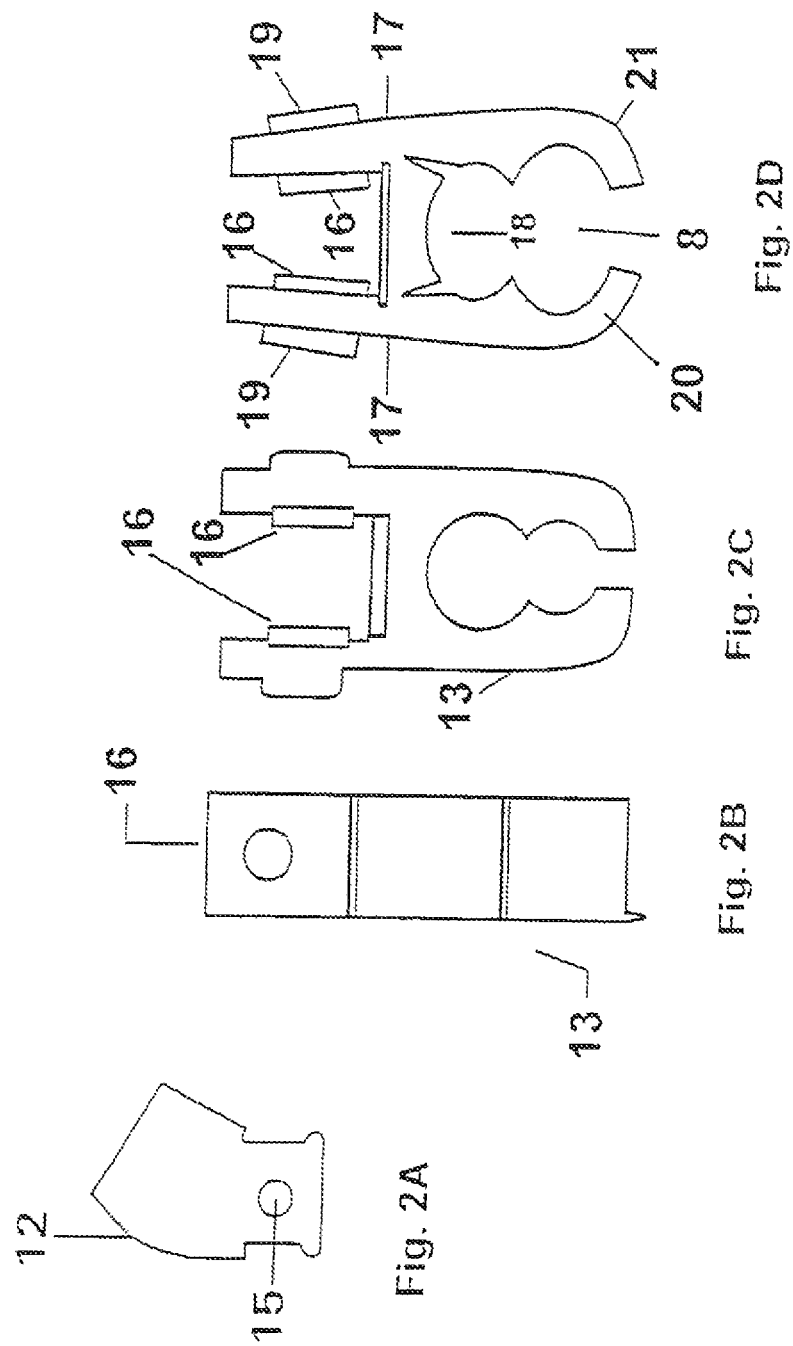

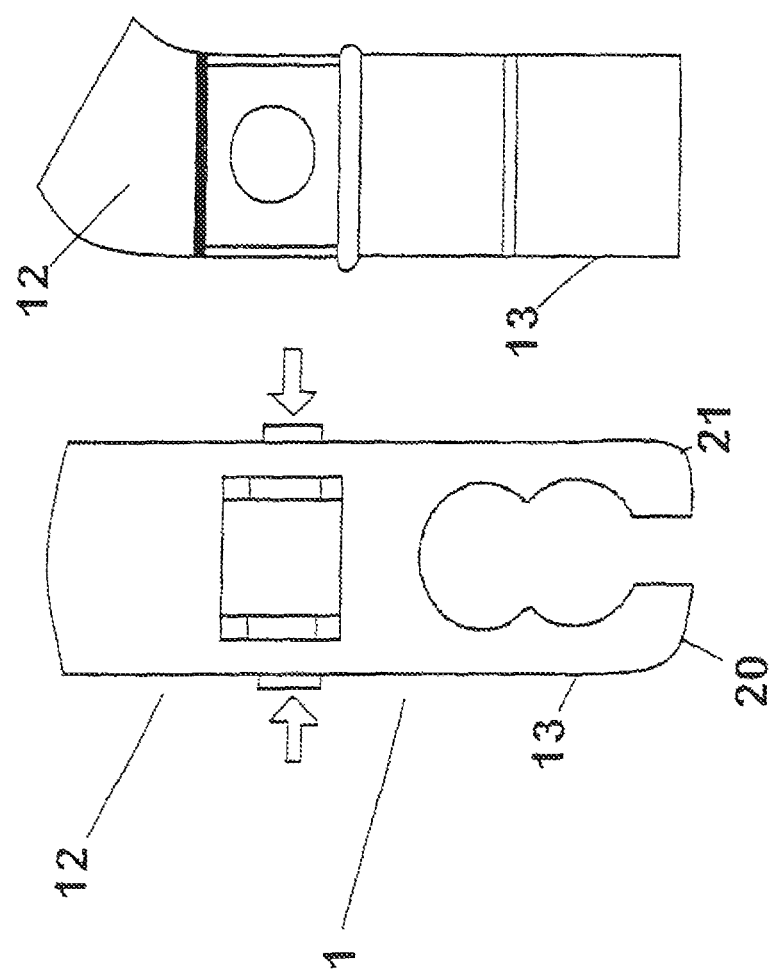

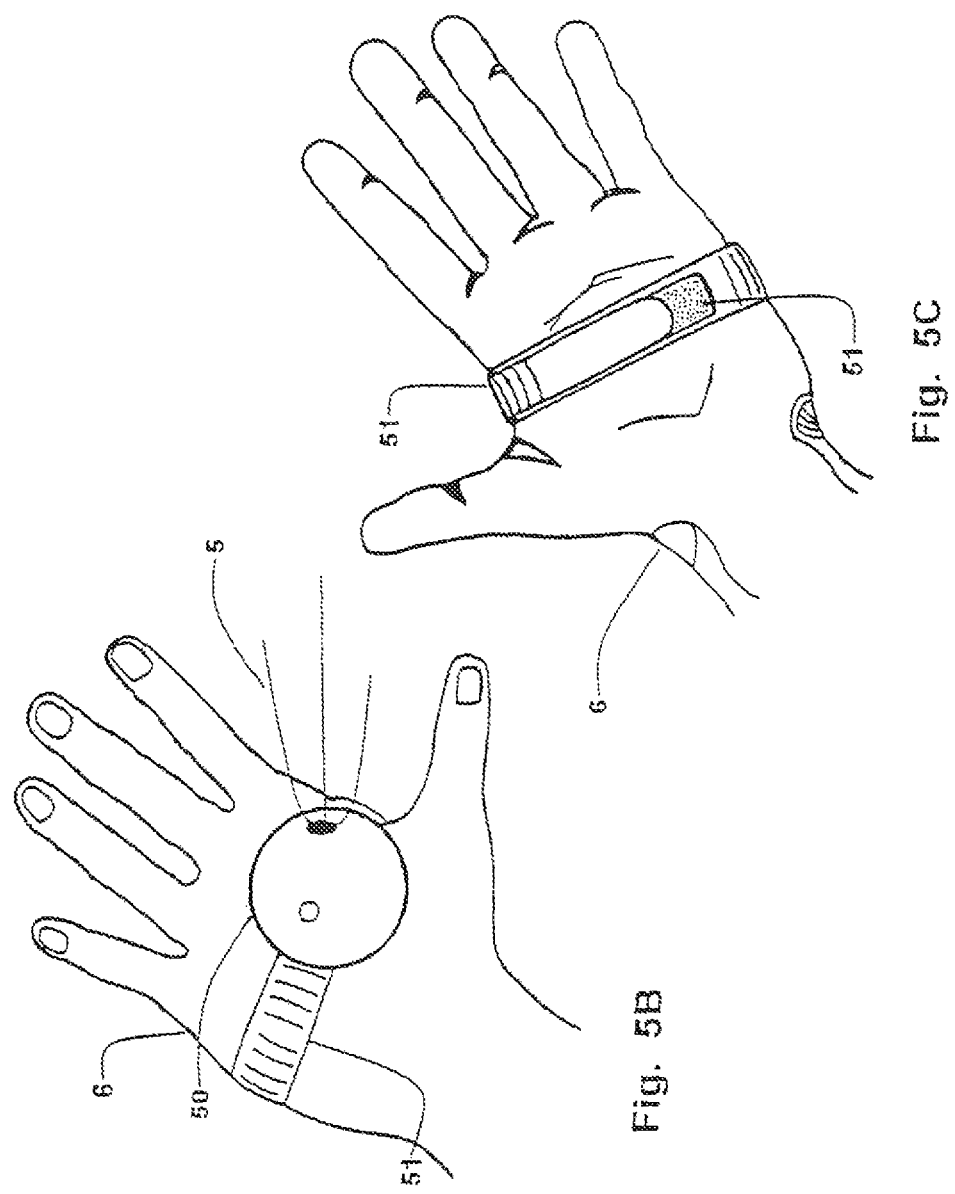

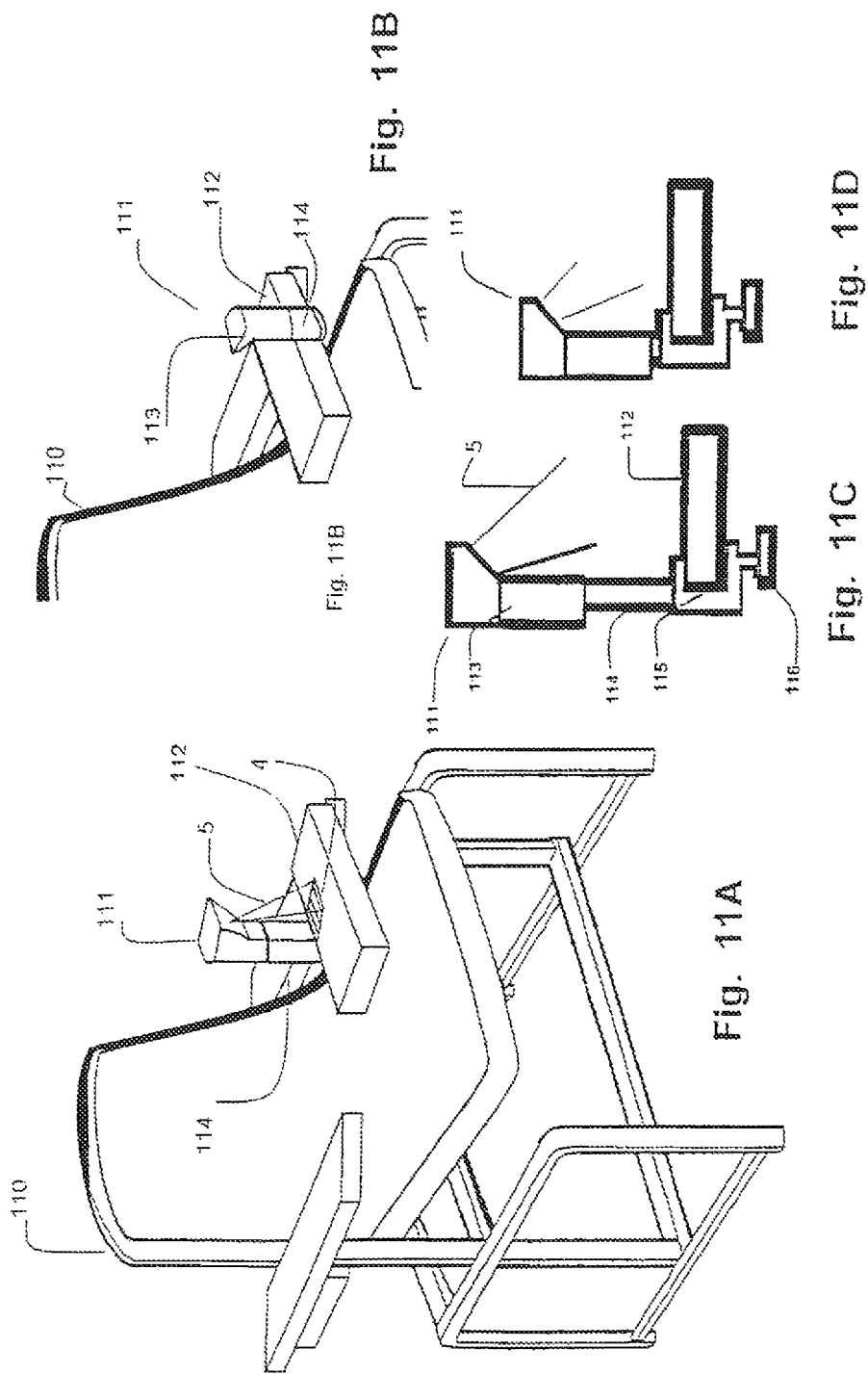

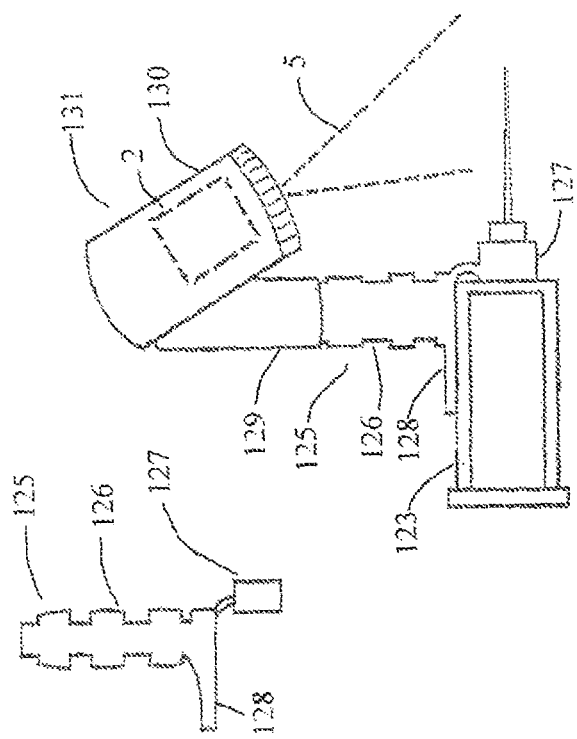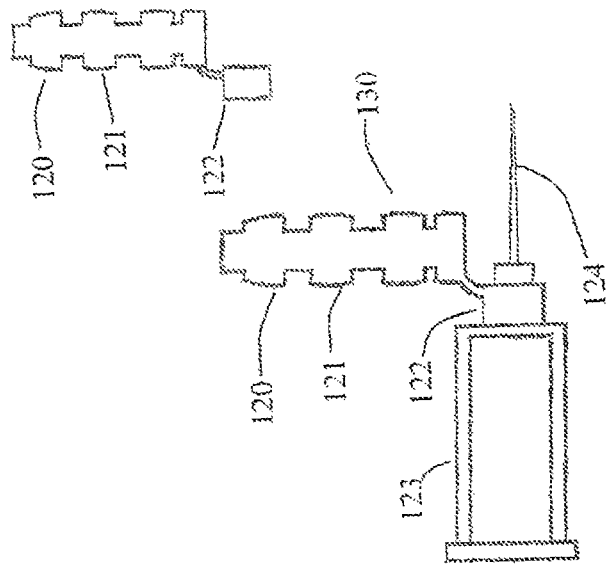

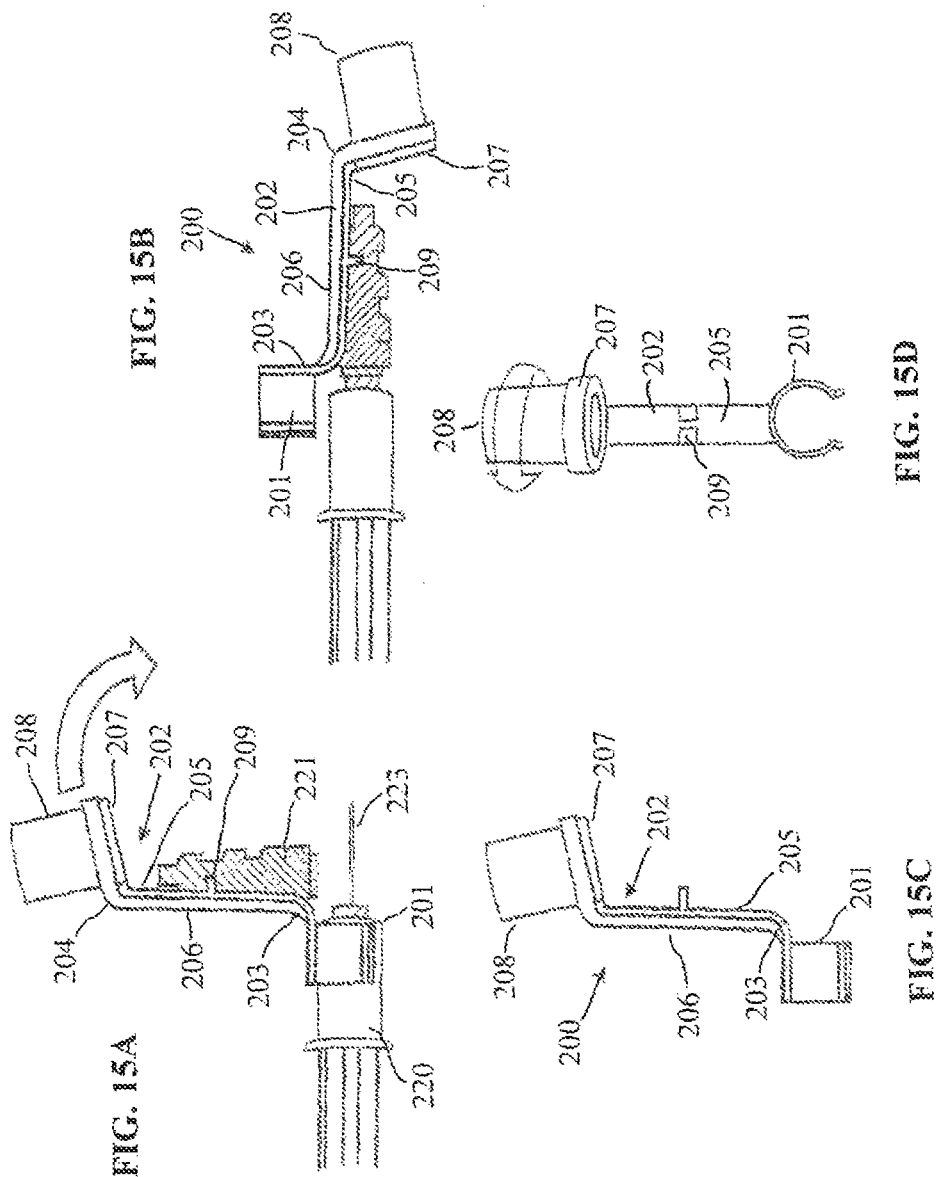

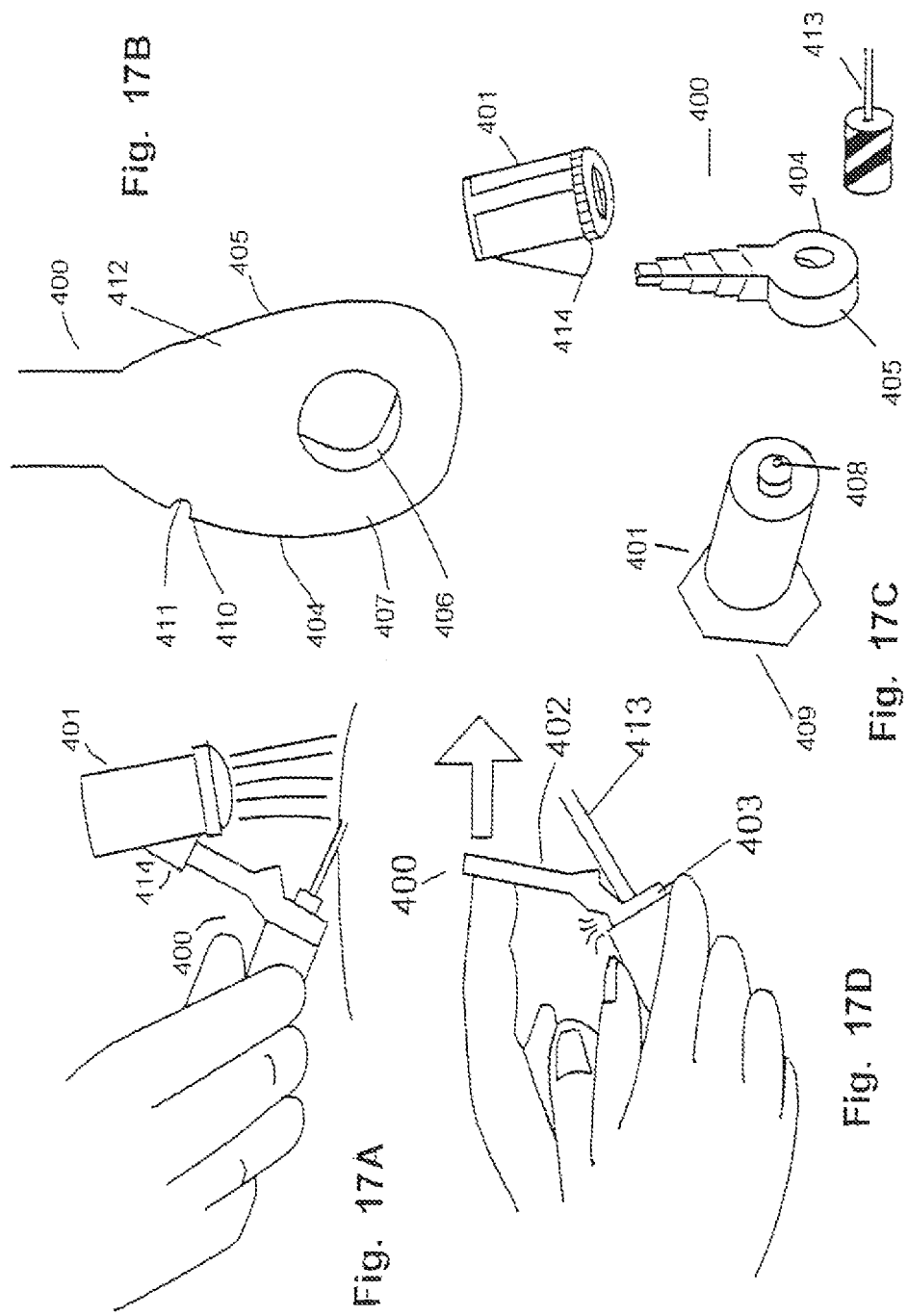

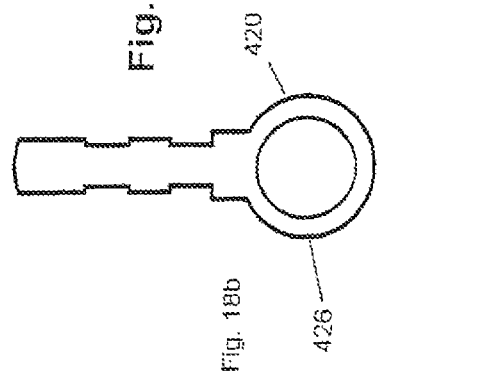
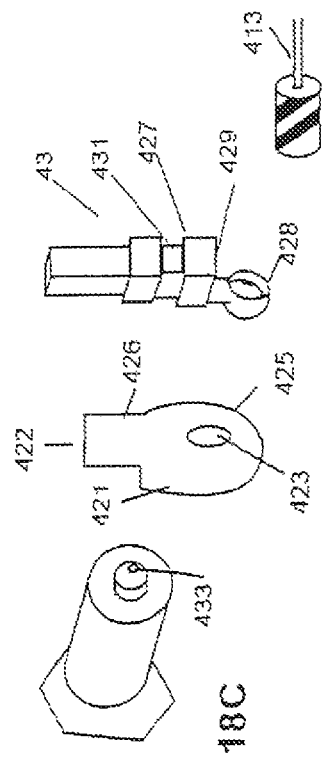
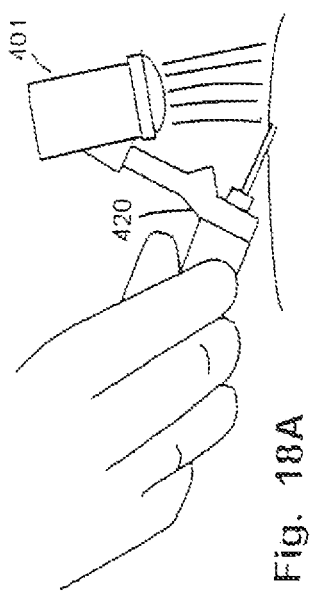
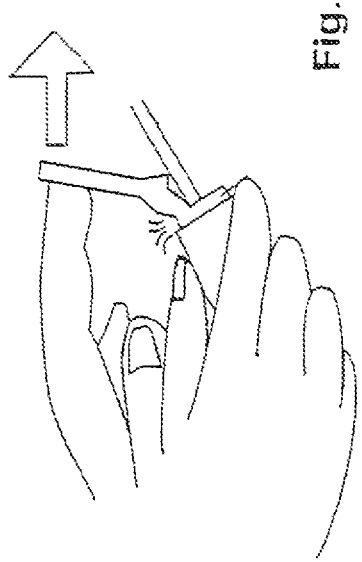
Fig. 18A  Fig. 18B  Fig. 18C  Fig. 18D

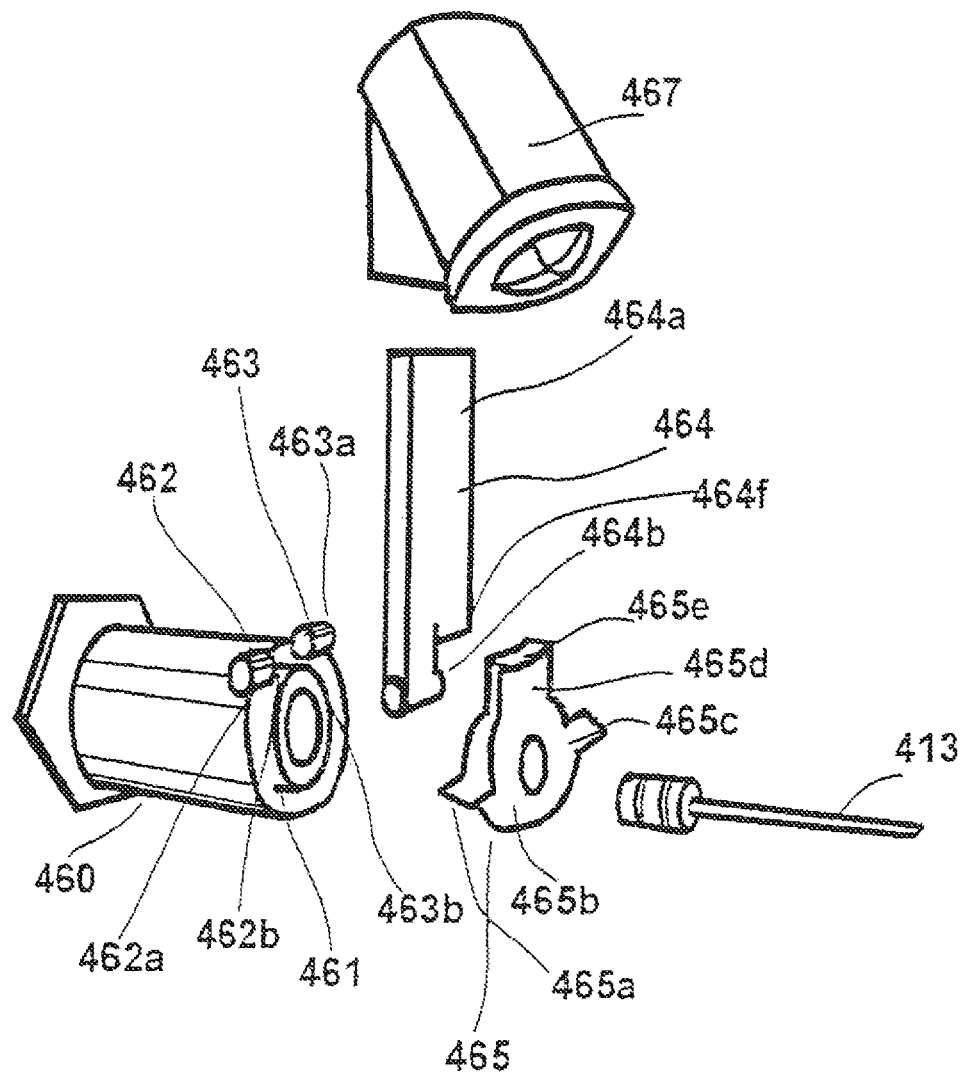

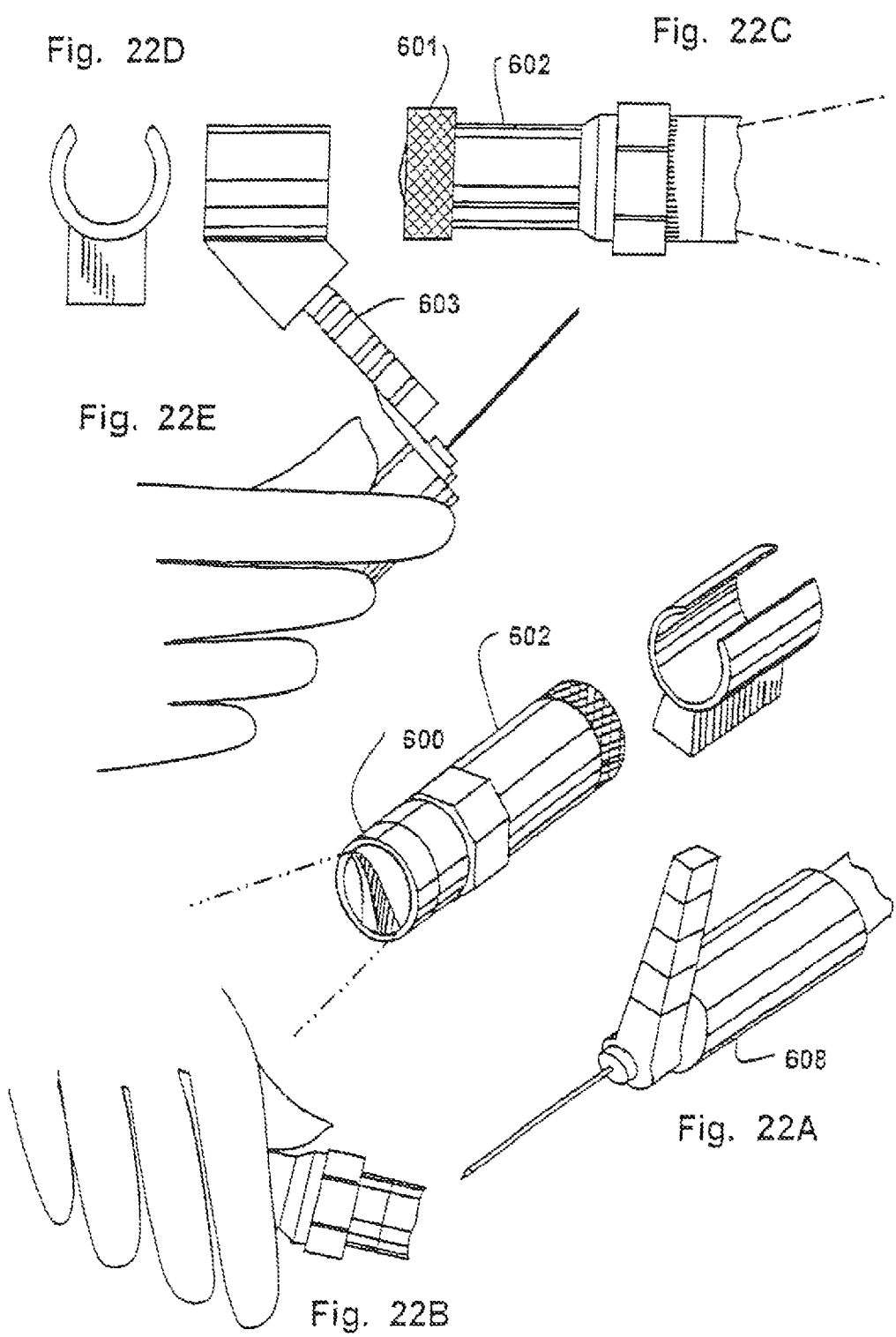

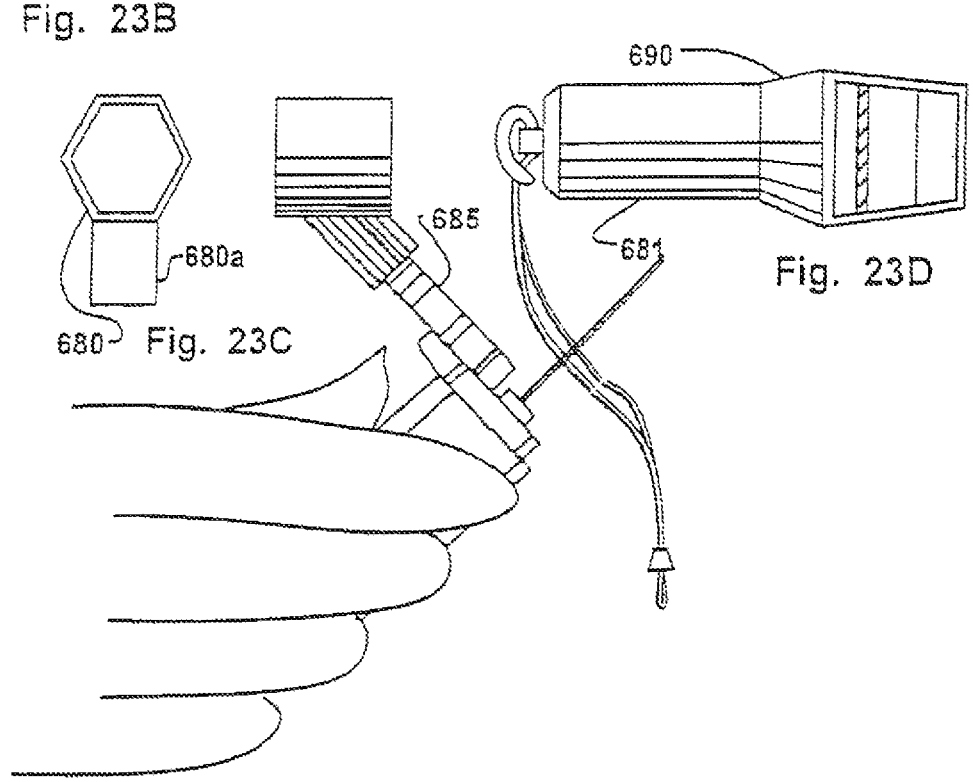
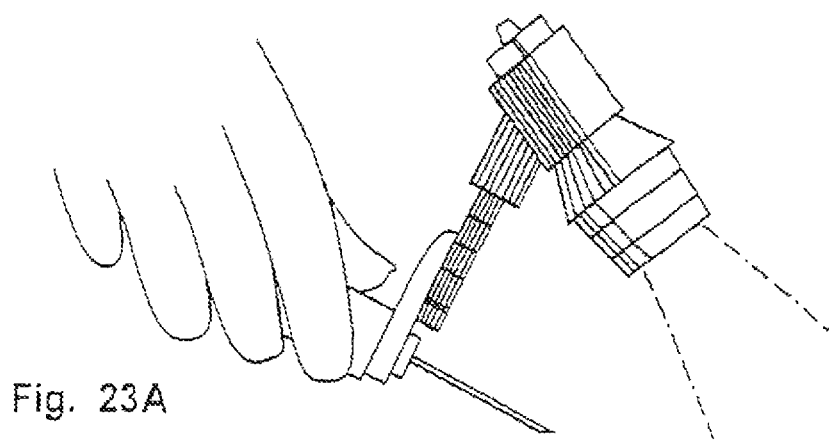
Fig. 23B
Fig. 23C
Fig. 23D
Fig. 23A

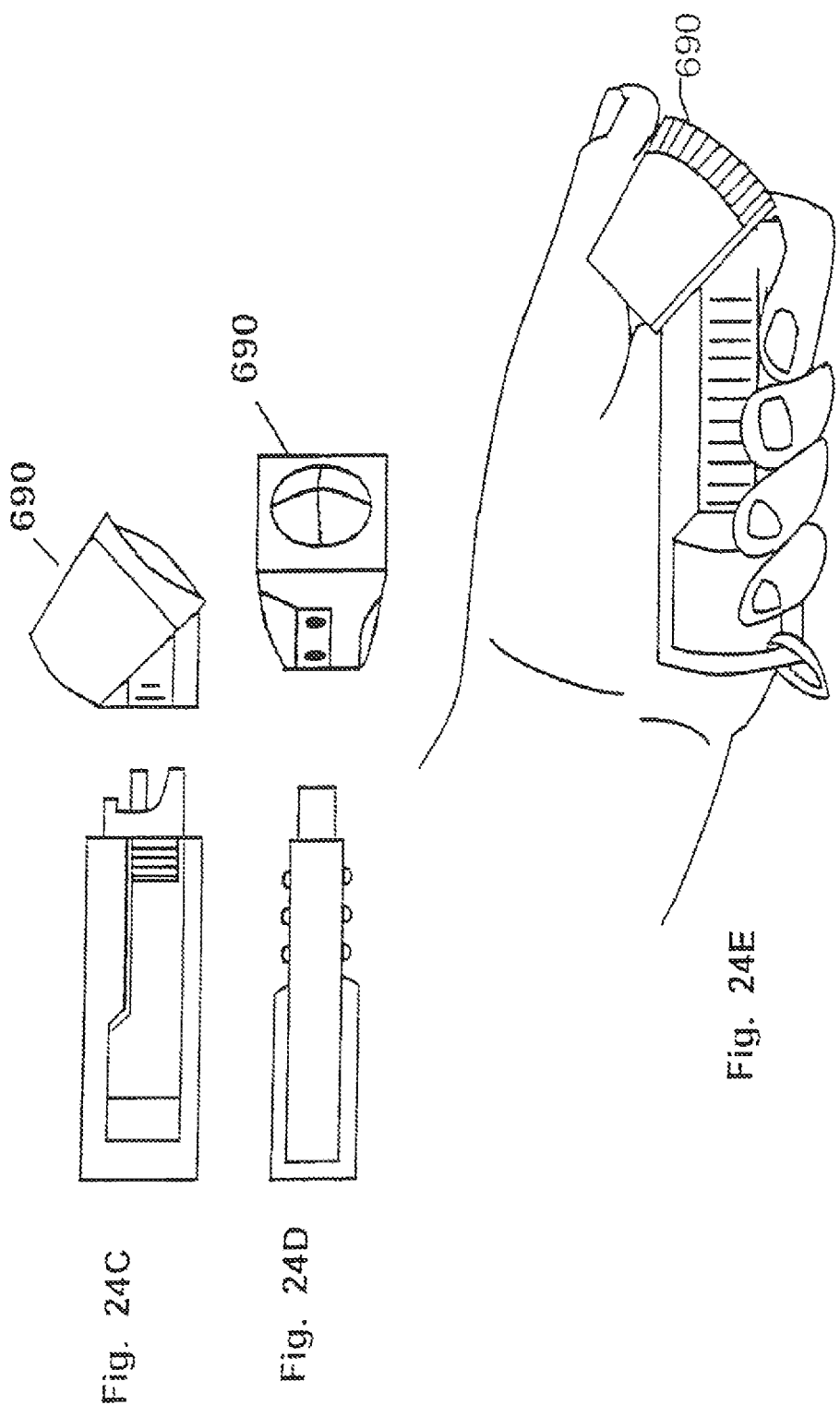

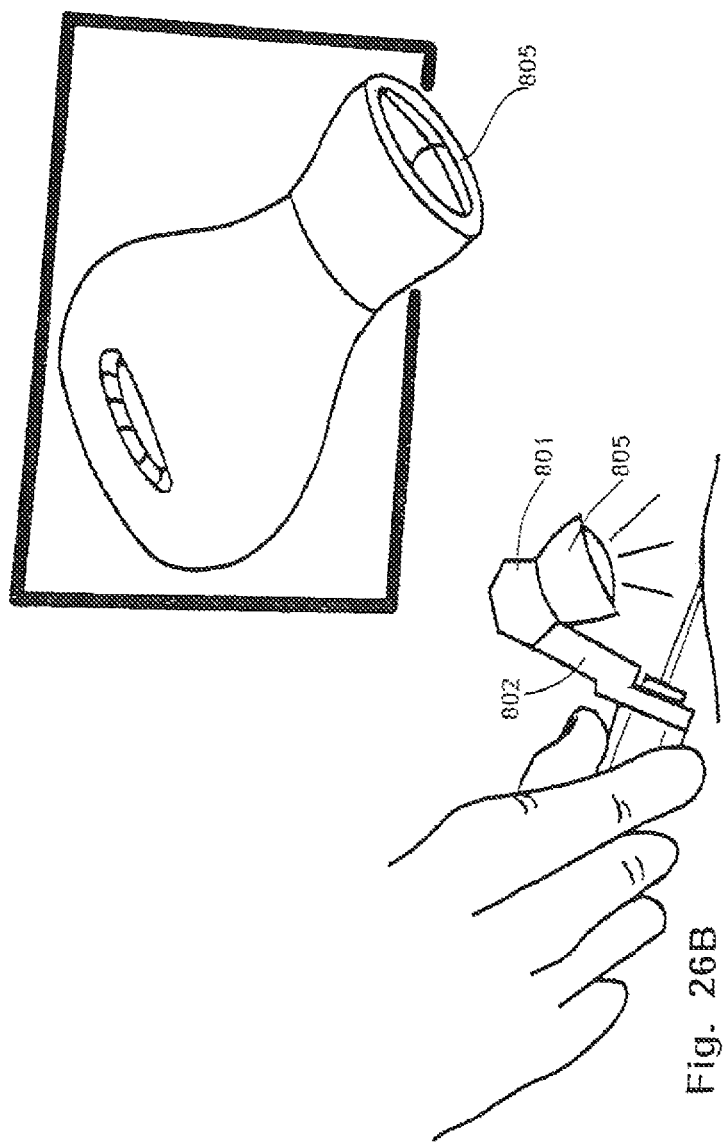

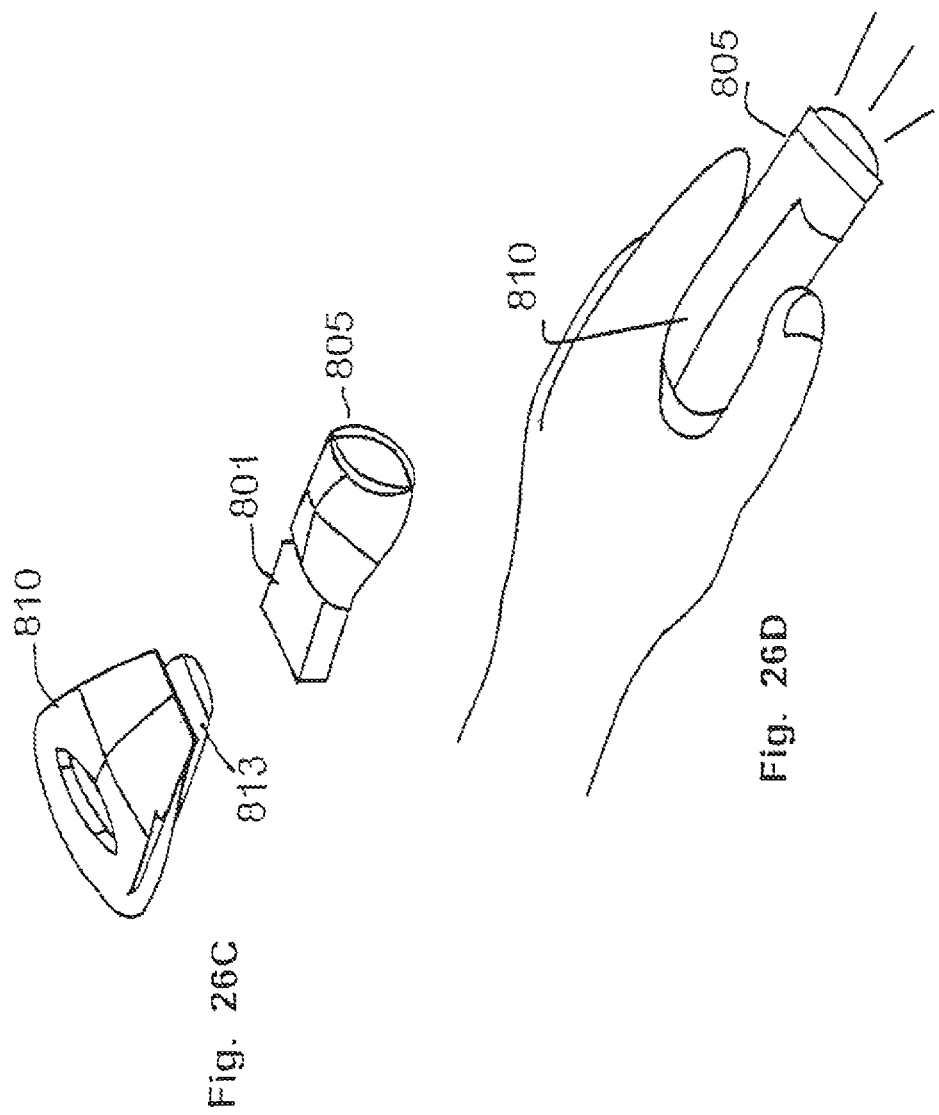

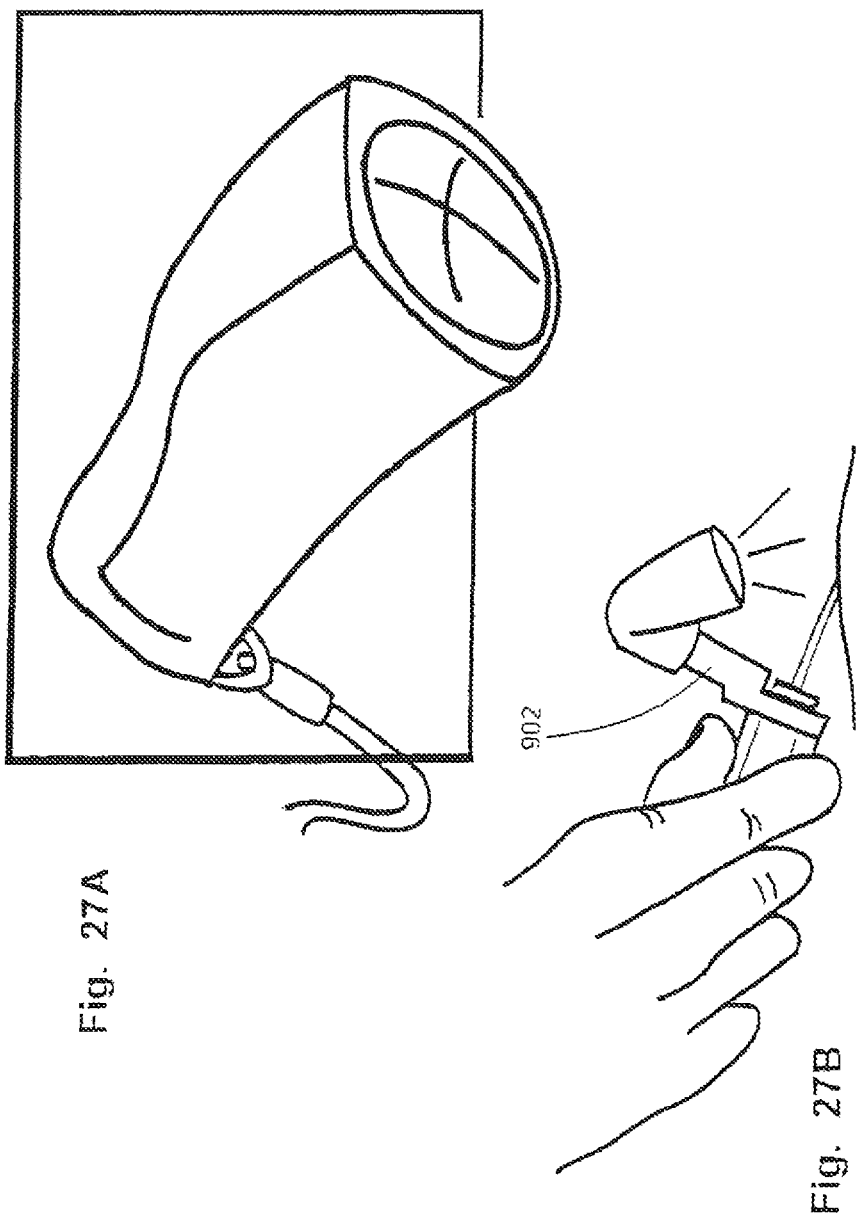

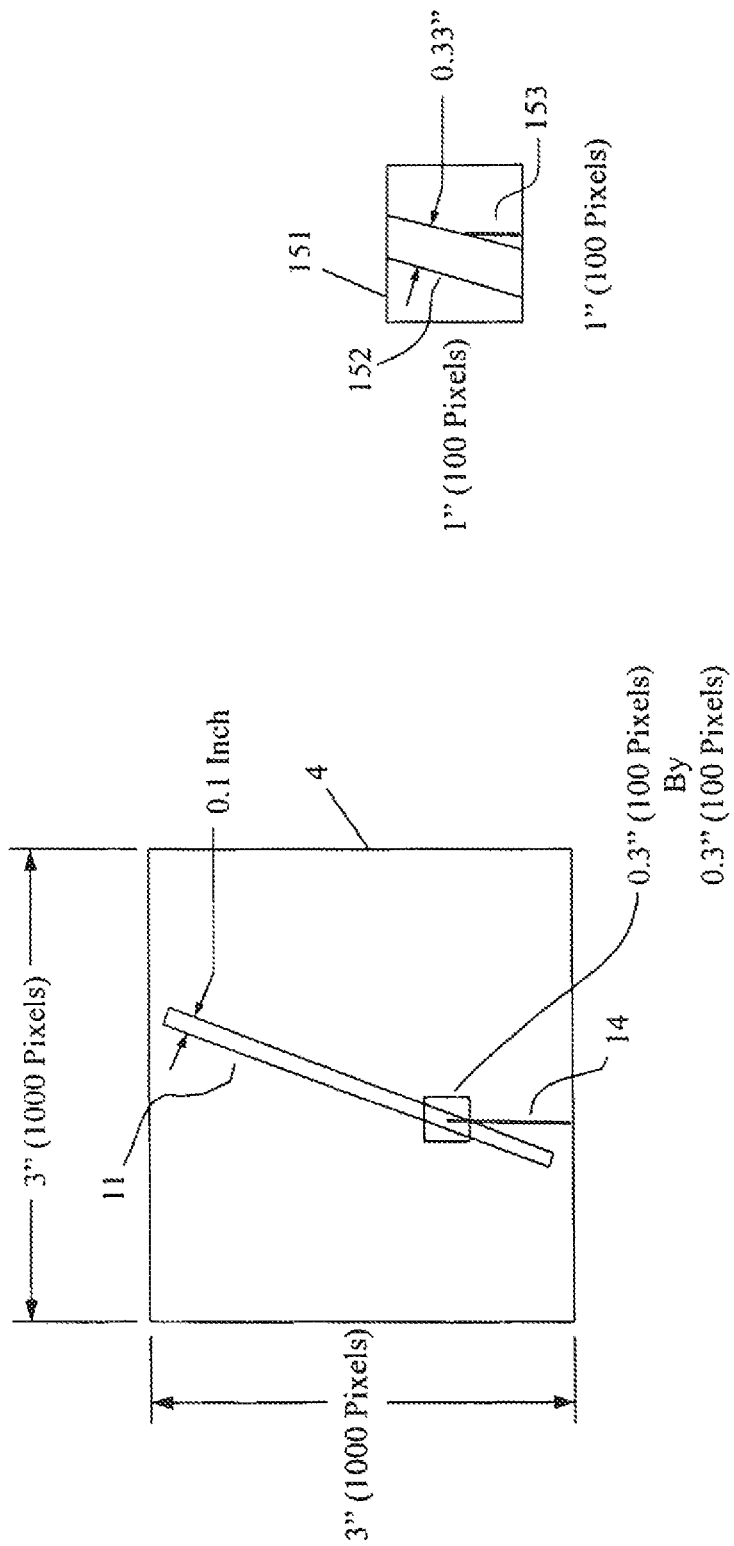

MICRO VEIN ENHANCER WITH A DUAL BUFFER MODE OF OPERATION

CROSS REFERENCE TO RELATED APPLICATIONS

This application is a continuation of U.S. application Ser. No. 14/197,573, filed Mar. 5, 2014, which is a continuation of U.S. application Ser. No. 12/931,151, filed Jan. 25, 2011, now issued as U.S. Pat. No. 8,712,498, which is a division of U.S. application Ser. No. 11/478,322, filed Jun. 29, 2006, now issued as U.S. Pat. No. 8,478,386, which claims priority from previously filed provisional application Ser. No. 60/757,704, entitled "Micro Vein Enhancer," filed on Jan. 10, 2006, all disclosures of which are hereby incorporated by reference.

FIELD OF INVENTION

A miniature laser based vein contrast enhancer that can fit into portable hand held products that a practitioner can carry in their pocket.

BACKGROUND OF THE INVENTION

It is known in the art to use an apparatus to enhance the visual appearance of the veins in a patient to facilitate insertion of needles into the veins. An example of such a system is described in U.S. Pat. Nos. 5,969,754 and 6,556,858 incorporated herein by reference as well as a publication entitled "The Clinical Evaluation of Vein Contrast Enhancement". Luminetx is currently marketing such a device under the name "Veinviewer Imaging System" and information related thereto is available on its website, which is incorporated herein by reference.

The Luminetx Vein Contrast Enhancer (hereinafter referred to as LVCE) utilizes an infrared light source for flooding the region to be enhanced with infrared light generated by an array of LEDs. A CCD imager is then used to capture an image of the infrared light reflected off the patient. The resulting captured image is then projected by a visible light projector onto the patient in a position closely aligned with the image capture system. Given that the CCD imager and the image projector are both two dimensional, and do not occupy the same point in space, it is relatively difficult to design and build a system that closely aligns the captured image and the projected image.

A further characteristic of the LVCE is that both the imaging CCD and the projector have fixed focal lengths. Accordingly, the patient must be at a relatively fixed distance relative to the LVCE. This necessitates that the LVCE be positioned at a fixed distance from the region of the patient to be enhanced.

The combination of the size of the LVCE and the fixed focal arrangement precludes using the LVCE as small portable units that are hand held.

SUMMARY OF INVENTION

Finding a vein, necessary for administering intravenous solutions, drips and the like, can often be difficult. During venous penetration, whether for an injection or drip, it is essential to stick a vein in exactly the right location. If a practitioner is only slightly off center, the needle will more then likely just roll off.

The present invention is a Miniature Vein Enhancer that includes a Miniature Projection Head and a mounting means for the Miniature Projection head. The Miniature Projection Head of the present invention implements a polarized laser light. This diminishes the effects of specular reflection off the surface of the skin. The Veinviewer Imaging System, produced by Luminetx, uses a polarized filter to polarize the LED light. This polarized LED light is then rotated 90° in front of the camera, thus causing increased power loss. In addition, the IR and visible lasers in the present invention are modulated to allow a regular photodiode to detect the different signals from each wavelength separately. Furthermore, the IR laser power of the present invention is dynamically altered during each scan line, thus increasing the working range of the photodiode, and allowing for constant DC gain.

The miniature vein enhancer of the present invention may be used by a practitioner to locate a vein, particularly useful when trying to locate a vein in the very old or very young. More then fifty percent of attempts to find a vein in old people, who have a generally high percentage of loose, fatty tissue, and children, who have a generally high percentage of small veins and "puppy fat" are unsuccessful. The present invention is aimed at reducing and/or preventing the discomfort and delay associated with botched attempts to pierce veins for injections and blood tests. In addition, the present invention can cut the time it takes to set up potentially life-saving intravenous drip.

OBJECTS OF THE INVENTION

It is an object of the present invention to make a Miniature Vein Enhancer that is cost effective to manufacture.

It is another object of the present invention to make a Miniature Vein Enhancer that will allow a practitioner pinpoint a vein for intravenous drip, blood tests, and the like.

It is still another object of the present invention to make a Miniature Vein Enhancer that will reduce and/or diminish the amount of botched attempts to pierce a vein.

It is still a further object of the present invention to make a Miniature Vein Enhancer that is easy to operate.

It is another object of the present invention to make a Miniature Vein Enhancer that may be disposed of after use.

It is yet another object of the present invention to make a Miniature Vein Enhancer that may be hand held.

It is still another object of the invention to make a Miniature Vein Enhancer that implements a Miniature Projection Head in Alternating frame mode.

It is yet another object of the present invention to make a Miniature Vein Enhancer that implements a Miniature Projection Head that operates in Dual Buffer Mode.

It is yet another object of the present invention to make a Miniature Vein Enhancer that implements a Miniature Projection Head that operates in Real Time Mode.

BRIEF DESCRIPTION OF THE DRAWINGS

FIG. 1 is a representation showing the use of the miniature vein enhancer of the present invention on a patient.

FIG. 2A shows a side view of the top cavity section removed from the body of the miniature vein enhancer of FIG. 1.

FIG. 2B shows a side view of the body of the miniature vein enhancer of FIG. 1.

FIG. 2C shows a side view of the body with the top cavity section removed.

FIG. 2D shows a side view of the body with the left and right wall pivoting about their respective pivot points.

FIG. 2E is a rear view of the body with the top cavity section in place.

FIG. 2F is a side view of the body of FIG. 2E.

FIGS. 5A to 5C show an alternative mounting embodiment for an MVE.

FIGS. 11A to 11D show the MVE of the present invention removably mounted to a phlebotomist's chair.

FIGS. 12A-12B shows a prior art vial holder.

FIG. 13A shows an improved vial holder that has particular application to the present invention.

FIG. 13B is a side view of the MPH mounted to the improved vial holder depicted in FIG. 13A.

FIGS. 15a to 15d depict an embodiment of the present invention in which MVE has a disposable stand.

FIG. 17a is a perspective view of the MVE attached to a disposable mounting bracket.

FIG. 17b is a perspective view of the ring portion of the mounting bracket of the MVE depicted in FIG. 17a.

FIG. 17c is an exploded view of the MVE depicted in FIG. 17a.

FIG. 17d is a side view of the MVE depicted in FIG. 17a with a practitioner asserting a downward force.

FIG. 18a is a perspective view of the MVE attached to a disposable mounting bracket having a support ring.

FIG. 18b is a perspective view of the ring portion of the mounting bracket of the MVE depicted in FIG. 18a.

FIG. 18c is an exploded view of the MVE depicted in FIG. 18a.

FIG. 18d is a side view of the MVE depicted in FIG. 18a with a practitioner asserting a downward force.

FIG. 19a is a perspective view of the MVE attached to a disposable mounting bracket having a support ring that implements a support post.

FIG. 19b is a perspective view of the ring portion of the mounting bracket of the MVE depicted in FIG. 19a.

FIG. 19c is a side view of the MVE depicted in FIG. 19a with a practitioner asserting a downward force, after use, so as to cover the needle.

FIG. 19d is an exploded view of the MVE depicted in FIG. 19a.

FIG. 20b is a front view of the MVE depicted in FIG. 20a.

FIG. 21b is a perspective view of the MPH depicted in FIG. 21a.

FIG. 22a is an exploded view of the MVE with the MPH having a knurled cap for battery access.

FIG. 22b is a side view of the MVE depicted in FIG. 22a in a hand held version.

FIG. 22c is a side view of the MVE depicted in FIG. 22a with a screw on bezel.

FIG. 22d is front view of the holder of the MVE depicted in FIG. 22a.

FIG. 22e is a side view of the MVE depicted in FIG. 22a attached to the needle cover.

FIG. 23a is a side view of the MVE with a hexagonal body shape.

FIG. 23b is a front view of the holder of the MVE depicted in FIG. 23a.

FIG. 23c is a side view of the MVE depicted in FIG. 23a attached to the needle cover.

FIG. 23d is a side view of the MVE depicted in FIG. 23a with a string attached.

FIG. 24c is a side view of the MVE depicted in FIG. 24a with the MPH detached from the flashlight.

FIG. 24d is a bottom view of the MVE depicted in FIG. 24a with the MPH detached from the flashlight.

FIG. 24e is a side view of the MVE depicted in FIG. 24a being held in a practitioners hand.

FIG. 25b is a side view of the MVE depicted in FIG. 25a.

FIG. 25e is a side view of the top portion of the needle cover of the MVE depicted in FIG. 25a.

FIG. 26a is a perspective view of the MVE with a generally pear shaped battery holder.

FIG. 26b is a side view of the MVE depicted in FIG. 26a mounted to a needle cover.

FIG. 26c is an exploded view of the MVE depicted in FIG. 26a.

FIG. 26d is a perspective view of the MVE depicted in FIG. 26a being held in the hand of a practitioner.

FIG. 27a is a perspective view of the MVE with a generally rectangular battery holder.

FIG. 27b is a side view of the MVE depicted in FIG. 27a mounted to a needle cover.

FIGS. 28A and 28B represent the image of veins on the patient field of view.

DETAILED DESCRIPTION OF THE INVENTION

Figure 3A:
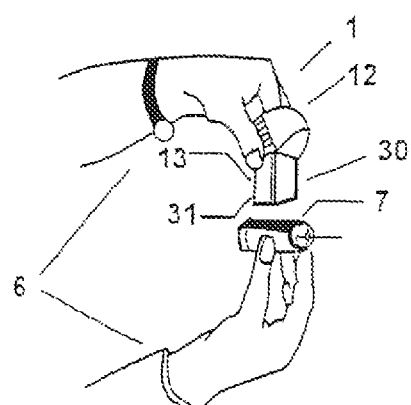
FIGS. 3A to 3F show an alternative embodiment of the miniature vein enhancer of the present invention where the top cavity section is fixedly attached to the body.

FIG. 1 shows a miniature vein enhancer (MVE) 1 for enhancing a target area 4 of a patient's arm 3. The MVE 1 has miniature projection head (MPH) 2 for both imaging the target area 4 and for projecting an enhanced image 11 along optical path 5 onto the target area 4. The MPH will be described in detail later with reference to FIG. 18-FIG. 21. The MPH 2 is housed in a cavity section preferably a top cavity section 12 of the MVE 1. The body 13 of the MVE 1 is positioned below the top cavity section 12. The body 13 has a vial opening 8 for receiving and temporarily holding in place a vial holder 7 having a needle 14. The body 13 also has a thumb opening 9 through which the medical practitioner 6 can place their thumb 10 while utilizing the MVE 1. The vial opening 8 is preferably provided with at least a curved base section 8A for receiving the curved exterior surface of the vial holder 7 and retaining it in position. The thumb opening 9 may be a separate orifice or it may be part of the vial opening 8.

The functioning of the MVE 1 of FIG. 1 follows. A medical practitioner 6 places a standard vial holder 7 into the vial opening 8. The vial opening 8 is shaped such that it snuggly holds the vial holder 7 in place. MVE 1 is preferably battery operated and is turned on by the practitioner 6 via an on/off switch not shown. Alternatively the unit can be turned on/off by a switch which detects the presence of the vial holder 7 in vial opening 8. The practitioner 6 places his thumb 10 though the thumb opening 9 and supports the bottom of the vial holder 7 with his forefinger. This mimics the normal grip that many practitioners use when grasping a vial holder for insertion into the veins of the patient. As the MVE 1 is brought close to the patients arm 3 the MPH 2 takes an image of the of the patient's 3 veins 11 within the target area 4. After receiving the image, the MPH projects along the optical path 5 onto the target area 4 a visible image of the veins.

The portable size of the MVE provides many advantages over the prior art units. The prior art units are too large to be held with a single hand, and in fact are fix mounted or mounted on rolling carts. This present invention is small enough to be portably carried by mobile workers, such as, doctors, nurses, emergency health workers, military personnel, police, and visiting home phlebotomists. The portable MVE can be moved quickly over the patient body thereby viewing a large number of veins in a short period of time. Further, the single handed operation of the MVE frees up the second hand of the care giver for other purposes.

FIG. 2A-2F illustrates in further detail the MVE 1 of FIG. 1. FIG. 2A shows the top cavity section 12 disconnected from the body 13. At least one but preferably two holes 15 for removably mounting the top cavity section 12 to the body 13 are situated on each side of the top cavity section 12. FIGS. 2B and 2C show the body from two different perspectives. The body has a protrusion 16 which are shaped to fit into the holes 15 on the top cavity section 12, thereby facilitating removable attachment of the body 13 to the top cavity section 12. It will be appreciated by those skilled in the art that the orifices 15 could be in the body 13 and the protrusions 16 in the top cavity section 12. FIGS. 2C and 2D show the body 13 with the top cavity section 12 removed. A cross member 18 connects to the left wall 20 and right wall 21 at pivot points 17. When release buttons 19 are squeezed together the bottoms of the left 20 and right walls 21 move apart increasing the size of the vial opening 8, thereby releasing a pressure hold on the vial holder 7 (not shown). When the top cavity 12 is inserted back into the body 8, the top cavity 12 applies an outward force at the tops of the left wall. 20 and right wall 21 thereby reducing the size of the vial opening 8, thereby insuring a snug connection between the vial holder 7 and the body 13. Similarly, inward pressure on the left wall 20 and right wall 21 at the bottom thereof applies an outward force at the tops of the left wall 20 and right wall 21 permitting easy insertion of the top cavity section 12 between the left and right wall on the body.

Further detail of the body 13 is shown in FIG. 2E and FIG. 2F. FIG. 2E is a rear view of the body 13 and FIG. 2E is a side view of the body 13. The removable top cavity section 12 snaps into place in the body 13 and is held in place by protrusions 16 which insert into the holes 15 (not shown in FIGS. 2E and 2F). The protrusions 16 disengage from the holes 15 when the left 20 and right walls 21 are pressed towards each other.

FIG. 3A-3F shows another embodiment of the present invention. FIGS. 3A-3F also shows an illustrative sequence of using the MVE. In FIG. 3A the MVE 1 is similar to that of FIG. 2A-2F except that it has a top cavity section 12 which is fixedly attached to the body 13. The bottom portion of the body 13 has two sides 30 and 31 extending downward with an opening on the bottom for receiving the vial holder 7. The two sides 30 and 31 are normally biased so as to form a tight friction fit around the vial holder 7, but the vial holder can be loosened by depressing simultaneously at points on the body under the thumb and index finger of the practitioner's left hand as shown in FIG. 3A to allow easy attachment between the vial holder 7 and the MVE 1.

The first step of operation is shown in FIG. 3A wherein the practitioner 6 holds the body 13 of the MVE 1 and squeezes (between the thumb and index finger) to release the bias of the two sides 30 and 31. The practitioner 6 then takes a new vial holder 7, positions it in between the two sides 30 and 31 and releases the pressure between the thumb and index finger thereby allowing the sides to move towards their normally biased position around the vial holder 7. The MVE 1 is now removably attached to the vial holder 7. Alternatively, where the vial holder 7 is made of a flexible material, the thumb and index finger may squeeze the vial holder 7 to release it from the body.

Figure 3B:
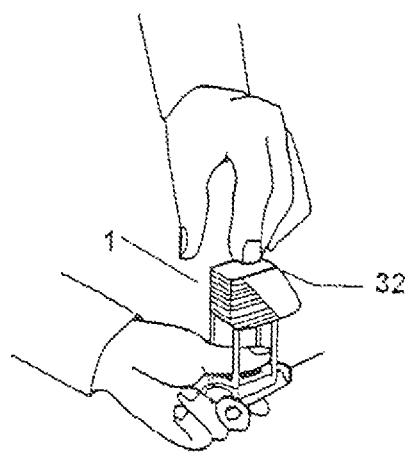

The second step of operation is shown in FIG. 3B wherein the practitioner activates the MPH 2 (not shown in these figures) contained within the head of the top cavity section 12. FIG. 3B shows this activation being performed by depressing a button 32 on the top of the MVE 1, or alternatively, the unit can automatically initiate when the MVE is attached to the vial holder 7.

Figure 3C:
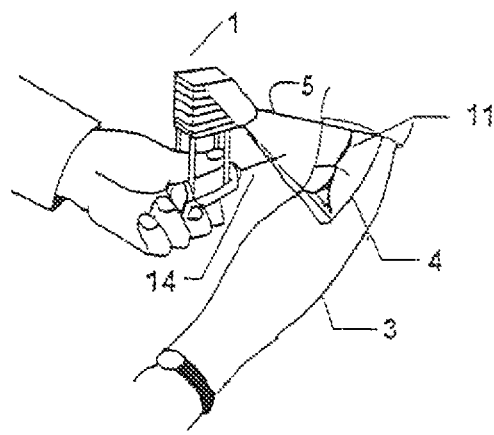

FIG. 3C shows the practitioner 6 approaching the arm of a patient 3 with the MVE 1. The optical path 5 and the field of view 4 of the MVE 1 are shown in FIG. 3C. At this time the veins 11 of the patients 3 arm are visually projected from the MPH 2 onto the patients arm. A significant advantage of the MPH 2 used in a handheld configuration is the fact that the image at the field of view 4 is always in focus, regardless of the distance from the MPH 2 to the patient 3. Since the distance between the MPH 2 and the patient is constantly decreasing as the MVE 1 approaches the patient 3, the prior art systems, which have limited fields of view, would not work property in such an embodiment. It should be further noted that the practitioner only needs at this time to utilize one hand to manipulate the vial holder 7 as well as support the MVE 1. This leaves available the second hand for other tasks.

It should be further noted that the point of the needle 14 is within the optical path 5 of the MPH 2. Accordingly, the practitioner can move the MVE 1 over the patient's arm 3 viewing the entire vein structure of the patient. When the practitioner wants to approach a particular vein with the needle 14, the vein remains within the field of view even as the needle is brought down the surface of the patient. The prior art systems had imagers and projectors which were fixedly mounted, and therefore to view large areas of the patients body either the entire projector had to be move relative to the patient, or the patient had to be moved relative to the projector.

Figure 3D:
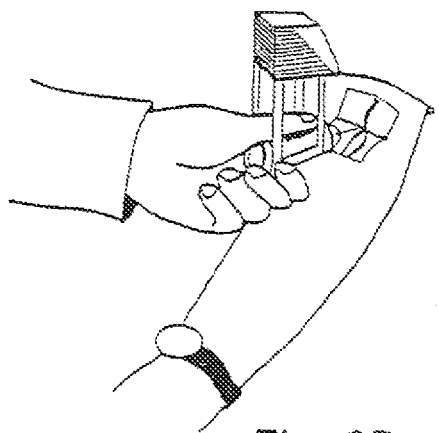

FIG. 3D show the practitioner inserting the needle 14 of the MVE 1 into the patient's vein 11. It should be noted that throughout steps 3C and 3D only a single hand of the practitioner is required.

Figure 3E:
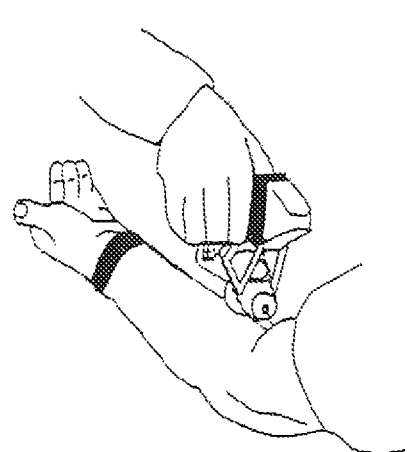

FIG. 3E shows the practitioner 6 initiating removal of the MVE 1 from the vial holder 7 by squeezing between his thumb and index finger the top portions of side walls 30 and 31, thereby reducing the pressure upon the vial holder 7.

Figure 3F:
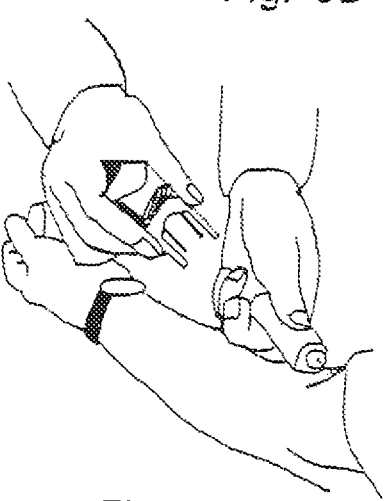

FIG. 3F shows the MVE 1 being removed from the vial holder 7. The MVE 1 can then be set aside for future use. The practitioner at this point can perform all task normally performed after the vial holder is inserted into a patient's veins.

The embodiment of FIGS. 3A-3F utilized a standard cylindrical vial holder 7 and relied on pressure between the side arms 30 and 31 to hold the vial holder in place. Accordingly existing standard vial holders 7 can be utilized. It will be appreciated by those skilled in the art that vial holders having a different cross section than cylindrical can also be used by modifying the inside surface of the side arms.

Figure 4A:
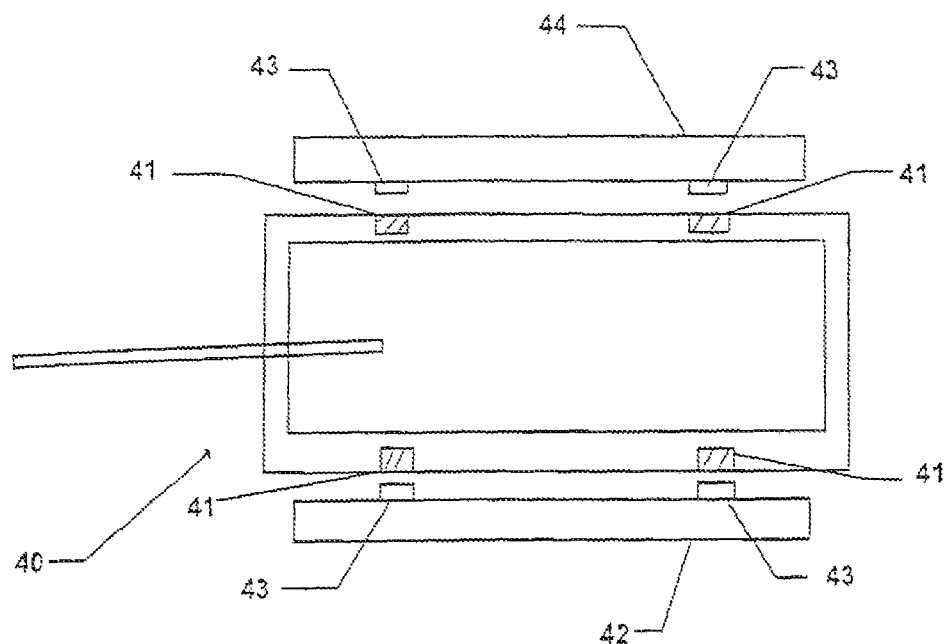
FIGS. 4A and 4B show an alternative vial holder used with the present invention.

It, however, might be desirable to utilize a new type of vial holder which has features that allow it to attach more rigidly to the MVE 1. FIG. 4A illustrates a top view such a new vial holder 40 and the side arms 42 and 44 of a MVE. The vial holder 40 has four indentations 41, two on one side of the cylindrical body and two directly opposite. The side arms 42 and 44 of the MVE have four protrusions 43 that are slightly smaller in size than the indentations 41. When the side arms 42 and 44 are moved towards the vial holder 40 the protrusions 43 insert into the indentations 41 and the vial holder 40 is thereby prevented from moving in relationship to the MVE.

Figure 4B:
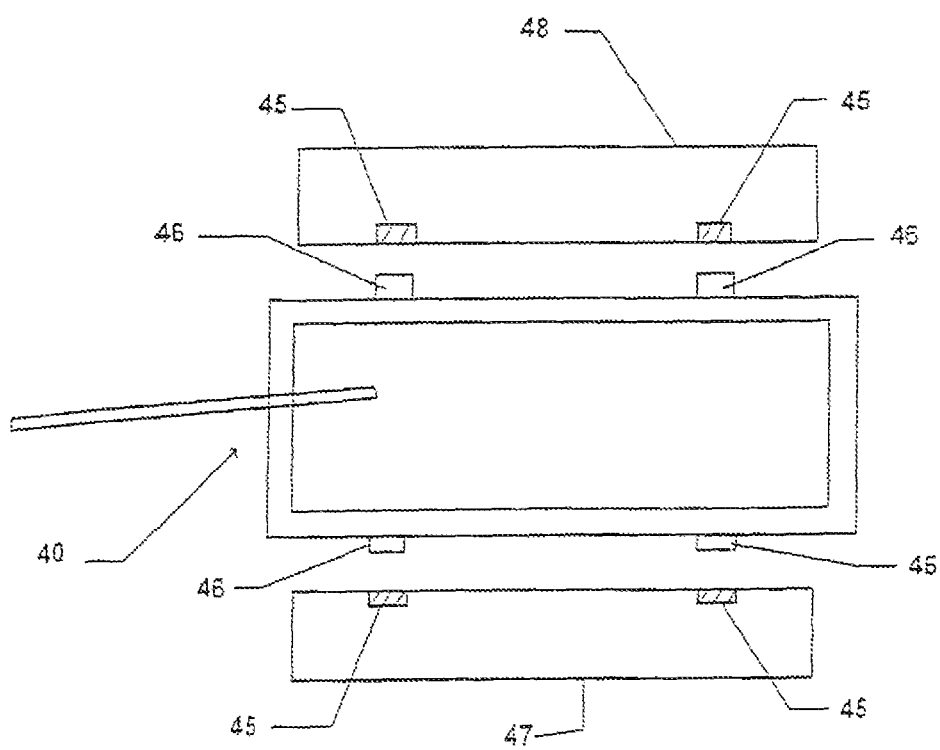

As a yet further mounting embodiment is shown in FIG. 4B, the side arms 47 and 48 can be curved to form the rounded vial opening 8 of FIG. 1. Further the arms are configured with indentations 45, two on each side arm, which are positioned to receive protrusions 46 which are incorporated into the vial holder 40 of this embodiment. Accordingly, when a vial holder with protrusions as shown in FIG. 4B is utilized, the locking mechanism between the MVE and the vial is strong due to the mating of the protrusions 46 and the indentations 45. Alternatively, when an existing vial holder 7 shown in FIG. 1 is used (without the protrusions), the unit will function as described in FIG. 1 and the pressure from the curved side arms 47 and 48 against the vial holder 7 will hold the MVE and the vial holder together. The indentations 45 in this case simply will not be used. Accordingly, the an MVE having the side arms shown in this FIG. 4B can be utilized with existing vial holders or can be use with the new vial holder shown in FIG. 4B.

While FIGS. 4A and 4B illustrates mounting arrangements between vial holders and a MVE, the present invention is not limited thereto. Many other types of removable mounting arrangements can be considered, such as, for example, the detachable mounting arrangement utilized between razors and razor blades.

Manufactures of the MVE which utilize the new vial holder of FIG. 4A and FIG. 4B will be able to sell a system which contains a single MVE as well as multiple disposable vial holders 40. Further, a consumable business for disposable vial holders as shown in FIGS. 4A and 4B can be established.

Figure 5A:
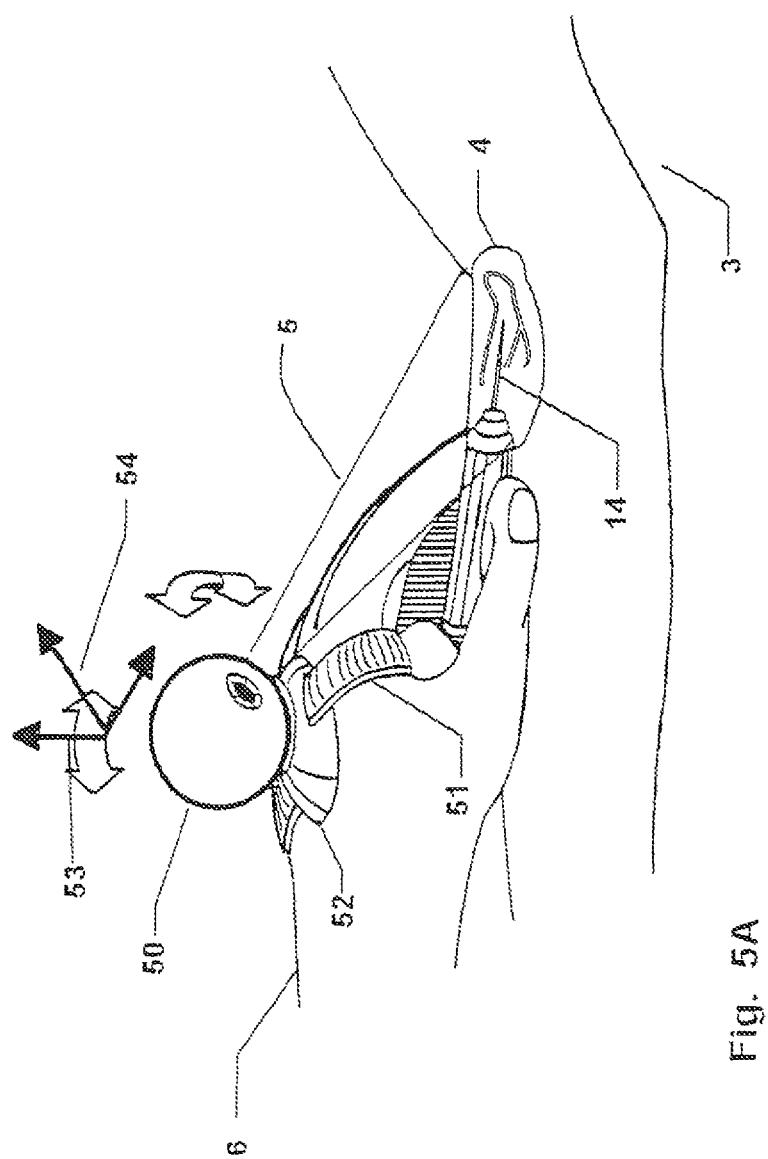

FIG. 5A-FIG. 5C shows various views of an alternative mounting embodiment for an MVE. In this embodiment the MVE 50 is connected to a strap 51. In one embodiment the MVE 50 may be connected to a mounting plate 52 which in turn is strapped with strap 51 to the back of the hand of the practitioner 6. Preferably, the MVE 50 is rotatably mounted on the mounting plate 52. The connection rotatable between the MVE 50 and the mounting plate 52 allows the MVE 50 to be rotated about a first axis 53 perpendicular to the back surface of the users hand and also rotate about a second axis 54 horizontal to the hand. The MPH 2 (not shown) is housed within the MVE and projects along optical path 5 to field of view 4 (in the same manner as described earlier with reference to FIG. 1). By rotating the MVE 50 on the mounting plate 52 the practitioner can aim the optical path 5 so that the field of view 4 is positioned around the point of the needle 14. FIG. 5B shows a top view of the MVE 50 of this embodiment. FIG. 5C shows the bottom of the practitioners 6 hand. The strap 51 can be attached by Velcro 55 or a snap button or other suitable means to enable the practitioner to easily attach and detach the MVE 50.

Figures 6A, 6B:
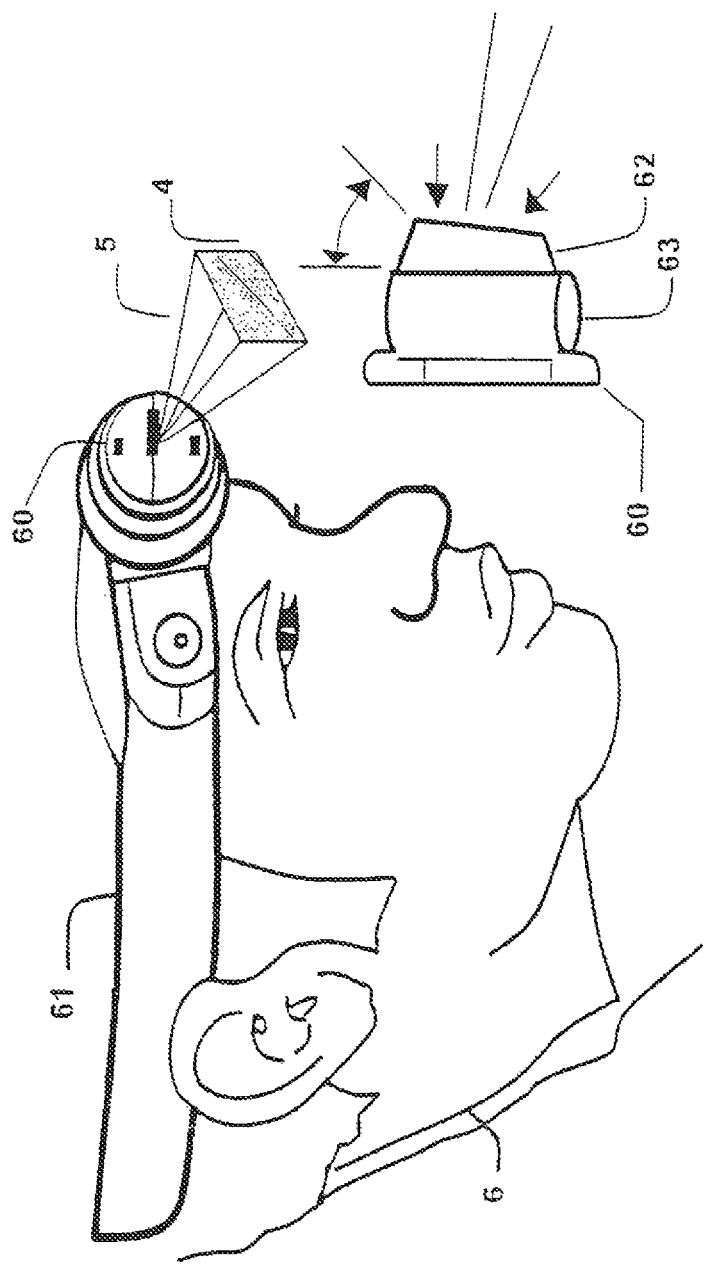
FIGS. 6A and 6B show an alternative embodiment of the MVE of the present invention.

FIG. 6A shows yet another alternative mounting embodiment for an MVE. In this embodiment the MVE 60 is connected to strap 61 which goes around the head of the practitioner 6. The MPH 2 (not shown) is housed within the MVE 60 and projects along optical path 5 to field of view 4 (in the same manner as described earlier with reference to FIG. 1). The practitioner 6 can easily move the optical path 5 by moving his head, thereby placing the field of view 4 anywhere desired on the patient. Provided the MVE 60 is positioned so that the optical path 5 substantially corresponds with the line of site of the practitioner 6 when looking forward, the placement of the field of view 4 on the patient will be very natural to the practitioner 4. The strap 61 can be attached by Velcro (not shown) or other suitable means to enable the practitioner to easily attach and detach the MVE 60.

FIG. 6B shows in more detail the MVE 60 of FIG. 6A. The MPH 2 (not shown) is housed in an adjustable housing 62 which is movably connected to a base 63. In this embodiment, the relationship between the adjustable housing 62 and the base 63 may be that of a ball and socket. The adjustable housing 62 is preferably round and the base 63 is a corresponding concave socket. The practitioner can rotate the adjustable housing 62 within the base 63 to change the direction of the optical path 5 relative to the head of the practitioner. In this manner, the mounting of the MVE 60 to the head can be less precise, and optimization of the direction of the optical path 5 is adjusted by moving the adjustable housing 62 within the base 63. This embodiment leaves both hands of the practitioner completely unencumbered while allowing the field of view 4 of the image on the patent to be easily moved by simple head movements of the practitioner.

Figure 7:
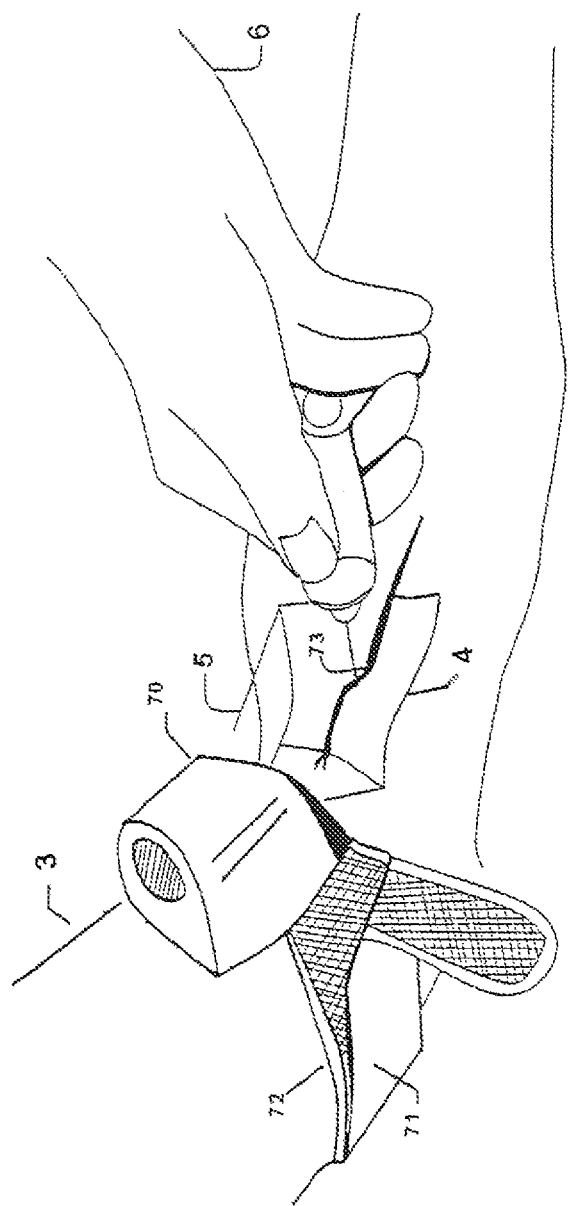
FIG. 7 shows a still further embodiment of the MVE of the present invention that is particularly useful for accessing veins in the arms of patients.

FIG. 7 shows yet another embodiment of the MVE which is particularly well suited for accessing the veins in the arm of a patient 3. In current practice, tourniquets are often placed around the bicep of the arm so as to enlarge the veins of the arm and make them easier to insert needles into. In this embodiment the MVE 70 is mounted onto a tourniquet 71 which gets placed around the bicep of the patient 3. The tourniquet 71 can be tightened around the bicep and held tight by e.g., Velcro scraps 72. When tightened around the arm 3, the MVE 70 is oriented such that the optical path 5 from the MPH (not shown) housed within the MVE 70 is directed towards the target veins 73 on the arm. In this manner, the MVE is held in place and the Practitioner 6 has both hands available for use.

Figure 8:
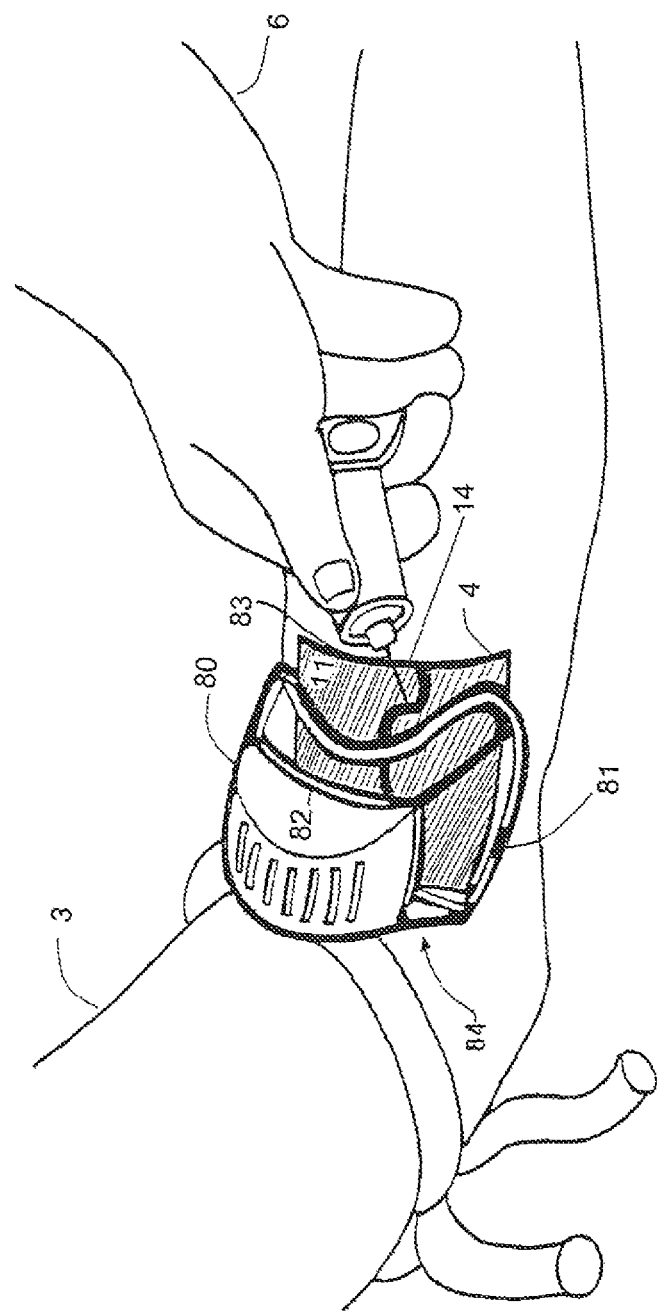
FIG. 8 shows an embodiment of the invention where the MVE is mounted on a base.

FIG. 8 shows another embodiment of the MVE. In this embodiment, the MVE 80 is mounted on a generally clear plastic or glass base 81 which can be placed by the practitioner 6 on the arm of the patient 3. The base 81 has a curved bottom 82 which conforms roughly to the shape of the arm of the patient 6. Provided the patient 3 does not drastically move their arm, the MVE 80 will remain in place without requiring the practitioner to hold the MVE 80. If desired, the base may be provided with openings on sides 83 and 84 near the area where the base contact the patient's arm to receive a strap or other means to secure the MVE to the arm without unnecessarily blocking the view of the veins. The MPH (not shown) is housed within the MVE 80 and is oriented so that the optical path is downward from the MVE to the arm resulting in the field of view 4 falling on the patient's arm. The curved bottom 82 is also curved concavely inwards so as to provide unobstructed access to the veins of the patient with needle 14. In this embodiment, the base 81 needs to be relatively transparent to permit the visual image of the veins projected from the MPH (not shown) within the MVE 80 to pass from the arm of the patient 6 through the base 81 to the viewer. One advantage of this embodiment is that, because the MVE 80 is portable, it can be quickly positioned on patient's arm 3, and can quickly be removed after use and placed on the side while the practitioner 6 continues their work.

Figure 9:
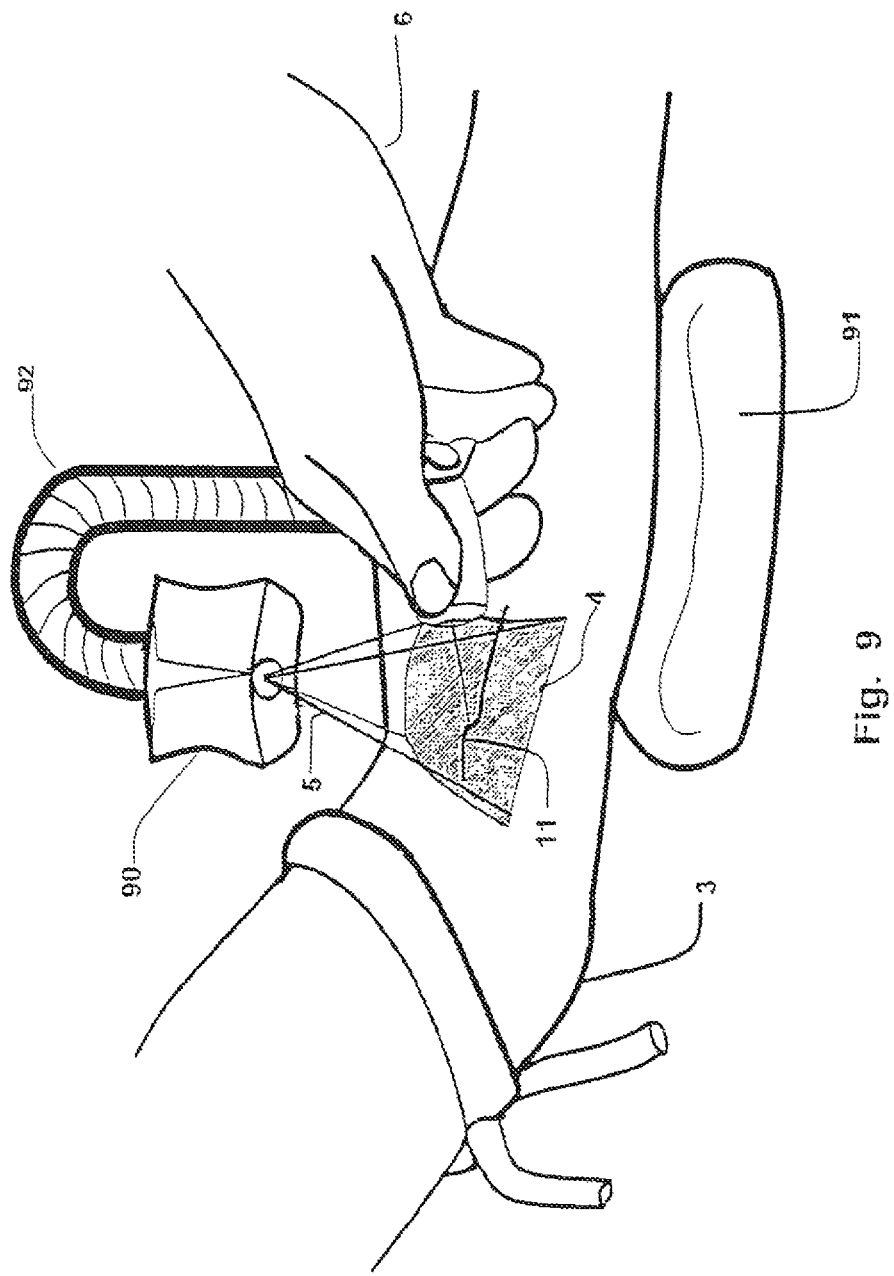
FIG. 9 shows an MVE on a base with a flexible "gooseneck" arm.

FIG. 9 shows an embodiment of the MVE wherein the MVE 90 is mounted on an adjustable arm 92 which connects on one end to the MVE 90 and at the other end to a base 91. The arm 92 in this embodiment is shown as a gooseneck type arm, however other arrangements are possible. The base is shaped so that it can comfortably support the patient's 3 arm. The gooseneck arm 92 is such it can be moved and rotated by the practitioner 6, but after such movement or rotation, it maintains its set position. Gooseneck type arms are well known in the art and need not be described further herein. The MPH 2 (not shown) is housed within the MVE 90 and projects along optical path 5 to field of view 4. The operation of FIG. 9 will now be described.

The patient 3 places their arm on the base 91 with the elbow facing down. The practitioner 6 turns on the MVE 90 via a switch (not shown). Alternatively the MVE 90 can turn on automatically when a pressure sensor (not shown) in the base 91 detects the presence of an arm positioned thereon. The practitioner 6 then moves and rotates the MVE 90 until the field of view 4 falls on the desired veins 11, the field of view 4 remains in a fixed position upon the patient's arm. The practitioner may then release the MVE 90, and then go about accessing the vein 11.

Figure 10:
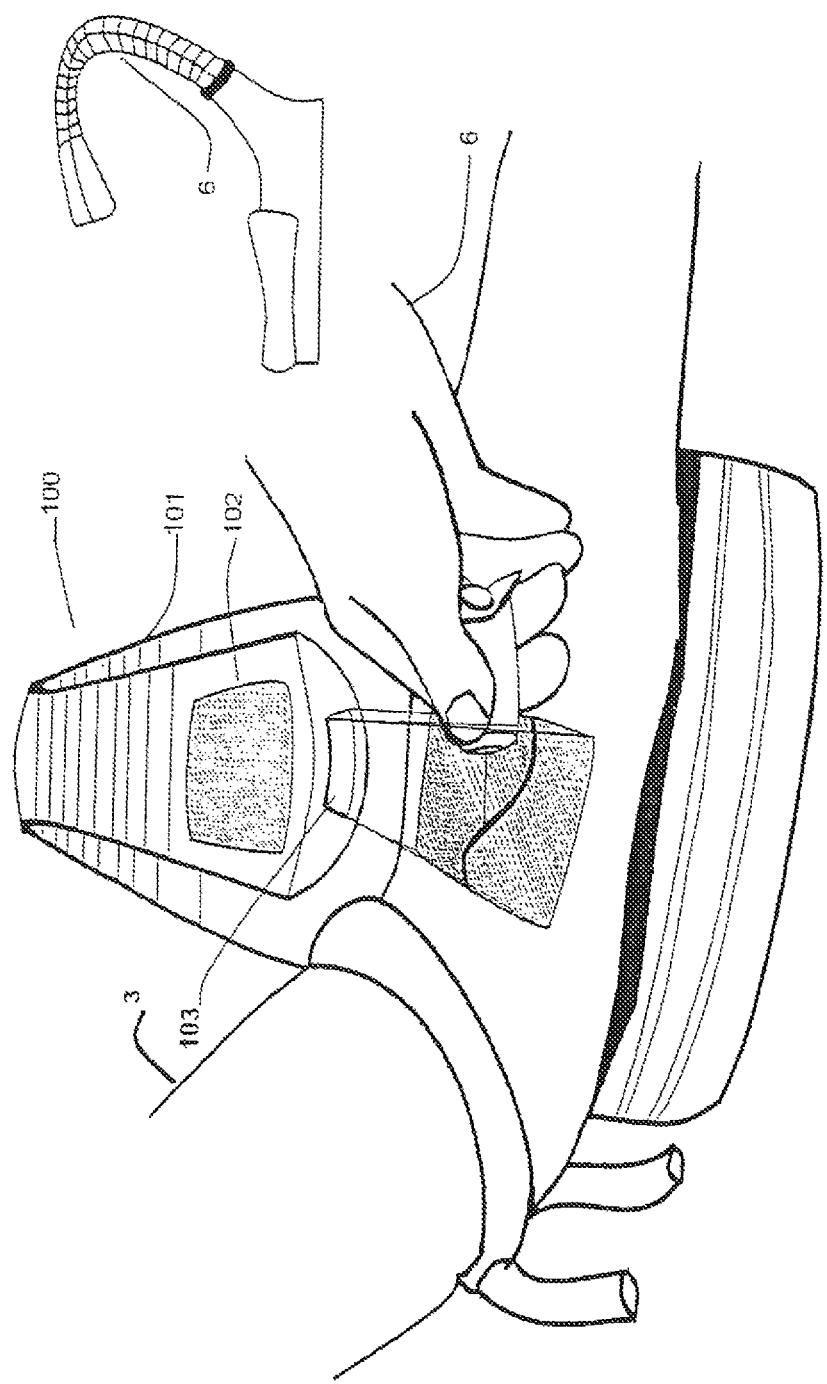
FIG. 10 shows an MVE with an alternative type of gooseneck.
Figure 13C:
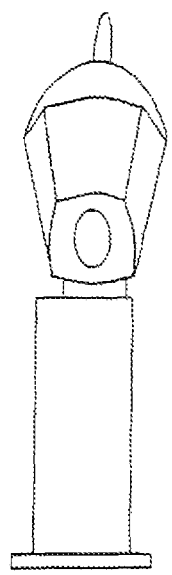
FIG. 13C is a top view of the MPH mounted to the improved vial holder depicted in FIG. 13A in a scale of 1:1.
Figure 13D:
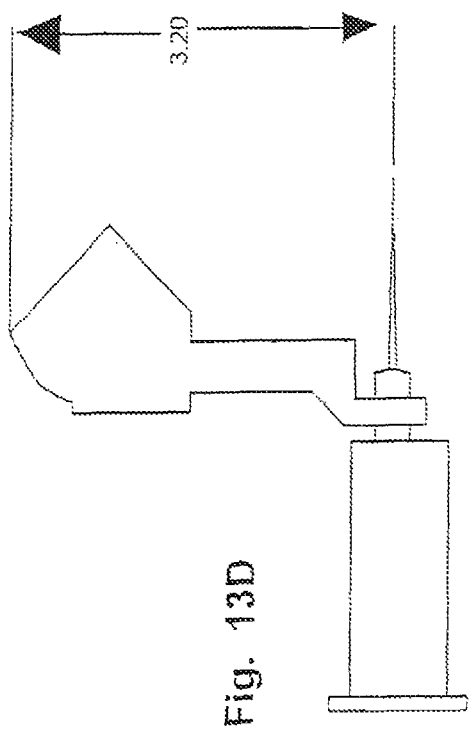
FIG. 13D is a side view of the MPH mounted to the improved vial holder depicted in FIG. 13A in a scale of 1:1.
Figure 13E:
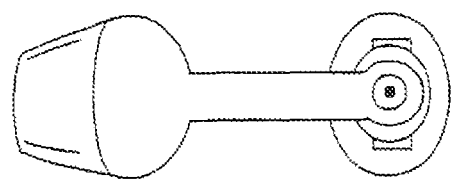
FIG. 13E is a front view of the MPH mounted to the improved vial holder depicted in FIG. 13A in a scale of 1:1.

FIG. 10 shows an embodiment that is similar to that of FIG. 9 except that the supporting mechanism 101 is much wider and can support a larger weight. The MPH is housed in the MVE 100 at a position so that the optical path of the MPH exits through an opening 103. Further, the embodiment of FIG. 10 includes a touch display 102, through which the practitioner can adjust parameters of the MPH (not shown), such as for example, the brightness, contrast and the projection angle of the MPH.

FIGS. 11A-11D show an embodiment wherein the MVE 111 removably mounts to an existing phlebotomist's chair 110 having a armrest 112 upon which a patient can rest their arm while the practitioner is accessing their vein. The MPH (not shown) is mounted in the top portion 113 and projects along optical path 5 to field of view 4 which is positioned on the armrest 112. The top portion 113 mounts to bottom portion 114 in such a manner that the top portion 113 can slide up and down relative to the bottom portion 114, thereby increasing and decreasing the distance from the MPH to the armrest 112. As the distance increases the field of view 4 grows larger but the brightness at a given location within the field of view 4 decreases. Conversely, as the distance decreases the field of view 4 shrinks but the brightness at a given location within the field of view 4 increases.

FIGS. 11C and 11D show in greater detail an example of how the MVE 111 can be attached to the armrest 112 of the chair 110. The bottom portion has a "C" like structure 115 that can be placed over the armrest 112. A screw mechanism 116 can be turned to attach the MVE 111 to the armrest 112. One skilled in the art will appreciate that there are other types of means for securing the MVE 111 to the armrest 112.

FIG. 12B shows a prior art vial holder 123 with a prior art needle protector 120 connected. When a practitioner is finished with the vial holder 123, prior to disposal, the practitioner uses an available surface to push the needle protector 120 down over the needle 124, thereby preventing accidental needle pricks. The needle protector has a main body 121 and a circular mounting ring 122 which fits directly over the front of the prior art vial holder 123. FIG. 12A shows the prior art needle protector 120 disconnected from the vial holder 123.

FIGS. 13A-13E shows a needle holder 125 in accordance with the present invention that is capable of supporting a MVE. The needle holder 125 has a main body 126 and a circular mounting ring 127 which fits directly over the front of a prior art vial holder 123. Additionally, the needle holder also has a thumb support 128 at the base of the needle holder 125.

FIG. 13B shows the needle holder 125 of FIG. 13A connected to a prior art vial holder 123 and a MVE 131 temporarily connected to the needle holder 125. A MVE 131 has a main body portion 130 which houses the MPH 2. The main body portion 130 is rotationally connected to a stem portion 129 in such a manner that the main body portion 130 can be rotated by a practitioner thereby rotating the optical path 5 up or down. The connection between the stem portion 129 and the main body portion 130 is stiff enough that after the practitioner moves main body portion 130 up or down, it remains in that position even after the practitioner releases the main body portion 130. The stem portion 129 of the MVE 131 has an opening at the bottom that is shaped to receive the top of the main body 126 of the needle protector 125. When the stem portion 129 of the MVE 131 is placed over the top of the main body 126 of the needle protector 125 and slight pressure is applied between the two, the two pieces temporarily snap together. The locking mechanism is designed so that stem portion 129 can rotate while snapped to the top of the main body 126. The fitting between the two is tight enough so that after the stem portion 129 is rotated by the practitioner, no further rotation occurs unless and until the practitioner again rotates the stem portion 129.

When the needle protector 125 is attached to the vial holder 123, a thumb support 128 is in contact with the vial holder 123. When using the vial holder with the MVE 131 attached, a practitioner would position their thumb on top of the thumb support 128 and their index finger on the opposite side of the vial (across from the thumb support). In this manner, the practitioner is supporting in a single hand the vial holder 123, the needle protector 125 and the MVE 131. The practitioner can move the main body portion 130 of the MVE so that the optical path 5 is aligned so that the field of view includes the point of the needle. After the practitioner inserts the vial holder 123 needle into the vein of the patient, the MVE 131 can be detached from the needle protector and placed down on a surface. At this point in the process, the blood can be withdrawn in the same manner as the prior art system of FIG. 12B. Upon completion of activity, the vial holder 123 and the needle protector 125 can be disposed of.

Figure 14A:
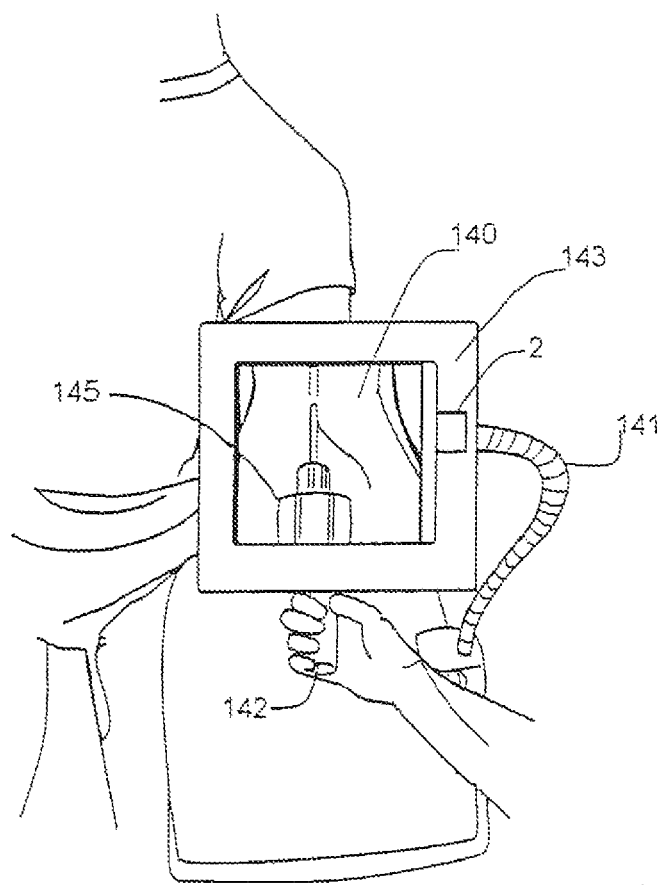
FIGS. 14A to 14B depict an embodiment of the present invention in which the MVE is integrated into a magnifying glass housing.
Figure 14B:
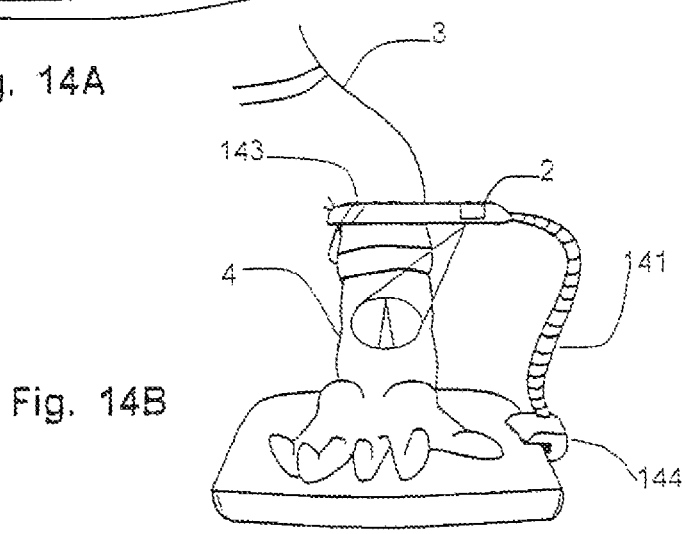

FIGS. 14A and 14B show an embodiment wherein the MPH 2 is integrated into a magnifying glass housing 143 which supports a magnifying glass 140. The magnifying glass housing 143 connects, for example via a gooseneck or other type support 141 to a clamp 144 which in turn can mount to a table, the arm of a phlebotomist chair or other suitable support. The MPH 2 is positioned within the magnifying glass housing 143 such that the optical path 5 is aimed downward towards the table or arm of the chair. When a patient 3 places their arm on the table the field of view 4 falls upon the arm. As shown in FIG. 14A, when the practitioner looks through the magnifying glass 140, an enlarged image 145 of the vial holder 142 and the veins of the patient 3 within the field of view 4 of the patient is provided. Viewing the enlarged image permits greater accuracy in inserting the vial holder into the veins of the patient.

As a yet further embodiment, the magnifying glass 142 of FIGS. 14A and 14B can be replaced with a flat panel display. In this case the MPH 2 only has to capture the image of the veins and the needle of the vial holder 142 within the field of view 4 and does not have to retransmit a visible image onto the arm. Instead, the visible image of the veins and the needle is transmitted onto the flat panel display 142 which is viewed by the practitioner as he inserts the needle into the vein. In this embodiment, the practitioner is not directly viewing the needle or the arm but instead is viewing an image thereof in the flat panel display 142. The image in the flat panel can digitally be enlarged or reduced (zooming) as required by the practitioner. The controls for such zooming can be via touch screen input onto the flat panel display.

Figure 14C:
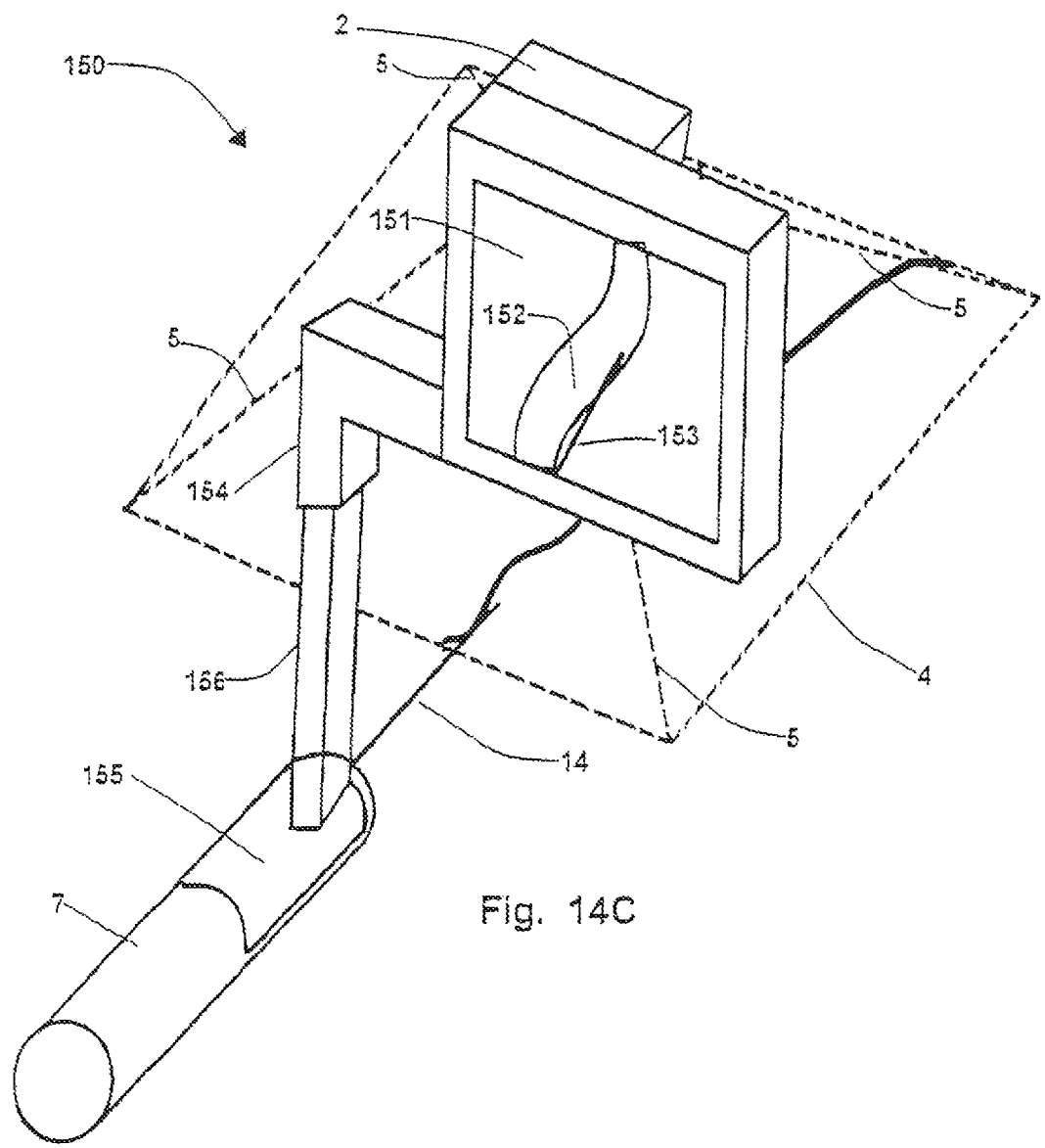
FIG. 14C is a rear view of another embodiment of the present invention with a display used to view the image of the miniature vein enhancer.
Figure 14D:
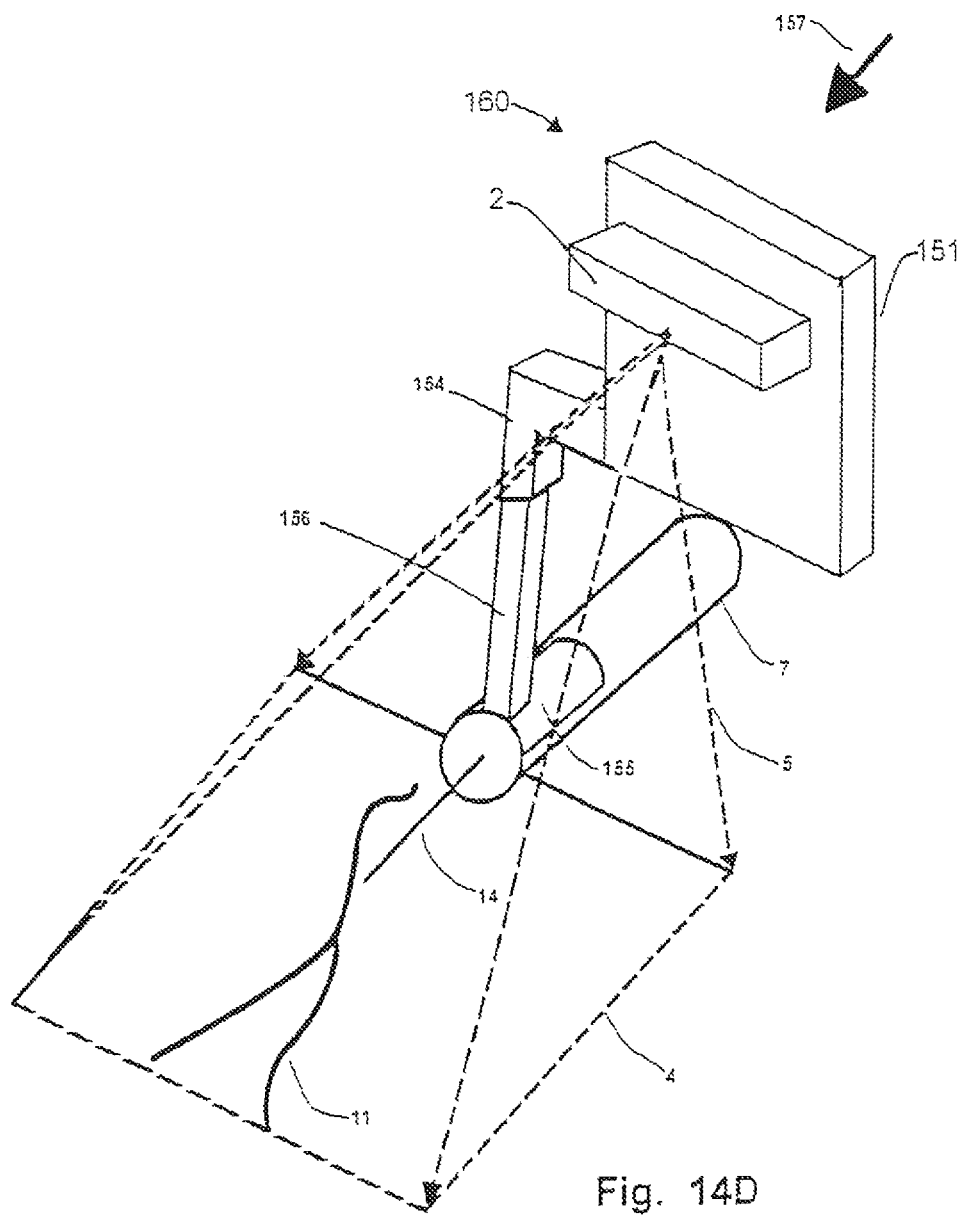
FIG. 14D is a front view of the embodiment depicted in FIG. 14C.

FIGS. 14C and 14D show two perspectives of yet another embodiment of an MVE 150. In this embodiment the MVE 150 includes a small display 151, which is viewed along viewing angle 157 by the practitioner, having attached thereto an attachment piece 154 and a MPH 2. Although the attachment is shown at a right angle to the stem extending vertically from the vial, the stem can be at an angle to the vial and the display angle can vary, as well. A needle protector 156, similar to that shown in detail in FIG. 13A connects to a vial holder 7. The attachment piece 154 receives the top of the needle protector and temporarily locks the MVE to the needle protector 156 which in turn attaches to the vial holder 7. The MPH 2 is attached to the small display 151 and is oriented so that the optical path 5 is such that the field of view 4 covers the point of the needle 14. The MPH 2 outputs the image of the veins 11 onto the field of view 4 on the patient (not shown). The MPH 2 also provides the image signal to the display 151 to be viewed on the display 151. The image signal includes both the veins and the needle 14. The display 151 includes image processing capabilities that detects the position of the tip of the needle and displays a predetermined number of pixels of the image around the tip of the needle on the display. In FIG. 14C, both the image of the needle 153 and the image of the vein 152 are shown.

An example of using the MVE 150 of FIG. 14C follows. A practitioner selects a disposable sterile vial holder 155 which has the needle protector 156 attached thereto. The needle protector 156 is moved to right angle position relative to the needle 14, thereby exposing the needle. The MVE 150 is connected via the attachment piece 154 to the top of the needle protector 156. The MVE is then turned on and the MPH 2 receives the image of the veins 11 and the needle 14 within the field of view 4. The practitioner would move the MVE 150 about the patient viewing the image of the veins 11 projected onto the patient. The image of the veins will be the actual size and position of the patient's veins. When a vein is selected for puncture with the needle, the practitioner will bring the needle towards the vein while still viewing the image of the veins on the patient body. When the practitioner gets close to the selected vein with the point of the needle, the practitioner will look at the display 151 image which is an enlarged image of the point of the needle 153 and the target vein 152. By using this enlarged image, the practitioner can be certain to puncture the center of the vein 11 with the needle 14.

The display 151 can be very small given that all it has to do is show the amplified view of a single vein and the needle. By way of example, as shown in FIGS. 28A and 28B, wherein FIG. 28A represents the image of the veins 11 on the patient in the field of view 4, and FIG. 28B represents the image of the vein 152 and the image of the needle 153 displayed on the display 151. In this example, the target vein is 0.10 inch across and the field of view 4 is 3" by 3", and the resolution of the image captured and projected by the MPH 2 in the field of view is 1000 pixels by 1000 pixels. In this example, the MVE is programmed to display on the display 151 a 300 pixel by 300 pixel area having the needle centered therein. Referring to FIG. 28B, the resulting amplified image of the vein 152 is shown at more than three times its original width. As can be appreciated, the amount of magnification (zoom amount) on the display 151 can be algorithmically adjusted by a processor in the display. Inputs can be provided for the practitioner to select the appropriate gain amount.

Figure 14E:
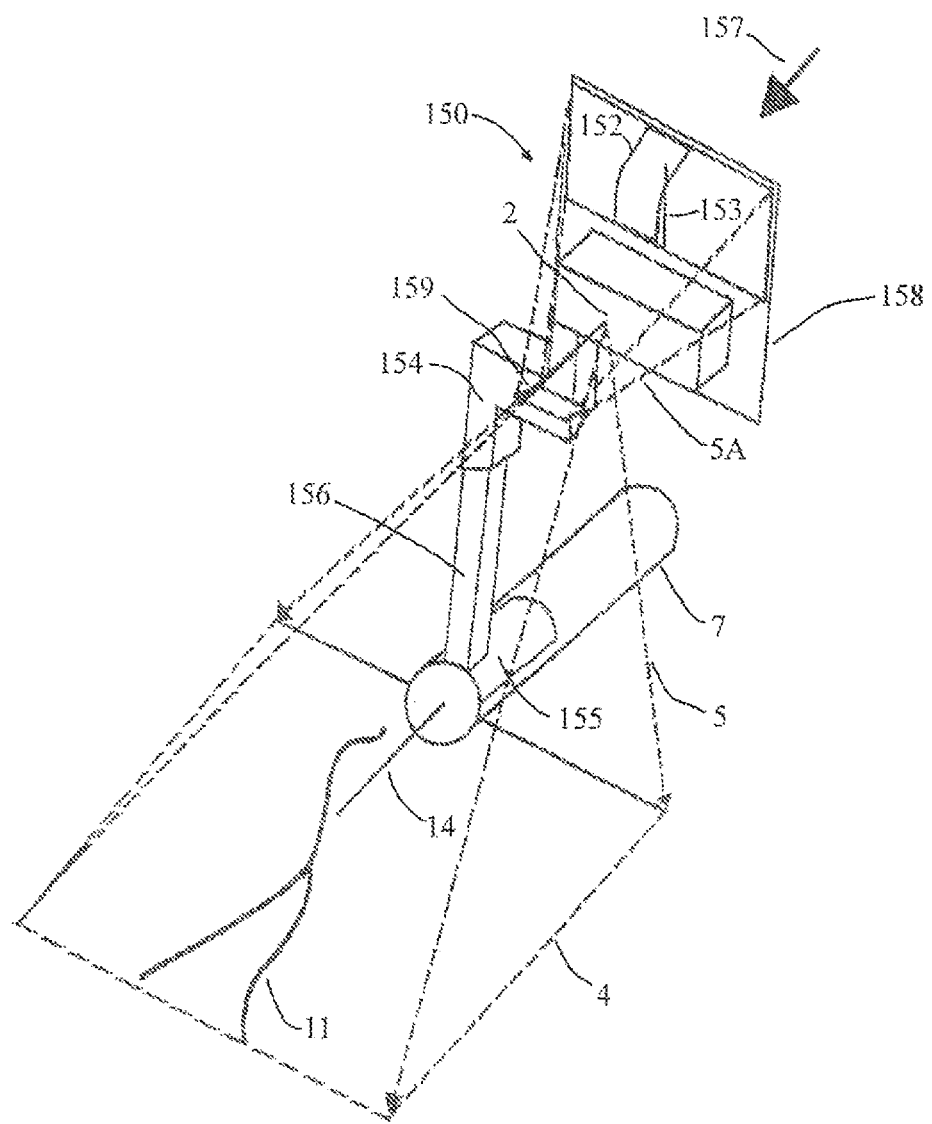
FIG. 14E is a front view of the embodiment depicted in FIG. 14C with the miniature projection head located on the lower portion of the display.

An alternative embodiment is shown in FIG. 14E wherein the display 151 of FIGS. 14C and 14D is replaced by a rear projection screen 158. The MPH can be configured to project a split image. The bottom half is the actual image representing the veins 11 and the top half is an image of the magnified image of the veins and needle. A mirror 159 is placed within the optical path 5 of the top half of the image projected by the MPH 2. The mirror 159 is angle so that the top half of the image is projected along optical path 5B to the rear projection screen 158. Rear projection screen is translucent and can be viewed by the practitioner along viewing angle 157. In this manner, a display screen is obtained without incurring the addition cost, size and power of the dedicated display of FIG. 14C and FIG. 14D.

In still another embodiment, as seen in FIGS. 15a-15d, the MVE may have a disposable stand 200, which may include a generally "C" shaped base clip portion 201. Base 201 may be constructed from the same materials as the previously mentioned embodiments. In the preferred embodiment MVE stand 200 can be molded from a clear plastic. Any suitable clear plastic known in the art including but not limited to PVC, Polystyrene, Acrylic and the like may be used. Extending from base 201 may be an arm 202, which has a concave bottom corner 203 and a convex top corner 204. Both corners may be integrally formed with base 201. Arm 202 may have an inside surface 205 and an outside surface 206. Located between top corner 204 and bottom corner 203 of arm 202 may be a second generally "C" shaped clip 209. Located at the top of MVE 200 may be a generally circular ring portion 207. Ring portion 207 may be an integral member of MVE stand 200 or ring 207 may be a separately attached member. In a preferred embodiment ring 207 was integrally formed with stand 200. In addition, ring 207 may have a generally circular threaded outer top surface, so as to act as a male end, or ring 207 may have a generally circular grooved inner surface, so as to act as a female end, a utility of which will now be discussed.

With the present embodiment MPH 208 will operate as in the previous discussed embodiments, however in the present embodiment MPH 208 may have either a threaded outside surface or a grooved inside surface, this will be a matter of preference. For example, if ring 207 has a threaded outside surface MPH 208 will have a corresponding grooved inside surface, this will give the practitioner the ability to attach and remove the MPH, before and after use, respectively. In normal operation the practitioner will snap clip 201 to prior art vial 220. In addition, the practitioner will snap clip 209 to prior art needle protector 221. After the clips 201 and 209 have been attached the practitioner may then attach MPH 208 to ring 207. This will be accomplished via the two previous attachment methods already discussed. It should be pointed out that the practitioner may also attach MPH 208 to ring 207 before attaching the rings to the vial.

Once the MVE is securely attached the practitioner may then continue with the procedure as previously discussed. After the procedure is complete the practitioner will then apply a pressure to surface 206 sufficient enough to push needle protector 221 and arm 202 over the used needle 223, after which the MPH may be removed for future use and the needle and MVE stand 200 may be discarded.

Figure 16A:
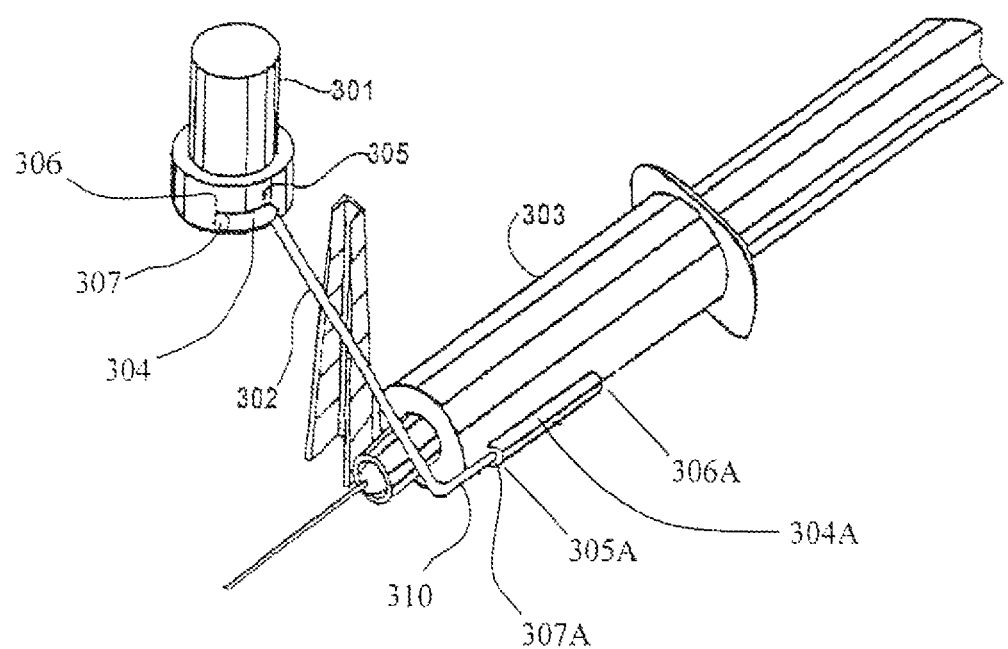
FIGS. 16a to 16c depict an embodiment of the present invention in which the MVE implements a different disposable type of stand.
Figure 16B:
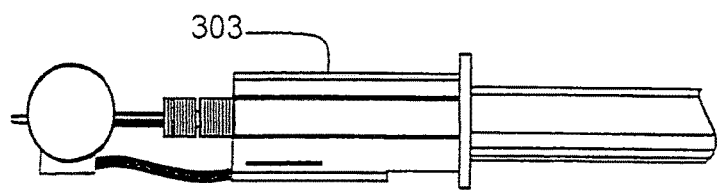
Figure 16C:
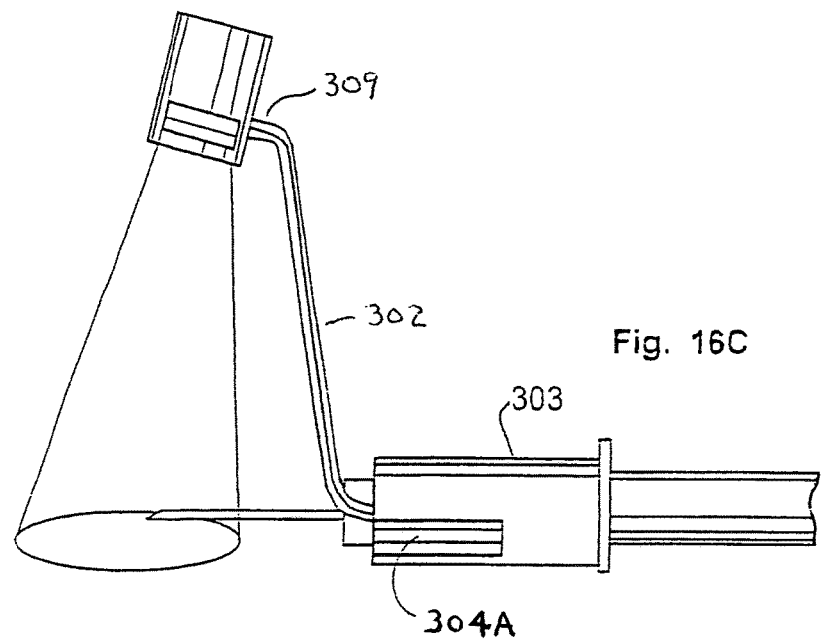

Another embodiment of a disposable MVE stand 302 may be seen in FIGS. 16a-16c. This type of embodiment may include a MPH 301, a stand 302 and a vial 303. MPH 301 may have the same operable features as previous mentioned MPHs. Stand 302 may be constructed of any suitable known material in the art including but not limited to metal, metal alloy, plastic, plastic composite, or the like. In a preferred embodiment stand 302 can be made of plastic. Plastic was preferred because of cost effectiveness and sanitary qualities. As mentioned above MPH 301 may operate as in the other previous mentioned embodiments, however unique to the present embodiment are carriages 304 and 304a located on MPH 301 and vial 303, respectively. Carriage 304 may be any suitable shape known in the art, in a preferred embodiment carriage 304 has a generally rectangular shape. In addition, carriage 304 may have an orifice 307 extending from a front end 305 to a rear end 306, or partially therethrough. In a preferred embodiment orifice 307 does not extend the entire length of carriage 304, as seen in FIG. 23a. Orifice 307 may have a diameter that is slightly smaller than holder portion 309 of stand 302. Stand 302 may have also have a keeper portion 310. It should be pointed out that keeper 310 and holder 309, as seen in FIGS. 23b and 23c, are generally the same shape and size as each other and in the preferred embodiment may be used interchangeably.

Located on at least one side of vial 303 may be another carriage 304a, as mentioned above. In a preferred embodiment carriage 304a may be generally the same size and shape as carriage 304. However, one may implement different sizes and shapes for any of the carriages and/or arms. Carriage 304a may also have an orifice 307a that extends from a front end 305a to rear end 306a, as in carriage 304. In the preferred embodiment both carriages have orifices that extend equally the same length. One difference between carriage 304 and 304a is that carriage 304 is slightly rounded, so as to conform to MPH 301. In another embodiment MPH may have a straight base, in which case carriage 304 may not be rounded. Carriages 304 and 304a may be located anywhere on MPH 301 and vial 303, respectively. In normal operation the practitioner may insert holder arm 309 into orifice 307 and keeper arm 310 into orifice 307a. Once inserted the practitioner may move the MVE to the desired position. Since the individual carriage orifices have smaller diameters than the respective arms that they receive, the relied upon pressure will keep the MPH from moving during the procedure.

Figure 24A:
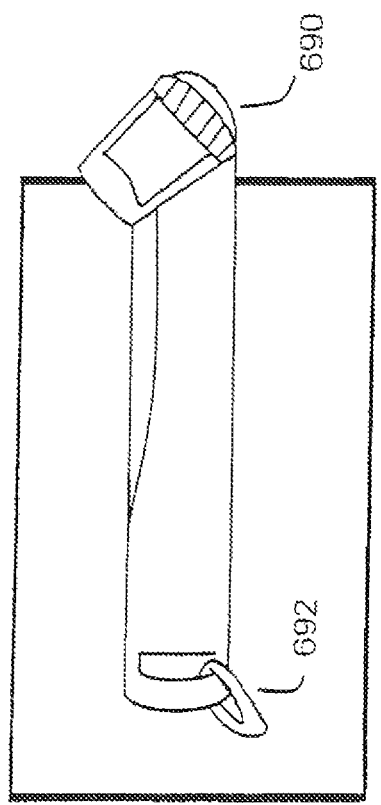
FIG. 24a is a side view of the MVE attached to a flashlight.
Figure 24B:
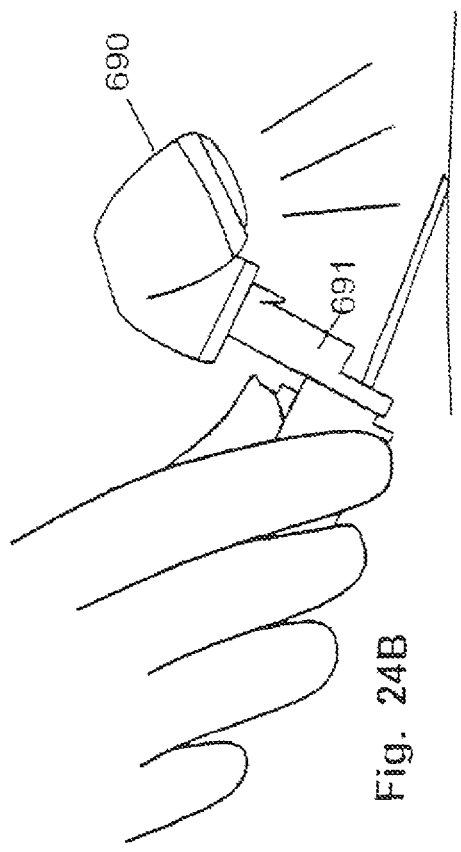
FIG. 24b is a perspective view of the MPH of the MVE depicted in FIG. 24a attached to a needle cover.
Figure 24I:
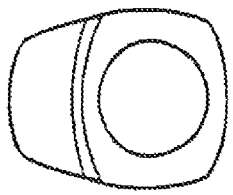
FIG. 24i is a front view of the MPH of the MVE in a scale of 1:1.
Figure 24G:
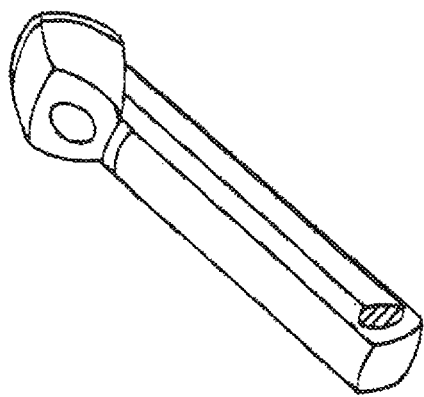
FIG. 24g is a perspective view of the MVE in a scale of 1:1.
Figure 24F:
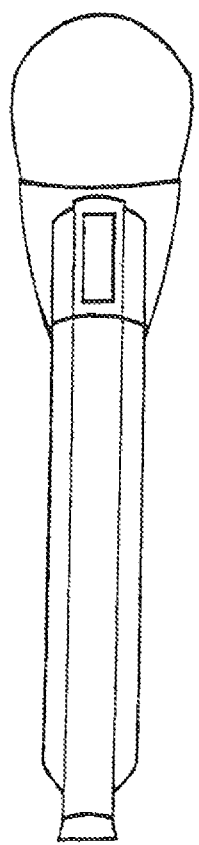
FIG. 24f is a bottom view of the MVE in a scale of 1:1.
Figure 24H:
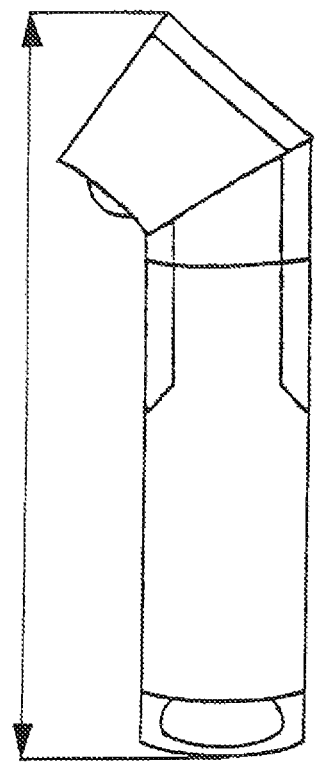
FIG. 24h is a side view of the MVE in a scale of 1:1.

Drawing ones attention now to the drawings labeled FIGS. 17a-17d is another embodiment of the present invention. In this embodiment, the MPH 401 operates in generally the same manner as the previous mentioned embodiments. A unique feature of this embodiment is the mounting bracket 400, which acts as a needle cover too: Mounting bracket 400 may included a mast portion 402 and a ring portion 403 that is hinged to mast 402. Ring portion 403 may be generally circular in shape with a front surface 404 and a rear surface 405. Also, ring portion 403 may have an orifice 406 that may extend from front surface 404 to rear surface 405, as seen in FIGS. 24a-24c.

Orifice 406 may be defined by inner circumferential wall 407. Orifice 406 of ring 403 may be sized to receive neck 408 of vial holder 409. In addition orifice 406 should have a diameter that will allow ring 403 to snap onto neck 408 of vial 409, this will allow the practitioner to attach bracket 400 before the procedure and dispose of bracket 400 after the procedure is performed, i.e. a disposable bracket. Ring 403 may also have a generally flat top surface 410. Flat top surface 410 may includes a break-away support diaphragm 411 that provides fore and aft stability, as seen in FIG. 17b. Also located on top surface 410 may be a living hinge 412, which provides side to side stability.

Hinge 412 may be any suitable type of hinge known in the art, in the preferred embodiment there can be a flexible plastic strip that connects ring 403 to mast 402. In addition, located on top surface 410 may be a locking mechanism that keeps mast 402 in an upright position when the practitioner is inserting the needle into the patient's arm and thereafter when the practitioner is drawing blood from the patient. As mentioned above, mast 402 may also act as a needle cover, and as such should be shaped and sized so as to be able to completely cover the needle 413 before and after use. Also mast 402 should be sized and shaped to be able to snuggly receive a bottom portion 414 of MPH 401. Mast 402 and ring 403 may be integrally formed or separately attached members. In the preferred embodiment mast 402 and ring 403 were integrally formed.

In normal operation the practitioner would snap ring 403 to neck 408 of vial 409. After ring 403 is securely attached to vial 409 the practitioner may lift mast 402 to an extended position so as to expose needle 413. Mast 402 will remain in a secured upright position via locking hinge 410. Once needle 413 is exposed the practitioner may then attach MPH 401 to mast 402. After MPH 401 is attached, the practitioner may then operate the MVE as in any of the previous embodiments.

For extra support there can also be a support ring 420 used for stabilizing mast 402 and MPH 401, as seen in FIGS. 18a-18b. In this embodiment support ring 420, may be defined as semi-circular, with a right arm 421 and a left arm 422 extending from a top area. Support ring 420 may also have an outer surface 423 that may extend from right arm 421 to left arm 422, and a inner surface 424 that also may extend from right arm 421 to left arm 422, as seen in FIG. 18c. Located on inner surface 424 of arms 421 and 422 may be two detents, 425 and 426 respectively. Detents 425 and 426 may be generally circular in shape and may extend from inner surface 424 to outer surface 425, so as to form two orifices, as in the present invention. Conversely, detents 425 and 426 may only extend partially into inner surface 424, so as to form two bored cavities.

As previously discussed MVE may also have a mast 427 and a ring 428, which may, as in a preferred embodiment, or may not be hinged to mast 427. In this embodiment support ring 420 pivotally attaches to mast 427, this may be achieved via two generally circular dimples 429 and 430 located on the outside surface 431 of mast 427. Detents 425 and 426 and dimples 429 and 430 may be centrally aligned along the same axis of rotation so as to allow for pivotal movement of mast 427. In normal operation the practitioner will snap on support ring 420 to neck 433, as in the previously discussed embodiment. The practitioner may then attach ring portion 428 to neck 433, after which, dimples 429 and 430 may be inserted into detents 425 and 426. Lastly MPH 401 may then be connected to mast 427. Once all members are attached the practitioner may then operate the MVE as in all previous embodiments.

In another embodiment, as depicted in FIGS. 19a-19d, vial 460 may have two generally cylindrical pegs, right peg 462 and left peg 463, located on its upper front surface just above neck 461. Peg 462 may have an outer and inner surface, 462a and 462b, respectively. Peg 463 may also have an outer and inner surface, 463a and 463b, respectively. Peg 462 may have an orifice 462c that extends from inner surface 462a to outer surface 462b, or orifice 462c may extend only partially into peg 462. Peg 463 may have a similar orifice. In this embodiment there can also be a mast 464 that may have a broader top portion 464a and a narrower bottom portion 464b. Top portion 464a may be generally the same size and shape as the previous mentioned embodiments, and as in all other embodiments top portion 464a has a slit that has a length equal to or greater than needle 413.

Figures 19A, 19B, 19C:
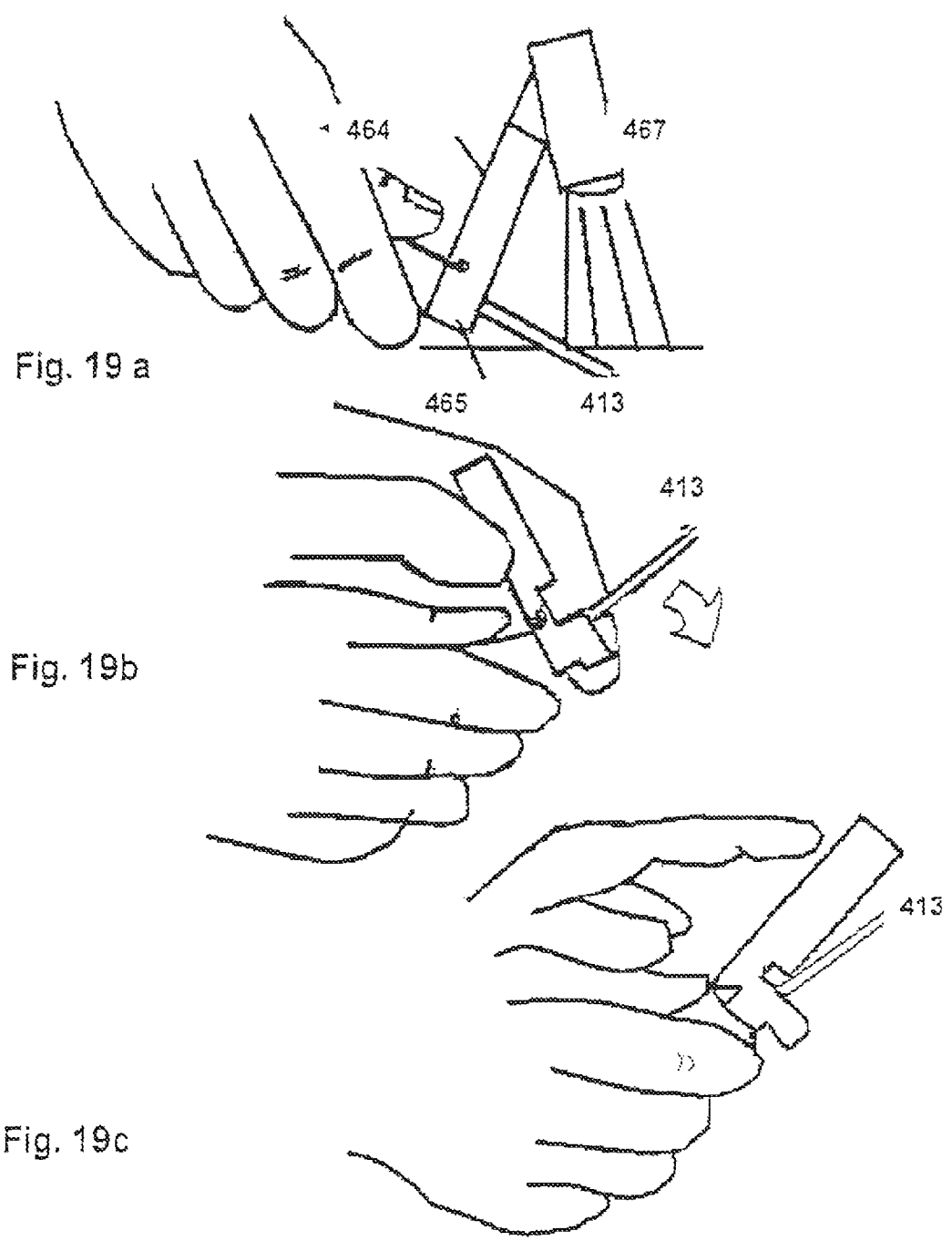

In the present embodiment a key feature of mast 464 is the generally cylindrical bottom member 464b. Located on the outer side surfaces of bottom portion 464b may be two dimples, 464c and 464d, which extend outwardly in a generally perpendicular direction. The present embodiment may also implement a support ring 465, as in the previously discussed embodiments, which may be used to stabilize mast 464 and MPH 467. Support ring 465 may be generally circular in shape with a diameter that is slightly larger than neck 461. This arrangement will allow for a snug fit and still allow support ring 465 to rotate a locked and unlocked position, seen in FIG. 19b. In addition support ring 465 may have at least one side bar 465b extending perpendicular from generally outer circumferential surface 465a. In a preferred embodiment there can be two side bars, 465a and 465b, extending perpendicularly generally circumferential outer surface 465a, as seen in FIG. 19d. Also, the preferred embodiment may have a support post 465d. Support post 465d may extend outwardly, preferably perpendicularly from outer surface 465a and may be located near the top of ring 465. Support post 465d may have a width that is equal to, less than, or greater than mast 464 preference. Located on the top portion of support post 465 may be platform 465e used to maintain mast 464 in an upright position. Support post 465 may have a length so as to allow support post 465 to fit snuggly under bottom surface 464f. In normal operation the practitioner may attach mast 464 to vial 460. Once mast 464 is attached, support ring 465 may then be snapped onto neck 461 of vial 460. At which time MPH may then be attached to mast 464 and support post 465e placed in a locked position. After the practitioner is finished performing the venous puncture procedure, the practitioner may then rotate support ring 465 to an unlocked position and place mast 464 over needle 413.

Figure 20A:
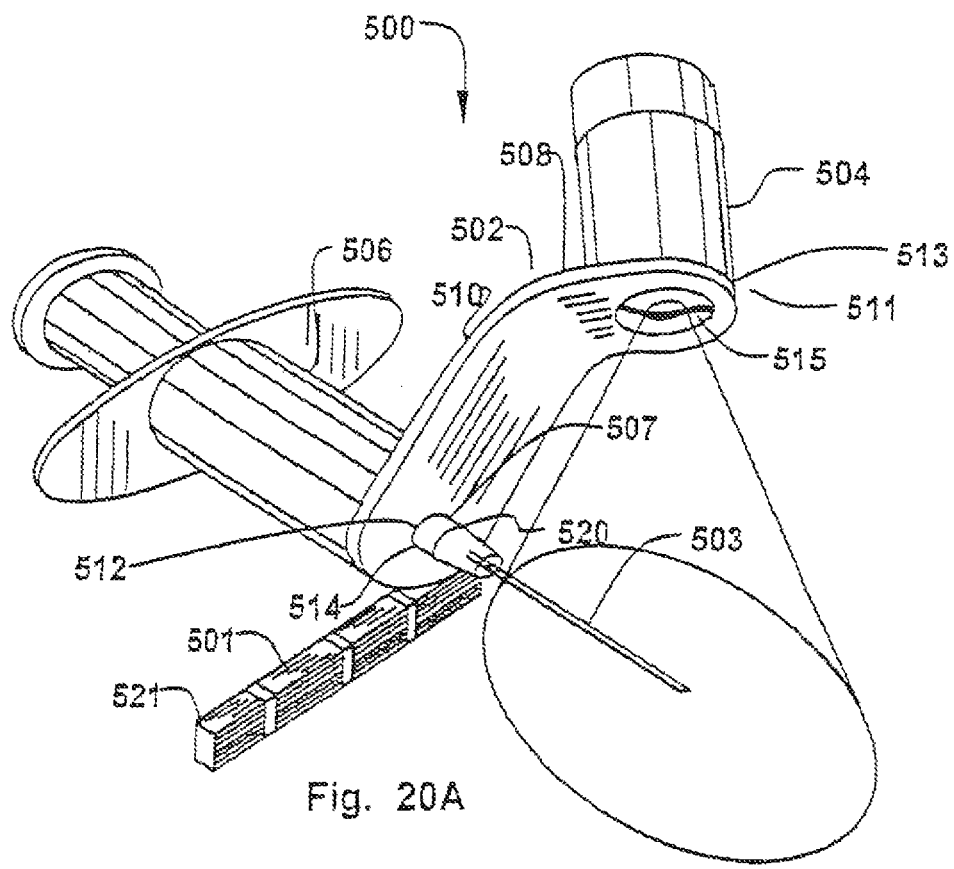
FIG. 20a perspective view of the MVE attached to a disposable syringe.
Figure 20B:
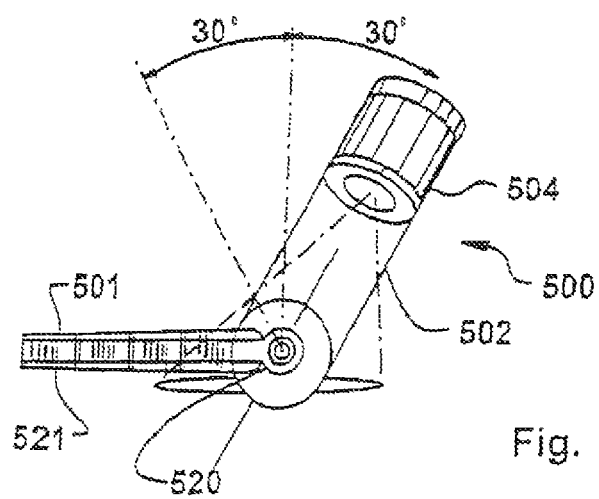

In still another embodiment as seen in the drawings labeled FIGS. 20a and 20b, the MVE 500 may include a needle protector 501, a mounting bracket 502, a needle 503 and a MPH 504. Needle cover 501 may be sized and shaped as in the other previous discussed embodiments. One key distinction however, is the placement of needle cover 501. In the present embodiment needle cover 501 may be placed on either the right or left side of vial 506. In the preferred embodiment needle cover 501 is located on the right side of vial 506, as seen in FIGS. 20a-20b. Needle cover 501 may have also have a bottom ring member 520 that is hinged to a top member 521. Ring 520 may have a diameter so as to allow the practitioner to press fit the needle protector over neck 507 of vial 506. Ring 520 may be hinged to top member as in the previous mentioned embodiments.

Another key distinction in the present embodiment is mounting bracket 502. Mounting bracket 502 may be constructed of any suitable material known in the art including, but not limited to metal, metal alloy and the like. In the preferred embodiment mounting bracket 502 was constructed from medium strength plastic. Mounting bracket 502 may be defined as having a top surface 508 and a bottom surface 509 connected by a generally circumferential sidewall 510, as seen in FIG. 20a. Mounting bracket 502 may have a generally "C" shape, with two orifices 513 and 514 located near a front end 511 and a rear end 512 respectively. Orifice 513 is generally circular in shape having a diameter sized so as to be able to receive a portion of MPH 504. In a preferred embodiment inner circumferential wall 515 may be designed so that MPH 504 may be secured to mounting bracket 502 by a press fit, or in another embodiment orifice 513 may have a threaded inner circumferential wall 515 so that a portion of MPH may be screwed to inner circumferential wall 515. In addition there can be a clear lens shield that can keep blood off of MPH 504. Orifice 514 may be sized and shaped so as to be able to receive neck 507 of vial 506.

Mounting bracket 502 may be press fitted to neck 507. This press fit allows the practitioner to rotate mounting bracket 502 30 degrees to the left or right, thus, if the practitioner should encounter any visual obstructions during the venous penetration and/or extraction, the practitioner may simply rotate mounting bracket 502: In another embodiment mounting bracket 502 may be integrally formed with vial 506, as in the preferred embodiment. In this embodiment mounting bracket may be designed to rotate in a similar manner as in the press fitted mounting bracket. In normal operation the practitioner may snap MPH 504 into orifice 515. Once MPH 504 is securely attached the practitioner may then rotate mounting bracket 502 up to 30° left or right, if needed. Also, the practitioner may attach needle cover 501 to neck 507. After the practitioner has performed the venous penetration and/or extraction, the practitioner may then place needle cover 501 over needle 503, remove MPH 504 from mounting bracket 502 and then dispose of syringe.

Figure 21B:
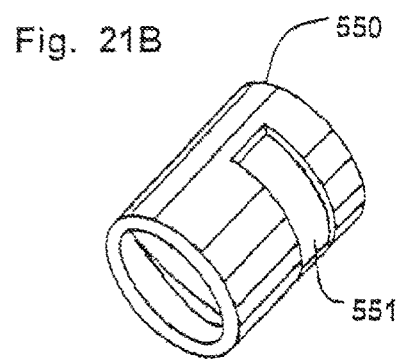
Figure 21A:
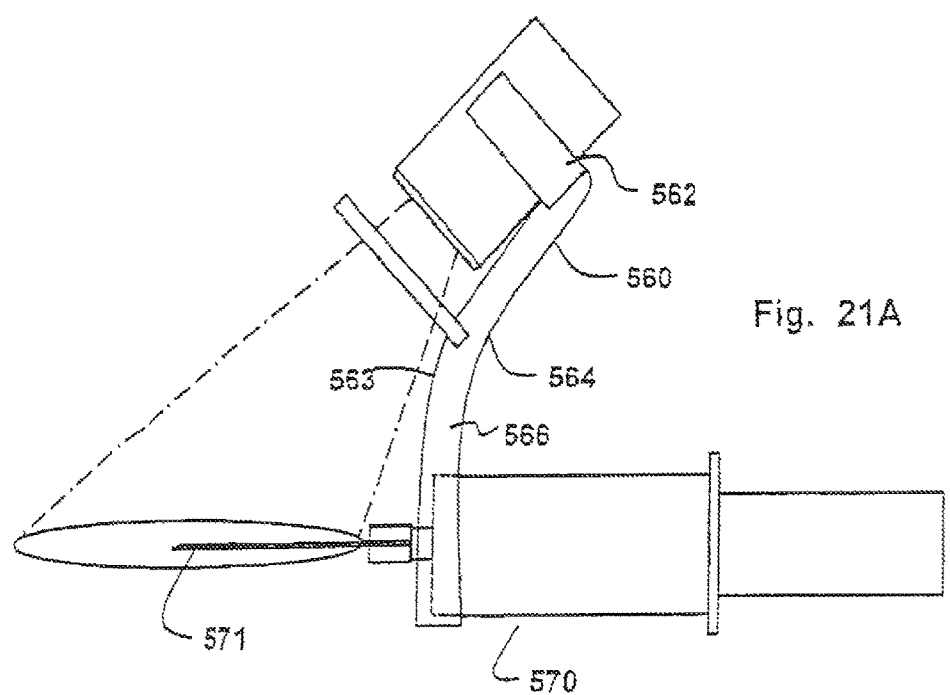
FIG. 21a is a side view of the MVE with a MPH bracket and disposable shield.

In another embodiment the MVE may include a MPH 550, bracket 560 and vial 570, as seen in FIG. 21*a*. This embodiment is similar to previous embodiments, however in this embodiment MPH 550 may have a mounting groove 551. Mounting groove 551 may be any suitable shape known in the art including but not limited to a square, rectangle and the like. In the preferred embodiment a generally rectangular groove was implemented. One could also have a mounting bracket with more then one groove. For example there can be two rectangular grooves. Mounting bracket 560 may be integrally formed with vial 570 or mounting bracket 560 may be a separately attached member. In a preferred embodiment, the mounting bracket was press fitted, which allowed the practitioner to dispose of the syringe after use. In another embodiment, mounting bracket 560 may be screwed on, and in another embodiment mounting bracket 560 may be bonded to vial 570, via any suitable bonding method known in the art. Mounting bracket 560 may have a generally upside down "L" shape, when looking at it from a side view, that is bent toward the bottom, as seen in FIG. 21*b*. Located near the top of bracket 560 may be two bracket fingers, left finger 561 and right finger 562. Fingers 561 and 562 have a generally "C" shape, when looking at them from the front, top, or bottom view. Fingers 561 and 562 are separated by a distance that will allow MPH 550 to be securely snapped into place. Mounting bracket 560 may also have front and rear surfaces, 563 and 564 respectively, connected by right and left sidewalls 565 and 566 respectively. Located on surface 563 may be groove 563*a*. Groove 563*a* may extend from right sidewall 565 to left sidewall 566, or partially therethrough. Groove 563*a* may be used to secure an optionally removable disposable shield. The needle 571 and needle cover 572 may be similar to the needle cover and needle of previous discussed embodiments.

Other embodiments of the present invention include hand held versions as seen in FIGS. 22-27. In these embodiments the MPH will operate in similar fashion as previously discussed. Also, in the hand held embodiments, there may be a main body that houses a first battery source, and a cavity in the MPH that houses a separate second battery source. With this configuration the first battery source may act as a charger for the second battery source, when connected, thus allowing the practitioner to remove and use the MPH from the main body when desired. Furthermore, there can be a separate AC charger, similar to that used with cell phones and the like, that can be used to charge any of the hand held versions of the present invention. In addition, the needle cover will also operate in similar fashion as previously discussed. The main distinctions between the previous discussed embodiments and the embodiments of FIGS. 22-27 are the mounting techniques and/or added attachments. For example, drawing one's attention to FIGS. 22*a*-22*e* is a MVE that implements a knurled cap 601, located on body 602 of MPH 600, for battery access. With this embodiment body 602 of MPH 600 may be constructed of any suitable material in the art including but not limited to metal, plastic and the like. In a preferred embodiment, body 602 can be made of a thermoplastic rubber. Also, there can be a holder 604 that fits on needle cover 603. Holder 604 may be constructed of any suitable material known in the art, in the present invention holder 604 was constructed of plastic. In addition, holder 604 may be generally "C" shaped so as to be able to receive a portion of body 602. In normal operation the practitioner may hold MVE between the forefinger and thumb, or the practitioner may connect the MPH of MVE to vial 608 via holder 604. The operation of the MVE is generally the same no matter which method of use is implanted, that is to say the practitioner will point the front end of MPH in the direction of venous penetration and/or extraction.

In another hand held embodiment of the present invention, as seen in FIGS. 23*a*-23*d*, the holder 680 may have a generally polygonal shape, and a corresponding polygonal body 681, any suitable polygonal shape known in the art including but not limited to a hexagon, pentagon and the like may be used. In a preferred embodiment, holder has a hexagonal shape and body 681 has a corresponding hexagonal shape. Holder 680 may also have a bottom portion 680*a* used to secure holder 680 to needle cover 685. Bottom portion 680*a* may be generally cylindrical in shape with a hollowed out center, this allows the practitioner place holder 680 over and around needle cover 685. Also, there can be a string 682 located at a rear end, for hand held use. The string can be made of any type of material known in the art including but not limited to nylon, plastic, and the like. In a preferred embodiment a lanyard was implemented. In normal operation the practitioner may place holder 680 over needle cover 685. After the holder is securely attached to needle cover 685 the practitioner may then slide body 681 of MPH 690 through hexagonal holder 680. This embodiment also may be hand held.

Drawing one's attention to FIGS. 24*a*-24*i* is another embodiment of the present invention. In this embodiment the MPH 690 may be attached to the front end of a flashlight for hand held use. Alternatively, the MPH may be attached to needle cover 691 as in previously discussed embodiments. This embodiment may also implement a ring 692, which may be used to secure MVE to a key chain or the like.

Figure 25A:
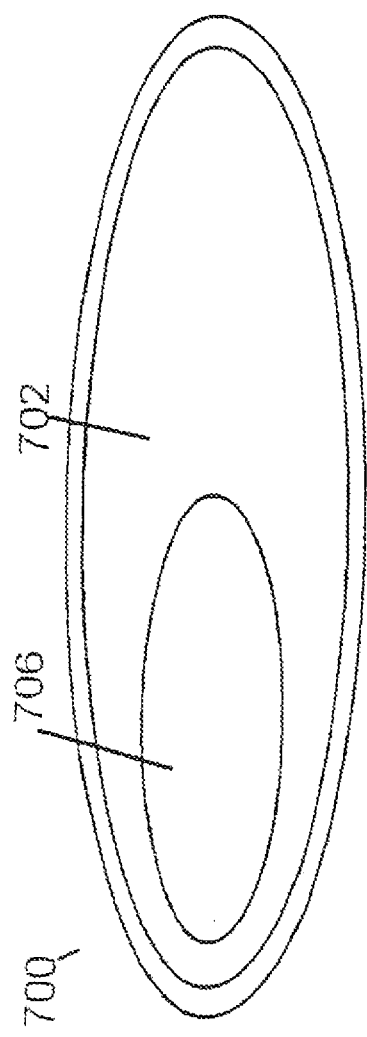
FIG. 25a is a top view of another embodiment of the MVE of the present invention.
Figure 25B:
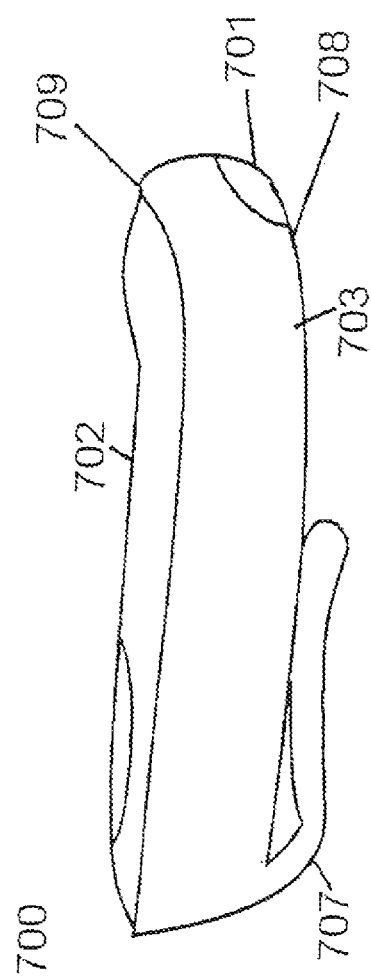
Figure 25E:
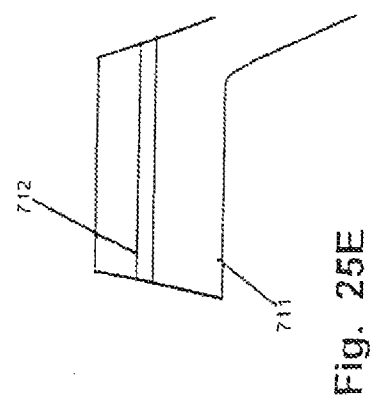
Figure 25C:
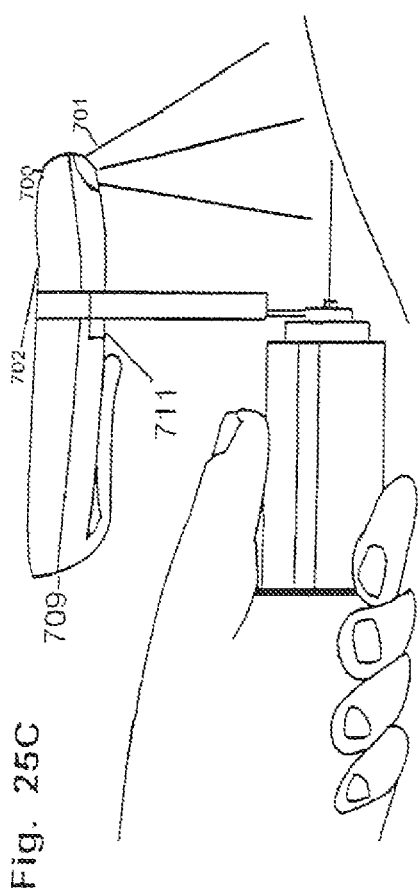
FIG. 25c is a side view of the MVE depicted in FIG. 25a attached to a vial.
Figure 25D:
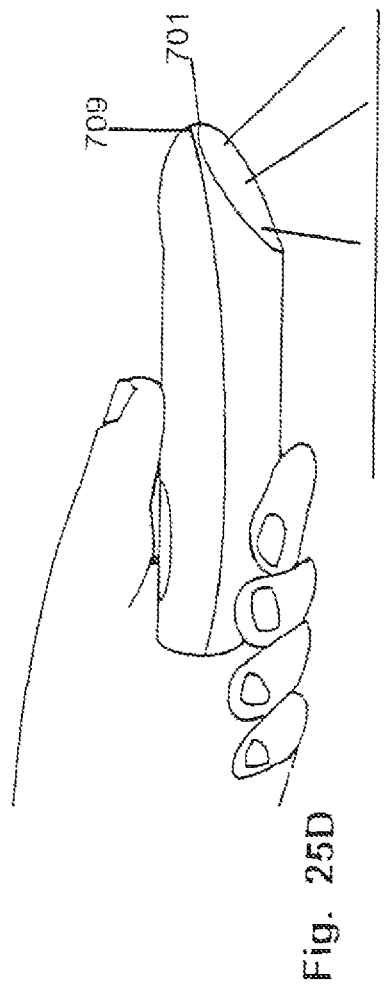
FIG. 25d is a side view of the MVE depicted in FIG. 25a being held in the hand of a practitioner.

In another embodiment, the MPH 701 of the MVE 700 may be contained in an oval housing, as seen in FIGS. 25*a*-25*d*. In this embodiment, the housing may have a top, generally, oval surface 702 and a bottom, generally, oval surface 703. Both top surface 702 and bottom surface 703 may be snap fitted to form MVE 700. Both top surface 702 and bottom surface 703 may be constructed from any suitable material. Located on top surface 702 may be switch panel 704. Switch panel 704 may be made from the same material as top and bottom surfaces 702 and 703 respectively, or switch 704 may be made of a rubber, as in the preferred embodiment. Switch 704 may be designed to turn the MVE "on and off" via a pressing motion or a sliding motion. Switch 704 may have bored grooves 706 used to facilitate the sliding of switch 704, or switch 704 may have ribs located on switch 704, also used to facilitate sliding. In a preferred embodiment either top surface 702 or bottom surface 703 may have an outer generally oval groove 709. Groove 709 may be used to secure MVE to a vial or syringe, as seen in FIG. 25*c*. Located on bottom surface 703 may be a flexible clip 707. Clip 707 may be integrally formed with bottom surface 703, in which case clip 707 may be constructed from the same material as bottom surface 703. Conversely clip 707 may be a separate member attached to either bottom surface 703 or top surface 702, in which case clip 707 may be constructed of any suitable material known in the art. In a preferred embodiment, clip 707 was integrally formed with bottom surface 703. Clip 707 may be used to secure MVE 700 to the shirt pocket, or the like, of a practitioner. This will give the practitioner easy quick access to the MVE. Bottom surface 703 may slope in an upwards fashion near the front end of bottom surface 703, as seen in FIGS. 25a-25d. Located near the front end of bottom surface 703 may be a generally rectangular opening 708. In a preferred embodiment, MPH 701 may be set inside of the housing and have its front face even with the plane of surface 703. In another embodiment, MPH 701 may have its front face raised above the plane of surface 703, and in a third embodiment MPH 701 may have it's front face recessed below the plane of surface 703. As mentioned previously, this embodiment of the MVE may be hand held or attached to a vial, as in other embodiments. This arrangement may be observed on FIGS. 25c and 25d. If the latter method of use is used, i.e. attached to a vial, the needle cover 710 may have a generally rectangular top portion 711 that has a width larger enough to receive the MVE. In addition, located on the inside of top portion 711 may be at least one tongue portion 712, as seen in FIG. 32d, used to mate with groove 709. Conversely, there can be at least one groove on an inside surface of top portion 711, and either top or bottom surface, 702 and 703 respectively, may have an outer generally oval tongue. Operation of this embodiment is similar to previous mentioned embodiments.

Two additional embodiments of the present invention may be seen in FIGS. 26a-27d. First, the embodiment depicted in FIGS. 26a-26d. This embodiment includes a MPH that may be either hand held, as seen in FIG. 26d, or mounted on to a needle cover 802, as seen in FIG. 26b. In the latter configuration, the operation of the mounting of MPH is similar to the other previous embodiments. The MPH has an adjustable rear end 801 that may have an orifice 803 to receive top portion 804 of needle cover 802. In the hand held configuration, rear end 801 of MPH 805 may be slidably attached to a battery holder 810. In this embodiment, battery holder 810 may be generally pear shaped with a wider rear end 811 and a tapered front end 812. Located near front end 812 may be a bored generally rectangular slot 813. Located inside of slot 813 may be at least one contact. Rear end 804 of MPH 805 may be generally the same shape as bored slot 813. Also, located on a surface of rear end 804 may be at least one contact. In normal operation the practitioner may slide rear end 804 from either the left or right side or insert rear end 804 of MPH 805 into slot 813 from the front end.

Figure 27C:
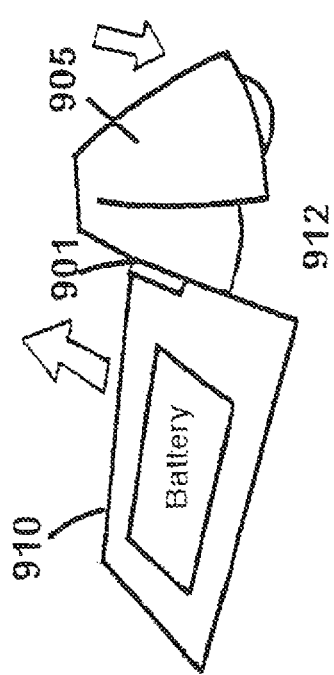
FIG. 27c is a side view of the MVE depicted in FIG. 27a with the MPH being slidably attached.
Figure 27D:
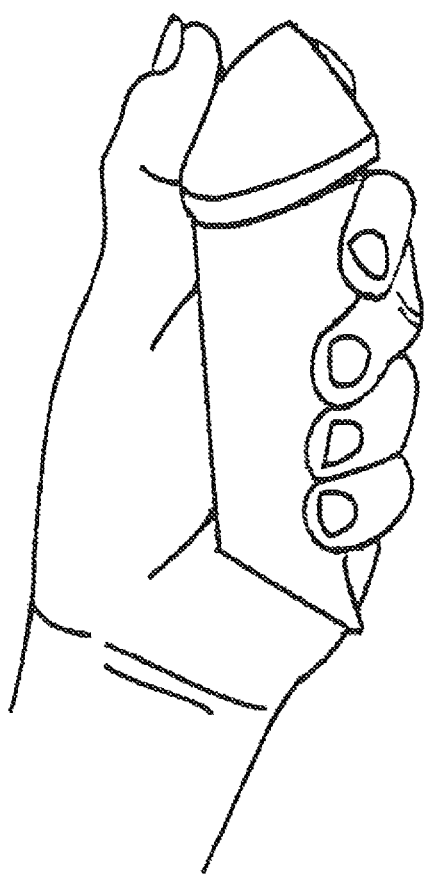
FIG. 27d is a side view of the MVE depicted in FIG. 27e 34a being held in the hand of a practitioner.

Similar to the just mentioned embodiment is the embodiment depicted in FIGS. 27a-27d. This embodiment includes a MPH that may be either hand held, as seen in FIG. 27d, or mounted to a needle'cover 902, as seen in FIG. 27b. In the latter configuration, the operation of the mounting of MPH is similar to the other previous embodiments. The MPH may have an orifice 903 to receive top portion 904 of needle cover 902. In the hand held configuration, rear end 901 of MPH 905 may be slidably attached to a battery holder 910. In this embodiment battery holder may be generally rectangular in shape. Located near front end 912 may be a bored generally rectangular slot 913. Located inside of slot 913 may be at least one contact. Rear end 904 of MPH 905 may be generally the same shape as bored slot 913, also located on a surface of rear end 904 may be at least one contact. In normal operation the practitioner may slide rear end 904 into top slot 913.

Figure 29:
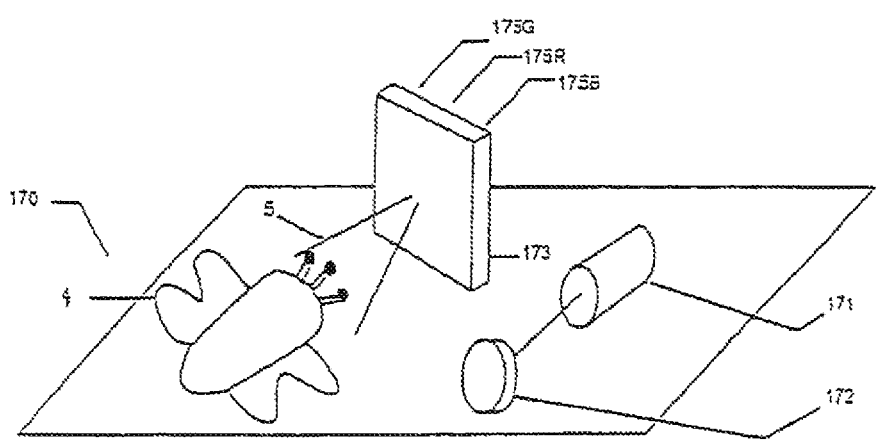
FIG. 29 depicts a prior art scanning laser based camera.

The MPH 2 will now be described. FIG. 29 shows a prior art scanning laser-based camera (hereinafter SLBC) 170 of Microvision, Inc. FIG. 17 is taken from Microvision's website: (http://www.microvision.com/technology/imaging-_works.html) dated Jan. 7, 2006, herein incorporated by reference. The SLBC 170 includes a laser source 171 which gets reflected off mirror 172 to a MEMS scanner 173. The MEMS scanner 173 has a reflective surface that can be oscillated in both the X and Y axis. The oscillation of the MEMS scanner 173 is controlled by electronics (not shown) so that the reflected laser beam is moved in a raster pattern. To create a color camera, the laser source is a combination of a red, green and blue laser, thereby forming the color white. Three photodetectors, one responsive to red 175R, one responsive to blue 175B, and one responsive to green 175G are positioned on the SLBC 170 and receive the rastered laser light reflected off object 176. The output of the photodetectors 175R, 175B, and 175B provide an analog rastered image representative of the object 176. The outputs of the photodetectors are converted from an analog signal to a digital signal by D/A converters (not shown). A controller (not shown) determines the instantaneous rastered laser light position and converts that to an appropriate pixel location. The controller then and writes the digitized RGB values to an appropriate pixel memory location. By repeating this step for each pixel location, a digitized version of the object is stored in memory. Each raster sweep of the field of view 4 results in a new image being stored. By sweeping at video rates, video images can be captured.

A publication in Laser Focus World, December 2004, authored by Chris Wiklof, entitled "Display technology spawns laser camera", herein incorporated by reference, describes the SLBC of FIG. 29 in even greater detail.

Figure 30:
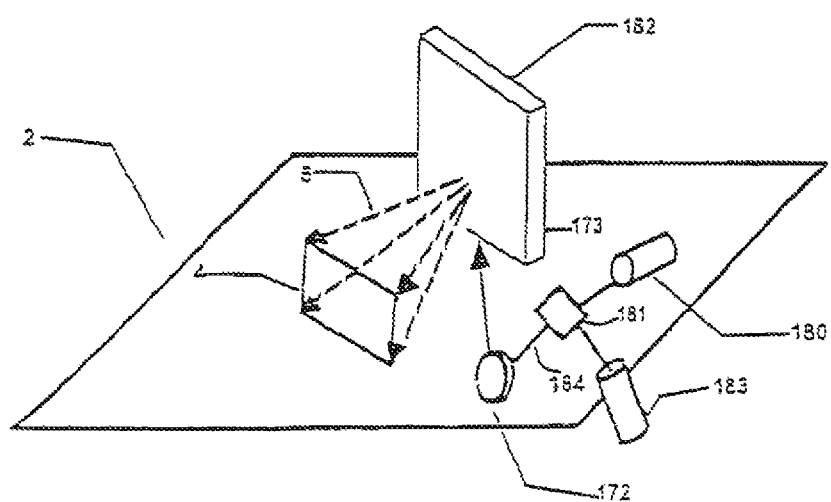
FIG. 30 illustrates an example of the MPH of the present, invention.

FIG. 30 illustrates an embodiment of the MPH 2 in accordance with the present invention. A single colored laser 180, for example a 630 nm semiconductor red laser, is projected into combiner 181. A semiconductor laser 183 is also projected into the combiner 181. Laser 183 may have a wavelength from 700 nm to 1000 nm, with a preferred wavelength of 740 nm. An illustrative example of a semiconductor 740 nm laser is Sacher Lasertechnik's Fabry Perot Diode Laser 740 nm, 10 mw, model number FP-0740-10. The combiner 181 outputs a combined laser beam 184 which is the combination of the 630 nm red and the 740 nm laser beams. Combiners for combining light from two lasers which emit light at different wavelengths are well known in the art and will not be further described herein. The combined laser beam 184 is positioned to hit off mirror 172 and then to hit the MEMS scanner 173. The MEMS scanner moves in a raster pattern thereby causing the combined laser beam to move along optical path 5 forming a raster pattern at the field of view 4. A photodetector 182 which is responsive to the 740 nm wavelength is provided and receives 740 nm light reflected off objects in the field of view. The photodetector 182 outputs an analog signal representing the amount of 740 nm light received. An illustrative example of a photodetector is Roithner Lasertechnik's model number EPD-740-1.

Figure 31:
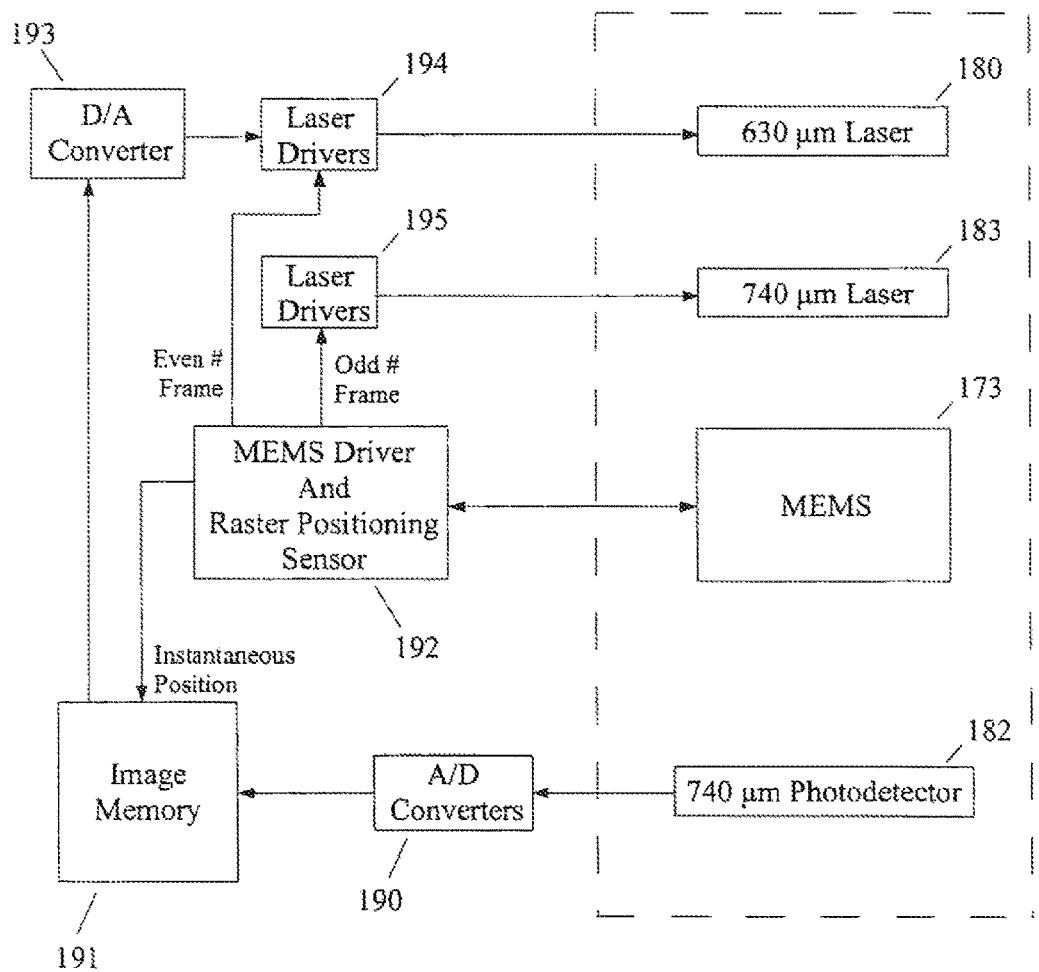
FIG. 31 shows a control block diagram for the MPH.

FIG. 31 shows a control block diagram for controlling the elements in FIG. 30. A first mode of operation which will be referred to hereinafter as an "Alternating Frame Mode" (AFM) follows.

In the AFM mode, an electronic block 192 for driving the MEMS driver and for sensing the position of the raster scanner is provided 192. This block generates the signals required to drive the MEMS scanner 173 in a raster pattern, and also determines the exact instantaneous location of the MEMS scanner and communicates this information to an image memory 191. This electronic block 192 also generates output signals and indicates whether the current frame (a frame is a complete raster of the field of view) is an odd number Frame 1 or an even number Frame 2 (essentially the two signals are opposite and switch polarity every other frame). The operation is as follows. The MEMS 173 is driven in a raster pattern. The first full frame after achieving a stable raster pattern will be identified as an odd number frame and the laser driver 195 for the 740 nm laser 183 is turned on for the entire frame. During this time the laser drive 194 for the 630 nm laser is turned off. The light from the 740 nm is absorbed by the veins in a patient's body and reflected by the skin of the patient, thus forming a contrasted image that is then sensed and converted into an analog signal by 740 nm photodetector 182. The analog signal is then passed through an A/D converter 190 which outputs a digital representation to image memory 191. Image memory 191 also receives instantaneous position information from the electronic block 192, and based upon such information, the digital representation is stored in a memory location corresponding to a particular pixel. This is repeated for each pixel within the odd frame. Upon completion of the odd frame, the image memory contains the image of the veins within the field of view of the MPH. During the even number frame, the laser driver 195 to the 740 nm laser is turned off. The data in the image memory 191 is read out as a function of the instantaneous position information provide by the electronic block 192 and provide to a D/A converter 193 which outputs an analog signal to laser drive 194 which drives the 630 nm laser. In this manner, the image that was stored in the odd number frame is projected by the 630 nm laser 180 in the even number frame. In this manner, the veins that are in the field of view become visible to the practitioner.

Figure 32:
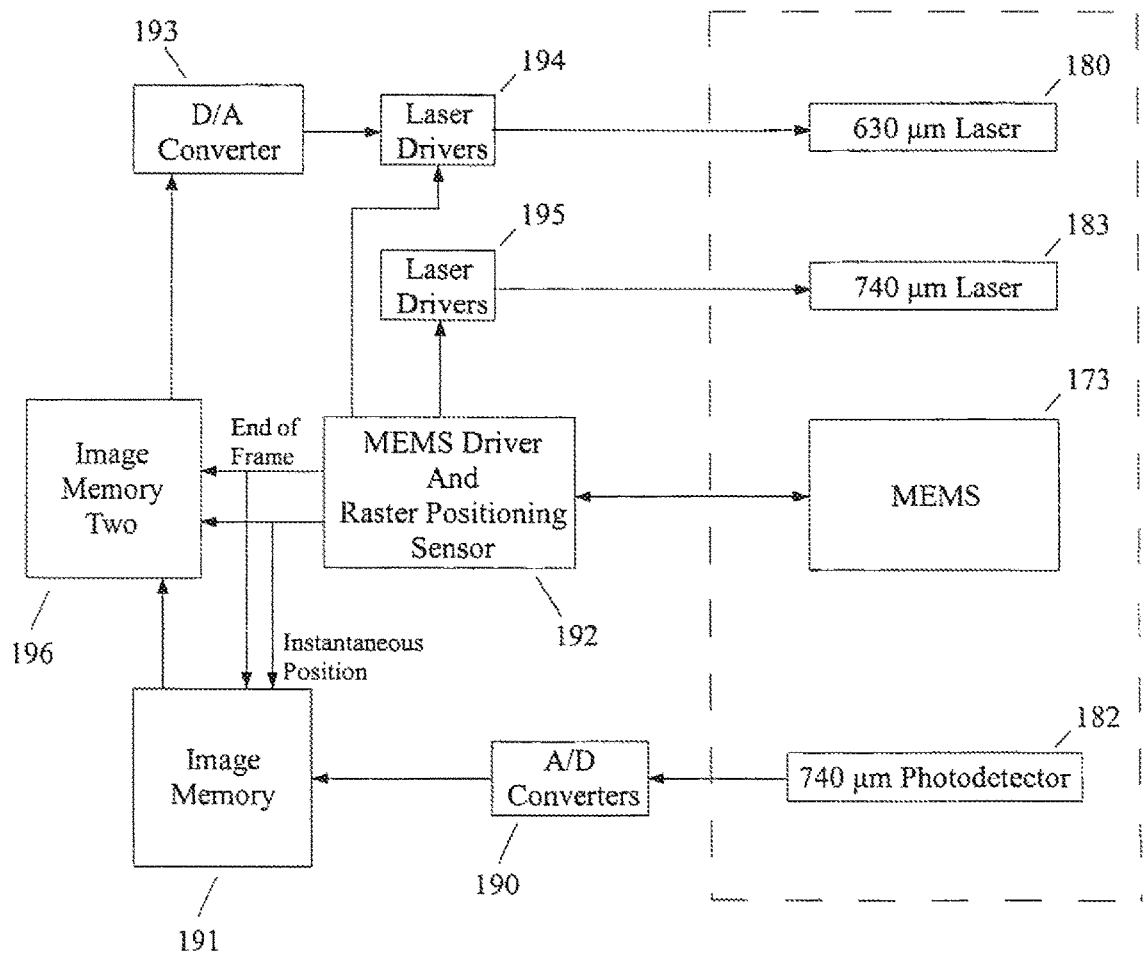
FIG. 32 shows the Dual Buffer Mode of operation of the MPH.

A second mode of operation is shown in FIG. 32. This mode shall be referred to hereinafter as the "Dual Buffer Mode" (DBM). In the DBM, a second image memory called image memory two 196 is added. In the DBM, the laser driver to the 740 nm laser is turned on for every frame and in each frame the image of the veins is captured and stored in image memory 191 exactly as described previously in the AFM mode: However, in this case the electronic block 192 provides an end of frame indication to both image memory two 196 and image memory 191 which causes the entire image stored in the image memory 191 to be transferred to image memory two 196 during the blanking time of the raster scan (the time after the raster scan is completed but before the next raster scan starts). During the next frame, the contents of image memory two 196 is then projected by the 630 nm laser onto the field of view. In this manner, the visible image projected is always on frame behind the actual image captured. Provided the frame rate is fast enough, this delay should not be apparent to the practitioner. Frame rates in excess of 30 frames per second can easily be achieved with the MEMS scanner provided herein.

The DBM mode is advantaged as compared to the AFM in that the visible laser is on every frame, and therefore is twice as bright. However, the AFM mode is advantaged in that it only requires a single memory buffer and therefore is more cost effective than the DBM mode.

Figure 33:
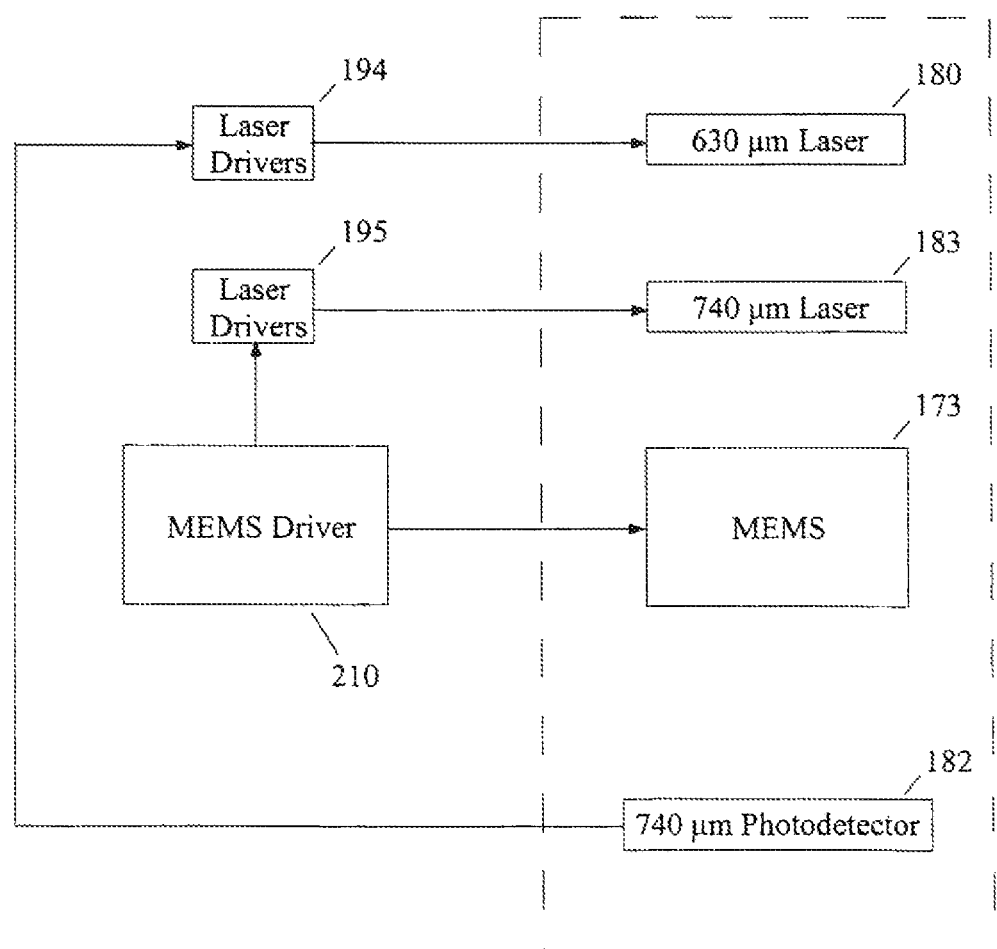
FIG. 33 depicts the Real Time Mode of operation of the MPH.

A third mode of operation is illustrated in FIG. 33. This mode shall be referred to hereinafter as the "Real Time Mode" (RTM). In the RTM the MEMS 173 is driven in a raster pattern by a MEMS driver 210. The laser driver 195 to the 740 nm laser is turned on all the time. The reflected light is received by the 740 nm photodetector 182 and the analog signal produced is connected to the laser driver 194 for the 630 nm laser 180. In this manner the red laser 180 projects nearly instantaneously the signal that is being received by the photodetector 182. The only delay is dictated by the speed of the photodetector and the laser drive 194 circuitry. Accordingly, there is no need for an image memory buffer and associated D/A converters and A/D converters. Further, since the image is never stored, there is no requirement to sense the instantaneous position of the laser for the purpose of clocking the image into memory or for projecting the visible image. In fact, in this RTM, the raster pattern does not need to be as steady and repeatable as that of the other modes, thereby possibly decreasing the complexity and cost of the MEMS and associated drive circuitry.

The RTM is so forgiving of the scan pattern that practically any dense scanning pattern can be utilized, for example, a two dimensional moving mirror is provided by Fraunhofer IPMS. In a press release dated Jan. 3, 2005 they described a two dimensional mirror as follows:

"Projection devices based on laser scanning are a very interesting alternative to matrix displays. A modulated laser and a deflection unit are necessary. Using micro scanning mirrors for implementing the laser beam deflection in a projection device has many advantages. In particular, micro scanning mirrors, which operate resonantly in both directions, enable the development of systems with very small size, high deflection angles with low voltage and low power consumption. The presented demonstrator uses a commercial laser module and a 2D micro scanning mirror operated with deflection frequencies of 9.4 kHz and 1.4 kHz. The device uses both axes to perform a sinusoidal oscillation, which causes a beam trajectory that describes a Lissajous pattern with high density, instead of the usually implemented linear scanning. Therefore, mirrors with low ratio of horizontal and vertical deflection frequency can be used. This kind of micro scanning mirrors can be fabricated easily and cost effective. The control circuit is developed with an FPGA and provides a resolution of 256×256 monochromatic pixels. Programmable counters are used for generating the mirror driving signals and for determining the beam position. Mirror excitation and image synchronization work without feedback loop. This means, no complicated optical or electronic synchronization techniques are needed. This simplifies micro scanning mirror and control circuit and enables low cost production. Applications of the projection device are displays, laser marking and laser exposure."

In the RIM of FIG. 33, the MEMS could be replaced by the two-dimensional mirror of Fraunhofer IPMS which creates a Lissajous pattern with high density instead of the raster pattern. The visible laser will simply follow nearly instantaneously the image detected by the 740 nm laser detector.

In the embodiments herein the visible light transmitted was a red laser. However, any visible color or combination of color could be transmitted. For example, three laser RGB could be utilized to transmit full color images onto the field of view.

While in the embodiments herein a single two-dimensional mirror which moves in two axis was used for steering the beam, other beam steering arrangements could be used. For example, the outgoing laser beams can be bounced first off a one dimensional high speed scanning mirror and then off a second lower speed mirror scanning in the opposite direction. There are many other methods known to those skilled in the art for creating raster and other scanned laser patterns.

While many of the embodiments described herein utilized vial holders with needles, there are many other medical procedures which need to view the veins. The invention is not intended to be limited to devices which attach to vial holders.

We claim:

1. A handheld vein-image-enhancing device configured to project in-focus vein images on a surface of a target to permit mobile imaging of veins, said device comprising:
   a first laser configured to selectively emit light at a first wavelength;
   a scanner configured to scan said first wavelength onto the surface of the target in a plurality of successive frames;
   a photo detector configured to receive a corresponding plurality of contrasted images for each of said plurality of successive frames, each contrasted image formed from differential absorption and reflection of said first wavelength of light by subcutaneous veins and surrounding tissue of the target; said photo detector configured to output an analog signal of each of said contrasted images;
   an analog-to-digital converter configured to receive and convert each said analog signal of each of said contrasted images from said photo detector, and to output a digital signal therefrom as a digital image for each of said plurality of successive frames;
   a first image memory configured to successively receive and store said digital image for each of said plurality of successive frames;
   a second image memory configured to receive and store said stored digital image from said first image memory, as said first image memory receives a next said digital image of said plurality of successive frames;
   a digital-to-analog converter configured to receive and convert said stored digital image from said second image memory, and to output a converted analog signal thereof;
   a second laser configured to selectively emit a second wavelength; said second laser further configured to receive and use said converted analog signal from said digital-to-analog converter to project each of said corresponding plurality of contrasted images for each of said plurality of successive frames, using said scanner, to reveal the subcutaneous veins therein.

2. The handheld vein-image-enhancing device according to claim 1 wherein each of said plurality of successive frames comprise complete raster patterns, and wherein each of said complete raster frames comprise a grid of pixels.

3. The handheld vein-image-enhancing device according to claim 2 wherein said grid of pixels comprises a grid of 1000 pixels by 1000 pixels.

4. The handheld vein-image-enhancing device according to claim 2 further comprising a combiner, said combiner configured to combine said first wavelength of light from said first laser and said second wavelength of laser light from said second laser; and wherein said combiner is further configured to transmit said combined laser light along a single optical path to said scanner.

5. The handheld vein-image-enhancing device according to claim 4 further comprising a sensor, said sensor configured to determine an instantaneous position of said scanner relative to the surface of the target; said instantaneous position being determined, converted, and stored in said first image memory for each pixel of said grid of pixels; said instantaneous position for each said pixel being received by said second laser, for each said projection of said corresponding plurality of contrasted images for each of said plurality of successive frames to be in-focus on the surface of the target to represent actual vein sizes and vein locations, regardless of device-to-surface distances.

6. The handheld vein-image-enhancing device according to claim 5 wherein said scanner is a scanner from the group of scanners consisting of: a MEMS scanner; a single biaxial mirror; and a first mirror and a second mirror each configured to pivot about a single axis, wherein said emitted light is directed by said pivoting of said first mirror to bounce off of said first mirror toward said second mirror, said second mirror pivoting to direct said beam toward the surface of the target to produce said pattern.

7. The handheld vein-image-enhancing device according to claim 6 wherein said vein-image-enhancing device is further configured to perform image processing on each of said plurality of contrasted images for each of said plurality of successive frames.

8. The handheld vein-image-enhancing device according to claim 7 wherein said first wavelength of light comprises an infrared wavelength of light.

9. The handheld vein-image-enhancing device according to claim 8 wherein said second wavelength of light comprises a visible wavelength of light.

10. The handheld vein-image-enhancing device according to claim 9 wherein said second image memory is configured to successively receive and store said digital image from said first image memory at a rate equal to a frame rate of said scanner.

11. The handheld vein-image-enhancing device according to claim 10 wherein a rate of said projection of said successive frames occurs at least at a rate of 30 frames per second.

12. The handheld vein-image-enhancing device according to claim 1 further comprising a combiner, said combiner configured to combine said first wavelength of light from said first laser and said second wavelength of laser light from said second laser; and wherein said combiner is further configured to transmit said combined laser light along a single optical path to said scanner.

13. The handheld vein-image-enhancing device according to claim 1 further comprising a sensor, said sensor configured to determine an instantaneous position of said scanner relative to the surface of the target; said instantaneous position being determined, converted, and stored in said first image memory for each pixel of said grid of pixels; said instantaneous position for each said pixel being received by said second laser, for each said projection of said corresponding plurality of contrasted images for each of said plurality of successive frames to be in-focus on the surface of the target to represent actual vein sizes and vein locations, regardless of device-to-surface distances.

14. The handheld vein-image-enhancing device according to claim 1 wherein said scanner is a scanner from the group of scanners consisting of: a MEMS scanner; a single biaxial mirror; and a first mirror and a second mirror each configured to pivot about a single axis, wherein said emitted light is directed by said pivoting of said first mirror to bounce off of said first mirror toward said second mirror, said second mirror pivoting to direct said beam toward the surface of the target to produce said pattern.

15. The handheld vein-image-enhancing device according to claim 1 wherein said vein-image-enhancing device is further configured to perform image processing on each of said plurality of contrasted images for each of said plurality of successive frames.

16. The handheld vein-image-enhancing device according to claim 1 wherein said first wavelength of light comprises an infrared wavelength of light.

17. The handheld vein-image-enhancing device according to claim 16 wherein said second wavelength of light comprises a visible wavelength of light.

18. The handheld vein-image-enhancing device according to claim 1 wherein said second image memory is configured to successively receive and store said digital image from said first image memory at a rate equal to a frame rate of said scanner.

19. The handheld vein-image-enhancing device according to claim 18 wherein a rate of said projection of said successive frames occurs at least at a rate of 30 frames per second.

\* \* \* \* \*